United States Patent
Lu et al.

(10) Patent No.: US 12,215,331 B2
(45) Date of Patent: Feb. 4, 2025

(54) ABIOTIC STRESS TOLERANT PLANTS AND METHODS

(71) Applicants: PIONEER OVERSEAS CORPORATION, Johnston, IA (US); SINOBIOWAY BIO-AGRICULTURE GROUP CO. LTD., Beijing (CN)

(72) Inventors: Guihua Lu, San Diego, CA (US); Guangwu Chen, Beijing (CN); Guanfan Mao, Beijing (CN); Changgui Wang, Beijing (CN); Guokui Wang, Beijing (CN); Yu Zhang, Beijing (CN)

(73) Assignees: SINOBIOWAY BIO-AGRICULTURE GROUP CO LTD; PIONEER OVERSEAS CORPORATION

( * ) Notice: Subject to any disclaimer, the term of this patent is extended or adjusted under 35 U.S.C. 154(b) by 263 days.

(21) Appl. No.: 17/629,318

(22) PCT Filed: Jul. 30, 2019

(86) PCT No.: PCT/CN2019/098305
§ 371 (c)(1),
(2) Date: Jan. 21, 2022

(87) PCT Pub. No.: WO2021/016840
PCT Pub. Date: Feb. 4, 2021

(65) Prior Publication Data
US 2022/0259613 A1    Aug. 18, 2022

(51) Int. Cl.
C12N 15/82    (2006.01)
C07K 14/415   (2006.01)

(52) U.S. Cl.
CPC ........ *C12N 15/8273* (2013.01); *C07K 14/415* (2013.01)

(58) Field of Classification Search
None
See application file for complete search history.

(56) References Cited

U.S. PATENT DOCUMENTS

2006/0123505 A1*   6/2006   Kikuchi .............. C07K 14/415
                                              536/23.6

FOREIGN PATENT DOCUMENTS

CN    106916826 A    7/2017
CN    107217057 A    9/2017

OTHER PUBLICATIONS

Guo, Haiwei H., Juno Choe, and Lawrence A. Loeb. "Protein tolerance to random amino acid change." Proceedings of the National Academy of Sciences 101.25 (2004): 9205-9210. (Year: 2004).*
Ng, Pauline C., and Steven Henikoff. "Predicting deleterious amino acid substitutions." Genome research 11.5 (2001): 863-874. (Year: 2001).*
Ptitsyn, Andrey A., and Jeffrey M. Gimble. "True or false: All genes are rhythmic." Annals of medicine 43.1 (2011): 1-12. (Year: 2011).*
"Genbank Accession No. XP_015641111.1", Aug. 7, 2018 (Aug. 7, 2018).
International Search Report and Written Opinion for International Application No. PCT/CN2019/098305, Mailed Apr. 29, 2020.
International Preliminary Report on Patentability for International Application No. PCT/CN2019/098305, mailed Feb. 10, 2022, 07 Pages.

* cited by examiner

*Primary Examiner* — Amjad Abraham
*Assistant Examiner* — Kelsey L McWilliams

(57) ABSTRACT

Provided are isolated polynucleotides and polypeptides, and recombinant DNA constructs that are useful for conferring improved drought tolerance and yield in a plant. Also provided are genome edited plants, or plants expressing a recombinant DNA construct, having improved drought tolerance and yield. Further provided are methods for improving drought tolerance and yield by introducing a genome edit in a plant or expressing a recombinant DNA construct in a plant.

14 Claims, No Drawings
Specification includes a Sequence Listing.

ABIOTIC STRESS TOLERANT PLANTS AND METHODS

FIELD

The field of the disclosure relates to plant breeding and genetics and, particularly, relates to improving tolerance to abiotic stress in plants.

REFERENCE TO SEQUENCE LISTING SUBMITTED ELECTRONICALLY

The official copy of the sequence listing is submitted electronically via EFS-Web as an ASCII formatted sequence listing with a file named RTS22593S_SEQListing.txt created on Jul. 18, 2019 and having a size of 229 kilobytes and is filed concurrently with the specification. The sequence listing comprised in this ASCII formatted document is part of the specification and is herein incorporated by reference in its entirety.

BACKGROUND

Stresses to plants may be caused by both biotic and abiotic agents. For example, biotic causes of stress include infection with pathogen, insect feeding, and parasitism by another plant such as mistletoe. Abiotic stresses include, for example, excessive or insufficient available water, temperature extremes, and synthetic chemicals such as herbicides.

Abiotic stress is the primary cause of crop loss worldwide, causing average yield losses of more than 50% for major crops (Boyer, J. S. (1982) Science 218:443-448; Bray, E. A. et al. (2000) In Biochemistry and Molecular Biology of Plants, edited by Buchannan, B. B. et al., Amer. Soc. Plant Biol., pp. 1158-1249; Mushtaq et al. (2018) Journal of Plant Physiology 224-225: 156-162).

Accordingly, there is a need to develop compositions and methods that increase tolerance to abiotic stress in plants. This invention provides such compositions and methods.

SUMMARY

The following embodiments are among those encompassed by the disclosure:

In one embodiment, the present disclosure includes an isolated polynucleotide, encoding a polypeptide with amino acid sequence of at least 90% sequence identity to SEQ ID NO: 3, 6, 9, 12, 15, 18, 21, 24, 27, 30, 54, 56, 58, 60, 62, 64, 66, 68, 70, 72, 74, 76, 78, 80, 82, 84, 86, 88, 90, 92, 94, 96, 98, 100, 102, 104, 106, 108, 110, or 112, wherein increased expression of the polynucleotide in a plant enhances drought tolerance. In certain embodiments, the isolated polynucleotide encodes the amino acid sequence of SEQ ID NO: 3, 6, 9, 12, 15, 18, 21, 24, 27, 30, 54, 56, 58, 60, 62, 64, 66, 68, 70, 72, 74, 76, 78, 80, 82, 84, 86, 88, 90, 92, 94, 96, 98, 100, 102, 104, 106, 108, 110, or 112. In certain embodiments, the isolated polynucleotide comprises the nucleotide sequence of SEQ ID NO: 1, 2, 4, 5, 7, 8, 10, 11, 13, 14, 16, 17, 19, 20, 22, 23, 25, 26, 28, 29, 53, 55, 57, 59, 61, 63, 65, 67, 69, 71, 73, 75, 77, 79, 81, 83, 85, 87, 89, 91, 93, 95, 97, 99, 101, 103, 105, 107, 109, or 111. In certain embodiments, increased expression of the polynucleotide in a plant enhances grain yield under drought conditions.

The present disclosure also provides a recombinant DNA construct comprising an isolated polynucleotide operably linked to at least one heterologous regulatory element, wherein the polynucleotide encodes a polypeptide with amino acid sequence of at least 90% sequence identity to SEQ ID NO: 3, 6, 9, 12, 15, 18, 21, 24, 27, 30, 54, 56, 58, 60, 62, 64, 66, 68, 70, 72, 74, 76, 78, 80, 82, 84, 86, 88, 90, 92, 94, 96, 98, 100, 102, 104, 106, 108, 110, or 112.

The present disclosure further provides a modified plant or seed having increased expression or activity of at least one polynucleotide encoding a polypeptide with amino acid sequence of at least 90% sequence identity to SEQ ID NO: 3, 6, 9, 12, 15, 18, 21, 24, 27, 30, 54, 56, 58, 60, 62, 64, 66, 68, 70, 72, 74, 76, 78, 80, 82, 84, 86, 88, 90, 92, 94, 96, 98, 100, 102, 104, 106, 108, 110, or 112. In certain embodiments, the modified plant or seed comprises in its genome a recombinant DNA construct comprising a polynucleotide operably linked to at least one heterologous regulatory element, wherein the polynucleotide encodes a polypeptide with amino acid sequence of at least 90% sequence identity to SEQ ID NO: 3, 6, 9, 12, 15, 18, 21, 24, 27, 30, 54, 56, 58, 60, 62, 64, 66, 68, 70, 72, 74, 76, 78, 80, 82, 84, 86, 88, 90, 92, 94, 96, 98, 100, 102, 104, 106, 108, 110, or 112. In certain embodiments, the modified plant exhibits improved drought tolerance and increased grain yield when grown under drought conditions compared to a control plant.

In certain embodiments, the modified plant or seed comprises a targeted genetic modification at a genomic locus comprising a polynucleotide encoding a polypeptide with amino acid sequence of at least 90% sequence identity to SEQ ID NO: 3, 6, 9, 12, 15, 18, 21, 24, 27, 30, 54, 56, 58, 60, 62, 64, 66, 68, 70, 72, 74, 76, 78, 80, 82, 84, 86, 88, 90, 92, 94, 96, 98, 100, 102, 104, 106, 108, 110, or 112, wherein the targeted genetic modification increases the expression and/or activity of the polypeptide. In certain embodiments, the modified plant exhibits improved drought tolerance, such as increased grain yield when grown under drought conditions compared to a control plant.

In certain embodiments, the plant is selected from the group consisting of rice, maize, soybean, sunflower, sorghum, canola, wheat, alfalfa, cotton, barley, millet, sugar cane and switchgrass.

Also provided are methods for increasing drought tolerance in a plant, the method comprising increasing the expression of at least one polynucleotide encoding a polypeptide with amino acid sequence of at least 90% sequence identity to SEQ ID NO: 3, 6, 9, 12, 15, 18, 21, 24, 27, 30, 54, 56, 58, 60, 62, 64, 66, 68, 70, 72, 74, 76, 78, 80, 82, 84, 86, 88, 90, 92, 94, 96, 98, 100, 102, 104, 106, 108, 110, or 112 in the plant, wherein the plant exhibits increased drought tolerance when compared to the control plant.

In certain embodiments, the method for increasing drought tolerance comprises: (a) introducing into a regenerable plant cell a recombinant DNA construct comprising a polynucleotide operably linked to at least one heterologous regulatory element, wherein the polynucleotide encodes a polypeptide having an amino acid sequence of at least 80% sequence identity, when compared to SEQ ID NO: 3, 6, 9, 12, 15, 18, 21, 24, 27, 30, 54, 56, 58, 60, 62, 64, 66, 68, 70, 72, 74, 76, 78, 80, 82, 84, 86, 88, 90, 92, 94, 96, 98, 100, 102, 104, 106, 108, 110, or 112; and (b) generating the plant, wherein the plant comprises in its genome the recombinant DNA construct.

In certain embodiments, the method for increasing drought tolerance comprises: (a) introducing into a regenerable plant cell a targeted genetic modification at a genomic locus comprising a polynucleotide encoding a polypeptide having an amino acid sequence of at least 80% sequence identity, when compared to SEQ ID NO: 3, 6, 9, 12, 15, 18, 21, 24, 27, 30, 54, 56, 58, 60, 62, 64, 66, 68, 70, 72, 74, 76, 78, 80, 82, 84, 86, 88, 90, 92, 94, 96, 98, 100, 102, 104, 106, 108, 110, or 112; and (b) generating the plant, wherein the plant comprises in its genome the introduced genetic modification and has increased expression and/or activity of the polypeptide. In certain embodiments, the targeted genetic modification is introduced using a genome modification technique selected from the group consisting of a polynucleotide-guided endonuclease, CRISPR-Cas endonucleases, base editing deaminases, a zinc finger nuclease, a transcription activator-like effector nuclease (TALEN), an engineered site-specific meganucleases, or an Argonaute. In certain embodiments, the targeted genetic modification is present in (a) the coding region; (b) a non-coding region; (c) a regulatory sequence; (d) an untranslated region; or (e) any combination of (a)-(d) of the genomic locus that encodes a polypeptide comprising an amino acid sequence that is at 80% sequence identity, when compared to SEQ ID NO: 3, 6, 9, 12, 15, 18, 21, 24, 27, 30, 54, 56, 58, 60, 62, 64, 66, 68, 70, 72, 74, 76, 78, 80, 82, 84, 86, 88, 90, 92, 94, 96, 98, 100, 102, 104, 106, 108, 110, or 112.

BRIEF DESCRIPTION OF THE DRAWINGS AND SEQUENCE LISTING

The disclosure can be more fully understood from the following detailed description and the accompanying Sequence Listing which form a part of this application. The sequence descriptions and sequence listing attached here to comply with the rules governing nucleotide and amino acid sequence disclosures in patent applications as set forth in 37 C.F.R. §§ 1.821 and 1.825. The sequence descriptions comprise the three letter codes for amino acids as defined in 37 C.F.R. §§ 1.821 and 1.825, which are incorporated herein by reference.

TABLE 1

Sequence Listing Descriptions

| Source/Plant species | Clone Designation | SEQ ID NO: (Nucleotide) | SEQ ID NO: (Amino Acid) |
|---|---|---|---|
| Oryza sativa | OsCCP1 | 1, 2 | 3 |
| Oryza sativa | OsGPR89A | 4, 5 | 6 |
| Oryza sativa | OsDN-DTP13 | 7, 8 | 9 |
| Oryza sativa | OsCTPS1 | 10, 11 | 12 |
| Oryza sativa | OsDN-DTP14 | 13, 14 | 15 |
| Oryza sativa | OsLPA1 | 16, 17 | 18 |
| Oryza sativa | OsPE1 | 19, 20 | 21 |
| Oryza sativa | OsDN-DTP15 | 22, 23 | 24 |
| Oryza sativa | OsDN-DTP16 | 25, 26 | 27 |
| Oryza sativa | OsCAS2 | 28, 29 | 30 |
| Artificial | Gene Cloning Primers | 31-50 | n/a |
| Artificial | RT-PCR Primers | 51-52 | n/a |
| Oryza sativa | CCP1 paralog | 53 | 54 |
| Zea mays | CCP1 homolog | 55 | 56 |
| Sorghum bicolor | CCP1 homolog | 57 | 58 |
| Arabidopsis thaliana | CCP1 homolog | 59 | 60 |
| Glycine max | CCP1 homolog | 61 | 62 |
| Zea mays | GPR89A homolog | 63 | 64 |
| Sorghum bicolor | GPR89A homolog | 65 | 66 |
| Arabidopsis thaliana | GPR89A homolog | 67 | 68 |
| Glycine max | GPR89A homolog | 69 | 70 |
| Oryza sativa | DN-DTP13 paralog | 71 | 72 |
| Oryza sativa | CTPS1 paralog | 73 | 74 |
| Zea mays | CTPS1 homolog | 75 | 76 |
| Sorghum bicolor | CTPS1 homolog | 77 | 78 |
| Arabidopsis thaliana | CTPS1 homolog | 79 | 80 |
| Glycine max | CTPS1 homolog | 81 | 82 |
| Oryza sativa | LPA1 paralog | 83 | 84 |
| Zea mays | LPA1 homolog | 85 | 86 |
| Sorghum bicolor | LPA1 homolog | 87 | 88 |
| Arabidopsis thaliana | LPA1 homolog | 89 | 90 |
| Glycine max | LPA1 homolog | 91 | 92 |

TABLE 1-continued

Sequence Listing Descriptions

| Source/Plant species | Clone Designation | SEQ ID NO: (Nucleotide) | SEQ ID NO: (Amino Acid) |
|---|---|---|---|
| Oryza sativa | PEI paralog | 93 | 94 |
| Zea mays | PEI homolog | 95 | 96 |
| Sorghum bicolor | PEI homolog | 97 | 98 |
| Arabidopsis thaliana | PEI homolog | 99 | 100 |
| Glycine max | PEI homolog | 101 | 102 |
| Oryza sativa | DN-DTP15 paralog | 103 | 104 |
| Oryza sativa | CAS2 paralog | 105 | 106 |
| Zea mays | CAS2 homolog | 107 | 108 |
| Sorghum bicolor | CAS2 homolog | 109 | 110 |
| Glycine max | CAS2 homolog | 111 | 112 |

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants; reference to "a cell" includes one or more cells and equivalents thereof known to those skilled in the art, and so forth.

Definitions

As used herein, "increased drought tolerance" of a plant refers to any measurable improvement in a physiological or physical characteristic, such as yield, as measured relative to a reference or control plant when grown under drought conditions. Typically, when a plant comprising a recombinant DNA construct or DNA modification in its genome exhibits increased drought tolerance relative to a reference or control plant, the reference or control plant does not comprise in its genome the recombinant DNA construct or DNA modification.

"Agronomic characteristic" is a measurable parameter including but not limited to: greenness, grain yield, growth rate, total biomass or rate of accumulation, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, salt tolerance, tiller number, panicle size, early seedling vigor and seedling emergence under low temperature stress.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

A "control", "control plant" or "control plant cell" or the like provides a reference point for measuring changes in phenotype of a subject plant or plant cell in which genetic alteration, such as transformation, has been affected as to a gene of interest. For example, a control plant may be a plant having the same genetic background as the subject plant except for the genetic alteration that resulted in the subject plant or cell.

"Plant" includes reference to whole plants, plant organs, plant tissues, seeds and plant cells and progeny of the same. Plant cells include, without limitation, cells from seeds, suspension cultures, embryos, meristematic regions, callus tissues, leaves, roots, shoots, gametophytes, sporophytes, pollen, and microspores.

"Progeny" comprises any subsequent generation of a plant.

"Modified plant" includes reference to a plant which comprises within its genome a heterologous polynucleotide or modified gene or promoter. For example, the heterologous polynucleotide is stably integrated within the genome such that the polynucleotide is passed on to successive generations. The heterologous polynucleotide may be integrated into the genome alone or as part of a recombinant DNA construct.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", and "nucleic acid fragment" are used interchangeably and refer to a polymer of RNA or DNA that is single- or double-stranded, optionally containing synthetic, non-natural or altered nucleotide bases. Nucleotides (usually found in their 5'-monophosphate form) are referred to by their single-letter designation as follows: "A" for adenylate or deoxyadenylate, "C" for cytidylate or deoxycytidylate, and "G" for guanylate or deoxyguanylate for RNA or DNA, respectively; "U" for uridylate; "T" for deoxythymidylate; "R" for purines (A or G); "Y" for pyrimidines (C or T); "K" for G or T; "H" for A or C or T; "I" for inosine; and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, and sulfation, gamma-carboxylation of glutamic acid residues, hydroxylation and ADP-ribosylation.

"Recombinant DNA construct" refers to a combination of nucleic acid fragments that are not normally found together in nature. Accordingly, a recombinant DNA construct may comprise regulatory elements and coding sequences that are derived from different sources, or regulatory elements and coding sequences derived from the same source, but arranged in a manner different than that normally found in nature.

"Regulatory elements" refer to nucleotide sequences located upstream (5' non-coding sequences), within, or downstream (3' non-coding sequences) of a coding sequence, and influencing the transcription, RNA processing or stability, or translation of the associated coding sequence. Regulatory elements may include, but are not limited to, promoters, translation leader sequences, introns, and polyadenylation recognition sequences. The terms "regulatory sequence" and "regulatory element" and "regulatory region" are used interchangeably herein.

"Promoter" refers to a nucleic acid fragment capable of controlling transcription of another nucleic acid fragment. "Promoter functional in a plant" is a promoter capable of controlling transcription of genes in plant cells whether its origin is from a plant cell or not. "Tissue-specific promoter" and "tissue-preferred promoter" refers to a promoter that is expressed predominantly but not necessarily exclusively in one tissue or organ, but that may also be expressed in one specific cell or cell type. "Developmentally regulated promoter" is a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

As used herein "increased", "increase", or the like refers to any detectable increase in an experimental group (e.g., plant with a DNA modification described herein) as compared to a control group (e.g., wild-type plant that does not comprise the DNA modification). Accordingly, increased expression of a protein comprises any detectable increase in the total level of the protein in a sample and can be determined using routine methods in the art such as, for example, Western blotting and ELISA.

As used herein, "yield" refers to the amount of agricultural production harvested per unit of land, and may include reference to bushels per acre or kilograms per mu of a crop at harvest, as adjusted for grain moisture (e.g., typically 15% for maize, 13.5% for rice). Grain moisture is measured in the grain at harvest. The adjusted test weight of grain is determined to be the weight in pounds per bushel or grams per plant, adjusted for grain moisture level at harvest.

As used herein, "sequence identity" or "identity" in the context of two polynucleotides or polypeptide sequences refer to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

As used herein, "percentage of sequence identity" is calculated by determining the number of positions at which the identical nucleic acid base or amino acid residue occurs in both sequences to yield the number of matched positions, dividing the number of matched positions by the total number of positions in the window of comparison, and multiplying the result by 100.

Unless stated otherwise, multiple alignments of the sequences provided herein are performed using the Clustal V method of alignment (Higgins and Sharp. (1989) *CABIOS.* 5:151-153) with the default parameters (GAP PENALTY=10, GAP LENGTH PENALTY=10). Default parameters for pairwise alignments and calculation of percent identity of amino acid sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Compositions:

A. Polynucleotides and Polypeptides

The present disclosure provides polynucleotides encoding the following polypeptides: CCP1 (cupin domain containing protein); GPR89 (GPR89A, putative); DN-DTP13 (Expressed protein); CTPS1 (CTP synthase, putative); DN-DTP14 (hypothetical protein); LPA1 (lipase, putative); PE1 (pectinesterase, putative); DN-DTP15 (expressed protein); DN-DTP16 (expressed protein); and CAS2 (cycloartenol synthase, putative).

One aspect of the disclosure provides a polynucleotide encoding a polypeptide comprising an amino acid sequence that is at least 80% identical (e.g. 81%, 82%, 83%, 84%, 85%, 86%, 87%, 88%, 89%, 90%, 91%, 92%, 93%, 94%, 95%, 96%, 97%, 98%, 99%, or 100%) to the amino acid sequence of any one of SEQ ID NO: 3, 6, 9, 12, 15, 18, 21, 24, 27, 30, 54, 56, 58, 60, 62, 64, 66, 68, 70, 72, 74, 76, 78, 80, 82, 84, 86, 88, 90, 92, 94, 96, 98, 100, 102, 104, 106, 108, 110, or 112.

"OsCCP1" refers to a rice polypeptide that confers drought tolerance phenotype when overexpressed. The OsCCP1 polypeptide (SEQ ID NO: 3) is encoded by the coding sequence (CDS) (SEQ ID NO: 2) or nucleotide sequence (SEQ ID NO: 1) at rice gene locus LOC_Os01g74480.1, which is annotated as "cupin domain containing protein, expressed" in TIGR. "CCP1 polypeptide" refers herein to the OsCCP1 polypeptide and its paralogs (e.g., SEQ ID NO: 54 encoded by SEQ ID NO: 53) or homologs from other organisms, such as maize (SEQ ID NO: 56 encoded by SEQ ID NO: 55), sorghum (SEQ ID NO: 58 encoded by SEQ ID NO: 57), *Arabidopsis* (SEQ ID NO: 60 encoded by SEQ ID NO: 59), or soybean (SEQ ID NO: 62 encoded by SEQ ID NO: 61).

"OsGPR89A" refers to a rice polypeptide that confers drought tolerance phenotype when overexpressed. The OsGPR89A polypeptide (SEQ ID NO: 6) is encoded by the coding sequence (CDS) (SEQ ID NO: 5) or nucleotide sequence (SEQ ID NO: 4) at rice gene locus LOC_Os04g51180.1, which is annotated as "GPR89A, putative, expressed" in TIGR. "GPR89A polypeptide" refers herein to the OsGPR89A polypeptide and its paralogs or homologs from other organisms, such as maize (SEQ ID NO: 64 encoded by SEQ ID NO: 63), sorghum (SEQ ID NO: 66 encoded by SEQ ID NO: 65), *Arabidopsis* (SEQ ID NO: 68 encoded by SEQ ID NO: 67), or soybean (SEQ ID NO: 70 encoded by SEQ ID NO: 69).

"OsDN-DTP13" refers to a rice polypeptide that confers drought tolerance phenotype when overexpressed. The OsDN-DTP13 polypeptide (SEQ ID NO: 9) is encoded by the coding sequence (CDS) (SEQ ID NO: 8) or nucleotide sequence (SEQ ID NO: 7) at rice gene locus LOC_Os09g39360.1, which is annotated as "expressed protein" in TIGR. "DN-DTP13 polypeptide" refers herein to the OsDN-DTP13 polypeptide and its paralogs (e.g., SEQ ID NO: 72 encoded by SEQ ID NO: 71) or homologs from other organisms.

"OsCTPS1" refers to a rice polypeptide that confers drought tolerance phenotype when overexpressed. The OsCTPS1 polypeptide (SEQ ID NO: 12) is encoded by the coding sequence (CDS) (SEQ ID NO: 11) or nucleotide sequence (SEQ ID NO: 10) at rice gene locus LOC_Os05g49770.1, which is annotated as "CTP synthase, putative, expressed" in TIGR. "CTPS1 polypeptide" refers herein to the OsCTPS1 polypeptide and its paralogs (e.g., SEQ ID NO: 74 encoded by SEQ ID NO: 73) or homologs from other organisms, such as maize (SEQ ID NO: 76 encoded by SEQ ID NO: 75), sorghum (SEQ ID NO: 78 encoded by SEQ ID NO: 77), *Arabidopsis* (SEQ ID NO: 80 encoded by SEQ ID NO: 79), or soybean (SEQ ID NO: 82 encoded by SEQ ID NO: 81).

"OsDN-DTP14" refers to a rice polypeptide that confers drought tolerance phenotype when overexpressed. The OsDN-DTP14 polypeptide (SEQ ID NO: 15) is encoded by the coding sequence (CDS) (SEQ ID NO: 14) or nucleotide sequence (SEQ ID NO: 13) at rice gene locus LOC_Os11g14690.1, which is annotated as "hypothetical protein" in TIGR. "DN-DTP14 polypeptide" refers herein to the OsDN-DTP14 polypeptide and its paralogs or homologs from other organisms.

"OsLPA1" refers to a rice polypeptide that confers drought tolerance phenotype when overexpressed. The OsLPA1 polypeptide (SEQ ID NO: 18) is encoded by the coding sequence (CDS) (SEQ ID NO: 17) or nucleotide sequence (SEQ ID NO: 16) at rice gene locus LOC_Os05g28150.1, which is annotated as "lipase, putative, expressed" in TIGR. "LPA1polypeptide" refers herein to the OsLPA1 polypeptide and its paralogs (e.g., SEQ ID NO: 84 encoded by SEQ ID NO: 83) or homologs from other organisms, such as maize (SEQ ID NO: 86 encoded by SEQ ID NO: 85), sorghum (SEQ ID NO: 88 encoded by SEQ ID NO: 87), *Arabidopsis* (SEQ ID NO: 90 encoded by SEQ ID NO: 89), or soybean (SEQ ID NO: 92 encoded by SEQ ID NO: 91).

"OsPE1" refers to a rice polypeptide that confers drought tolerance phenotype when overexpressed. The OsPE1 polypeptide (SEQ ID NO: 21) is encoded by the coding sequence (CDS) (SEQ ID NO: 20) or nucleotide sequence (SEQ ID NO: 19) at rice gene locus LOC_Os01g19440.1, which is annotated as "pectinesterase, putative, expressed" in TIGR. "PE1 polypeptide" refers herein to the OsPE1 polypeptide and its paralogs (e.g., SEQ ID NO: 94 encoded by SEQ ID NO: 93) or homologs from other organisms, such as maize (SEQ ID NO: 96 encoded by SEQ ID NO: 95), sorghum (SEQ ID NO: 98 encoded by SEQ ID NO: 97), *Arabidopsis* (SEQ ID NO: 100 encoded by SEQ ID NO: 99), or soybean (SEQ ID NO: 102 encoded by SEQ ID NO: 101).

"OsDN-DTP15" refers to a rice polypeptide that confers drought tolerance phenotype when overexpressed. The OsDN-DTP15 polypeptide (SEQ ID NO: 24) is encoded by the coding sequence (CDS) (SEQ ID NO: 23) or nucleotide sequence (SEQ ID NO: 22) at rice gene locus LOC_Os06g13780.1, which is annotated as "expressed protein" in TIGR. "DN-DTP15 polypeptide" refers herein to the OsDN-DTP15 polypeptide and its paralogs (e.g., SEQ ID NO: 104 encoded by SEQ ID NO: 103) or homologs from other organisms.

"OsDN-DTP16" refers to a rice polypeptide that confers drought tolerance phenotype when overexpressed. The OsDN-DTP16 polypeptide (SEQ ID NO: 27) is encoded by the coding sequence (CDS) (SEQ ID NO: 26) or nucleotide sequence (SEQ ID NO: 25) at rice gene locus LOC_Os04g20380.1, which is annotated as "expressed protein" in TIGR. "DN-DTP16 polypeptide" refers herein to the OsDN-DTP16 polypeptide and its paralogs or homologs from other organisms.

"OsCAS2" refers to a rice polypeptide that confers drought tolerance phenotype when overexpressed. The OsCAS2 polypeptide (SEQ ID NO: 30) is encoded by the coding sequence (CDS) (SEQ ID NO: 29) or nucleotide sequence (SEQ ID NO: 28) at rice gene locus LOC_Os02g04760.1, which is annotated as "cycloartenol synthase, putative, expressed" in TIGR. "CAS2 polypeptide" refers herein to the OsCAS2 polypeptide and its paralogs (e.g., SEQ ID NO: 106 encoded by SEQ ID NO: 105) or homologs from other organisms, such as maize (SEQ ID NO: 108 encoded by SEQ ID NO: 107), sorghum (SEQ ID NO: 110 encoded by SEQ ID NO: 109), or soybean (SEQ ID NO: 112 encoded by SEQ ID NO: 111).

It is understood, as those skilled in the art will appreciate, that the disclosure encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

B. Recombinant DNA Constructs

Also provided are recombinant DNA constructs comprising any of the polynucleotides described herein. In certain embodiments, the recombinant DNA construct further comprises at least one regulatory element. In certain embodiments the at least one regulatory element is a heterologous regulatory element. In certain embodiments, the at least one regulatory element of the recombinant DNA construct comprises a promoter. In certain embodiments, the promoter is a heterologous promoter.

A number of promoters can be used in recombinant DNA constructs of the present disclosure. The promoters can be selected based on the desired outcome, and may include constitutive, tissue-specific, inducible, or other promoters for expression in the host organism.

A "constitutive" promoter is a promoter, which is active under most environmental conditions. Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810-812); rice actin (McElroy et al. (1990) Plant Cell 2:163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

A tissue-specific or developmentally-regulated promoter is a DNA sequence which regulates the expression of a DNA sequence selectively in the cells/tissues of a plant, such as in those cells/tissues critical to tassel development, seed set, or both, and which usually limits the expression of such a DNA sequence to the developmental period of interest (e.g. tassel development or seed maturation) in the plant. Any identifiable promoter which causes the desired temporal and spatial expression may be used in the methods of the present disclosure.

Many leaf-preferred promoters are known in the art (Yamamoto et al. (1997) Plant J. 12(2):255-265; Kwon et al. (1994) Plant Physiol. 105:357-367; Yamamoto et al. (1994) Plant Cell Physiol. 35(5):773-778; Gotor et al. (1993) Plant J. 3:509-518; Orozco et al. (1993) Plant Mol. Biol. 23(6): 1129-1138; and Matsuoka et al. (1993) Proc. Natl. Acad. Sci. USA 90(20):9586-9590).

Promoters which are seed or embryo-specific and may be useful in the disclosure include soybean Kunitz trypsin inhibitor (Kti3, Jofuku and Goldberg. (1989) Plant Cell 1:1079-1093), convicilin, vicilin, and legumin (pea cotyledons) (Rerie, W. G., et al. (1991) Mol. Gen. Genet. 259: 149-157; Newbigin, E. J., et al. (1990) Planta 180:461-470; Higgins, T. J. V., et al. (1988) Plant. Mol. Biol. 11:683-695), zein (maize endosperm) (Schemthaner, J. P., et al. (1988) EMBO J. 7:1249-1255), phaseolin (bean cotyledon) (Segupta-Gopalan, C., et al. (1985) Proc. Natl. Acad. Sci. 82:3320-3324), phytohemagglutinin (bean cotyledon) (Voelker, T. et al. (1987) EMBO J. 6:3571-3577), B-conglycinin and glycinin (soybean cotyledon) (Chen, Z-L, et al. (1988) EMBO J. 7:297-302), glutelin (rice endosperm), hordein (barley endosperm) (Marris, C., et al. (1988) Plant Mol. Biol. 10:359-366), glutenin and gliadin (wheat endosperm) (Colot, V., et al. (1987) EMBO J. 6:3559-3564). Promoters of seed-specific genes operably linked to heterologous coding regions in chimeric gene constructions maintain their temporal and spatial expression pattern in transgenic plants. Such examples include Arabidopsis 2S seed storage protein gene promoter to express enkephalin peptides in Arabidopsis and Brassica napus seeds (Vanderkerckhove et al. (1989) Bio/Technology 7: L929-932), bean lectin and bean beta-phaseolin promoters to express luciferase (Riggs et al. (1989) Plant Sci. 63:47-57), and wheat glutenin promoters to express chloramphenicol acetyl transferase (Colot et al. (1987) EMBO J 6:3559-3564).

Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Also contemplated are synthetic promoters which include a combination of one or more heterologous regulatory elements.

The promoter of the recombinant DNA constructs of the invention can be any type or class of promoter known in the art, such that any one of a number of promoters can be used to express the various polynucleotide sequences disclosed herein, including the native promoter of the polynucleotide sequence of interest. The promoters for use in the recombinant DNA constructs of the invention can be selected based on the desired outcome.

The recombinant DNA constructs of the present disclosure may also include other regulatory elements, including but not limited to, translation leader sequences, introns, and polyadenylation recognition sequences. In certain embodiments, a recombinant DNA construct further comprises an enhancer or silencer.

An intron sequence can be added to the 5' untranslated region, the protein-coding region or the 3' untranslated region to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg. (1988) *Mol. Cell Biol.* 8:4395-4405; Callis et al. (1987) *Genes Dev.* 1:1183-1200).

C. Plants and Plant Cells

Provided are plants, plant cells, plant parts, seed and grain comprising in its genome any of the recombinant DNA constructs described herein, so that the plants, plant cells, plant parts, seed, and/or grain have increased expression of the encoded polypeptide.

Also provided are plants, plant cells, plant parts, seeds, and grain comprising an introduced genetic modification at a genomic locus that encodes a polypeptide comprising an amino acid sequence that is at least 80% identical to an amino acid sequence selected from the group consisting of SEQ ID NOs: 3, 6, 9, 12, 15, 18, 21, 24, 27, 30, 54, 56, 58, 60, 62, 64, 66, 68, 70, 72, 74, 76, 78, 80, 82, 84, 86, 88, 90, 92, 94, 96, 98, 100, 102, 104, 106, 108, 110, or 112. In certain embodiments, the genetic modification increases the activity of the encoded polypeptide. In certain embodiments, the genetic modification increases the level of the encoded polypeptide. In certain embodiments, the genetic modification increases both the level and activity of the encoded polypeptide.

The plant may be a monocotyledonous or dicotyledonous plant, for example, a rice or maize or soybean plant, such as a maize hybrid plant or a maize inbred plant. The plant may also be sunflower, sorghum, canola, wheat, alfalfa, cotton, barley, millet, sugar cane or switchgrass.

In certain embodiments the plant exhibits increased drought tolerance when compared to a control plant. In certain embodiments, the plant exhibits an alteration of at least one agronomic characteristic when compared to the control plant.

One of ordinary skill in the art is familiar with protocols for simulating drought conditions and for evaluating drought tolerance of plants that have been subjected to simulated or naturally-occurring drought conditions. For example, one can simulate drought conditions by giving plants less water than normally required or no water over a period of time, and one can evaluate drought tolerance by looking for differences in physiological and/or physical condition, including (but not limited to) vigor, growth, size, or root length, or in particular, leaf color or leaf area size. Other techniques for evaluating drought tolerance include measuring chlorophyll fluorescence, photosynthetic rates and gas exchange rates.

D. Stacking with Other Traits of Interest

In some embodiments, the inventive polynucleotides disclosed herein are engineered into a molecular stack. Thus, the various host cells, plants, plant cells, plant parts, seeds, and/or grain disclosed herein can further comprise one or more traits of interest. In certain embodiments, the host cell, plant, plant part, plant cell, seed, and/or grain is stacked with any combination of polynucleotide sequences of interest in order to create plants with a desired combination of traits. As used herein, the term "stacked" refers to having multiple traits present in the same plant or organism of interest. For example, "stacked traits" may comprise a molecular stack where the sequences are physically adjacent to each other. A trait, as used herein, refers to the phenotype derived from a particular sequence or groups of sequences. In one embodiment, the molecular stack comprises at least one polynucleotide that confers tolerance to glyphosate. Polynucleotides that confer glyphosate tolerance are known in the art.

In certain embodiments, the molecular stack comprises at least one polynucleotide that confers tolerance to glyphosate and at least one additional polynucleotide that confers tolerance to a second herbicide.

In certain embodiments, the plant, plant cell, seed, and/or grain having an inventive polynucleotide sequence may be stacked with, for example, one or more sequences that confer tolerance to: an ALS inhibitor; an HPPD inhibitor; 2,4-D; other phenoxy auxin herbicides; aryloxyphenoxypropionate herbicides; dicamba; glufosinate herbicides; herbicides which target the protox enzyme (also referred to as "protox inhibitors").

The plant, plant cell, plant part, seed, and/or grain having an inventive polynucleotide sequence can also be combined with at least one other trait to produce plants that further comprise a variety of desired trait combinations. For instance, the plant, plant cell, plant part, seed, and/or grain having an inventive polynucleotide sequence may be stacked with polynucleotides encoding polypeptides having pesticidal and/or insecticidal activity, or a plant, plant cell, plant part, seed, and/or grain having an inventive polynucleotide sequence may be combined with a plant disease resistance gene.

These stacked combinations can be created by any method including, but not limited to, breeding plants by any conventional methodology, or genetic transformation. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/

25840, WO99/25855, and WO99/25853, all of which are herein incorporated by reference.

Methods

Provided is a method for increasing drought tolerance and/or increasing grain yield, in a plant, comprising increasing the expression of at least one polynucleotide encoding a polypeptide with amino acid sequence of at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) sequence identity to SEQ ID NO: 3, 6, 9, 12, 15, 18, 21, 24, 27, 30, 54, 56, 58, 60, 62, 64, 66, 68, 70, 72, 74, 76, 78, 80, 82, 84, 86, 88, 90, 92, 94, 96, 98, 100, 102, 104, 106, 108, 110, or 112.

In certain embodiments, the method comprises: (a) expressing in a regenerable plant cell a recombinant DNA construct comprising a regulatory element operably linked to the polynucleotide encoding the polypeptide; and (b) generating the plant, wherein the plant comprises in its genome the recombinant DNA construct. In certain embodiments the regulatory element is a heterologous promoter.

In certain embodiments, the method comprises: (a) introducing in a regenerable plant cell a targeted genetic modification at a genomic locus that encodes the polypeptide; and (b) generating the plant, wherein the level and/or activity of the encoded polypeptide is increased in the plant. In certain embodiments the targeted genetic modification is introduced using a genome modification technique selected from the group consisting of a polynucleotide-guided endonuclease, CRISPR-Cas endonucleases, base editing deaminases, a zinc finger nuclease, a transcription activator-like effector nuclease (TALEN), engineered site-specific meganucleases, or Argonaute. In certain embodiments, the targeted genetic modification is present in (a) the coding region; (b) a non-coding region; (c) a regulatory sequence; (d) an untranslated region; or (e) any combination of (a)-(d) of the genomic locus that encodes a polypeptide comprising an amino acid sequence that is at least 80% identical to an amino acid sequence selected from the group consisting of SEQ ID NOs: 3, 6, 9, 12, 15, 18, 21, 24, 27, 30, 54, 56, 58, 60, 62, 64, 66, 68, 70, 72, 74, 76, 78, 80, 82, 84, 86, 88, 90, 92, 94, 96, 98, 100, 102, 104, 106, 108, 110, or 112.

In certain embodiments the DNA modification is an insertion of one or more nucleotides, preferably contiguous, in the genomic locus. For example, the insertion of an expression modulating element (EME), such as an EME described in PCT/US2018/025446, in operable linkage with the gene. In certain embodiments, the targeted DNA modification may be the replacement of the endogenous polypeptide promoter with another promoter known in the art to have higher expression. In certain embodiments, the targeted DNA modification may be the insertion of a promoter known in the art to have higher expression into the 5'UTR so that expression of the endogenous polypeptide is controlled by the inserted promoter. In certain embodiments, the DNA modification is a modification to optimize Kozak context to increase expression. In certain embodiments, the DNA modification is a polynucleotide modification or SNP at a site that regulates the stability of the expressed protein.

The plant for use in the inventive methods can be any plant species described herein. In certain embodiments, the plant is maize, soybean, or rice.

Various methods can be used to introduce a sequence of interest into a plant, plant part, plant cell, seed, and/or grain. "Introducing" is intended to mean presenting to the plant, plant cell, seed, and/or grain the inventive polynucleotide or resulting polypeptide in such a manner that the sequence gains access to the interior of a cell of the plant. The methods of the disclosure do not depend on a particular method for introducing a sequence into a plant, plant cell, seed, and/or grain, only that the polynucleotide or polypeptide gains access to the interior of at least one cell of the plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055 and 5,981,840), direct gene transfer (Paszkowski et al. (1984) *EMBO J.* 3:2717-2722), and ballistic particle acceleration (see, for example, U.S. Pat. Nos. 4,945,050; 5,879,918; 5,886,244; and, 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In other embodiments, the inventive polynucleotides disclosed herein may be introduced into plants by contacting plants with a virus or viral nucleic acids. Generally, such methods involve incorporating a nucleotide construct of the disclosure within a DNA or RNA molecule. It is recognized that the inventive polynucleotide sequence may be initially synthesized as part of a viral polyprotein, which later may be processed by proteolysis in vivo or in vitro to produce the desired recombinant protein. Further, it is recognized that promoters disclosed herein also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present disclosure provides transformed seed (also referred to as "transgenic seed") having a polynucleotide disclosed herein, for example, as part of an expression cassette, stably incorporated into their genome.

Transformed plant cells which are derived by plant transformation techniques, including those discussed above, can be cultured to regenerate a whole plant which possesses the transformed genotype (i.e., an inventive polynucleotide), and thus the desired phenotype, such as increased yield. For transformation and regeneration of maize see, Gordon-Kamm et al., *The Plant Cell,* 2:603-618 (1990).

Various methods can be used to introduce a genetic modification at a genomic locus that encodes a polypeptide disclosed herein into the plant, plant part, plant cell, seed, and/or grain. In certain embodiments the targeted DNA modification is through a genome modification technique selected from the group consisting of a polynucleotide-guided endonuclease, CRISPR-Cas endonucleases, base editing deaminases, zinc finger nuclease, a transcription activator-like effector nuclease (TALEN), engineered site-specific meganuclease, or Argonaute.

In some embodiments, the genome modification may be facilitated through the induction of a double-stranded break (DSB) or single-strand break, in a defined position in the genome near the desired alteration. DSBs can be induced using any DSB-inducing agent available, including, but not limited to, TALENs, meganucleases, zinc finger nucleases, Cas9-gRNA systems (based on bacterial CRISPR-Cas systems), guided cpf1 endonuclease systems, and the like. In some embodiments, the introduction of a DSB can be combined with the introduction of a polynucleotide modification template.

A polynucleotide modification template can be introduced into a cell by any method known in the art, such as, but not limited to, transient introduction methods, transfection, electroporation, microinjection, particle mediated delivery, topical application, whiskers mediated delivery, delivery via cell-penetrating peptides, or mesoporous silica nanoparticle (MSN)-mediated direct delivery.

The polynucleotide modification template can be introduced into a cell as a single stranded polynucleotide molecule, a double stranded polynucleotide molecule, or as part of a circular DNA (vector DNA). The polynucleotide modification template can also be tethered to the guide RNA and/or the Cas endonuclease.

A "modified nucleotide" or "edited nucleotide" refers to a nucleotide sequence of interest that comprises at least one alteration when compared to its non-modified nucleotide sequence. Such "alterations" include, for example: (i) replacement of at least one nucleotide, (ii) a deletion of at least one nucleotide, (iii) an insertion of at least one nucleotide, or (iv) any combination of (i)-(iii).

The term "polynucleotide modification template" includes a polynucleotide that comprises at least one nucleotide modification when compared to the nucleotide sequence to be edited. A nucleotide modification can be at least one nucleotide substitution, addition or deletion. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

The process for editing a genomic sequence combining DSB and modification templates generally comprises: providing to a host cell, a DSB-inducing agent, or a nucleic acid encoding a DSB-inducing agent, that recognizes a target sequence in the chromosomal sequence and is able to induce a DSB in the genomic sequence, and at least one polynucleotide modification template comprising at least one nucleotide alteration when compared to the nucleotide sequence to be edited. The polynucleotide modification template can further comprise nucleotide sequences flanking the at least one nucleotide alteration, in which the flanking sequences are substantially homologous to the chromosomal region flanking the DSB.

The endonuclease can be provided to a cell by any method known in the art, for example, but not limited to, transient introduction methods, transfection, microinjection, and/or topical application or indirectly via recombination constructs. The endonuclease can be provided as a protein or as a guided polynucleotide complex directly to a cell or indirectly via recombination constructs. The endonuclease can be introduced into a cell transiently or can be incorporated into the genome of the host cell using any method known in the art. In the case of a CRISPR-Cas system, uptake of the endonuclease and/or the guided polynucleotide into the cell can be facilitated with a Cell Penetrating Peptide (CPP) as described in WO2016073433 published May 12, 2016.

In addition to modification by a double strand break technology, modification of one or more bases without such double strand break are achieved using base editing technology, see e.g., Gaudelli et al., (2017) Programmable base editing of A*T to G*C in genomic DNA without DNA cleavage. Nature 551(7681):464-471; Komor et al., (2016) Programmable editing of a target base in genomic DNA without double-stranded DNA cleavage, Nature 533(7603): 420-4.

These fusions contain dCas9 or Cas9 nickase and a suitable deaminase, and they can convert e.g., cytosine to uracil without inducing double-strand break of the target DNA. Uracil is then converted to thymine through DNA replication or repair. Improved base editors that have targeting flexibility and specificity are used to edit endogenous locus to create target variations and improve grain yield. Similarly, adenine base editors enable adenine to inosine change, which is then converted to guanine through repair or replication. Thus, targeted base changes i.e., C·G to T·A conversion and A·T to G·C conversion at one more location made using appropriate site-specific base editors.

In an embodiment, base editing is a genome editing method that enables direct conversion of one base pair to another at a target genomic locus without requiring double-stranded DNA breaks (DSBs), homology-directed repair (HDR) processes, or external donor DNA templates. In an embodiment, base editors include (i) a catalytically impaired CRISPR-Cas9 mutant that are mutated such that one of their nuclease domains cannot make DSBs; (ii) a single-strand-specific cytidine/adenine deaminase that converts C to U or A to G within an appropriate nucleotide window in the single-stranded DNA bubble created by Cas9; (iii) a uracil glycosylase inhibitor (UGI) that impedes uracil excision and downstream processes that decrease base editing efficiency and product purity; and (iv) nickase activity to cleave the non-edited DNA strand, followed by cellular DNA repair processes to replace the G-containing DNA strand.

As used herein, a "genomic region" is a segment of a chromosome in the genome of a cell that is present on either side of the target site or, alternatively, also comprises a portion of the target site. The genomic region can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800. 5-2900, 5-3000, 5-3100 or more bases such that the genomic region has sufficient homology to undergo homologous recombination with the corresponding region of homology.

TAL effector nucleases (TALEN) are a class of sequence-specific nucleases that can be used to make double-strand breaks at specific target sequences in the genome of a plant or other organism (Miller et al. (2011) Nature Biotechnology 29:143-148).

Endonucleases are enzymes that cleave the phosphodiester bond within a polynucleotide chain. Endonucleases include restriction endonucleases, which cleave DNA at specific sites without damaging the bases, and meganucleases, also known as homing endonucleases (HEases), which like restriction endonucleases, bind and cut at a specific recognition site, however the recognition sites for meganucleases are typically longer, about 18 bp or more (patent application PCT/US12/30061, filed on Mar. 22, 2012). Meganucleases have been classified into four families based on conserved sequence motifs, the families are the LAGLI-DADG, GIY-YIG, H-N-H, and His-Cys box families. These motifs participate in the coordination of metal ions and hydrolysis of phosphodiester bonds. HEases are notable for their long recognition sites, and for tolerating some sequence polymorphisms in their DNA substrates. The naming convention for meganuclease is similar to the convention for other restriction endonuclease. Meganucleases are also characterized by prefix F-, I-, or PI- for enzymes encoded by free-standing ORFs, introns, and inteins, respectively. One step in the recombination process involves polynucleotide cleavage at or near the recognition site. The cleaving activity can be used to produce a double-strand break. For reviews of site-specific recombinases and their recognition sites, see, Sauer (1994) Curr Op Biotechnol 5:521-7; and Sadowski (1993) FASEB 7:760-7. In some examples the recombinase is from the Integrase or Resolvase families.

Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs include an engineered DNA-binding zinc finger domain linked to a non-specific endonuclease domain, for example nuclease domain from a Type IIs endonuclease such as FokI. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3-finger domain recognized a sequence of 9 contiguous nucleotides, with a dimerization requirement of the nuclease, two sets of zinc finger triplets are used to bind an 18 nucleotide recognition sequence.

Genome editing using DSB-inducing agents, such as Cas9-gRNA complexes, has been described, for example in U.S. Patent Application US 2015-0082478 A1, published on Mar. 19, 2015, WO2015/026886 A1, published on Feb. 26, 2015, WO2016007347, published on Jan. 14, 2016, and WO201625131, published on Feb. 18, 2016, all of which are incorporated by reference herein.

EXAMPLES

The following are examples of specific embodiments of some aspects of the invention. The examples are offered for illustrative purposes only and are not intended to limit the scope of the invention in any way.

Example 1

Cloning and Vector Construction of Drought Tolerance Genes

A binary construct that contains four multimerized enhancers elements derived from the Cauliflower Mosaic Virus 35S (CaMV 35S) promoter was used, and the rice activation tagging population was developed from four Japonica (*Oryza sativa* ssp. *Japonica*) varieties (Zhonghua 11, Chaoyou 1, Taizhong 65 and Nipponbare), which were transformed by Agrobacteria-mediated transformation method as described by Lin and Zhang ((2005) *Plant Cell Rep.* 23:540-547). The transgenic lines generated were developed and the transgenic seeds were harvested to form the rice activation tagging population.

Drought tolerance tagging lines (ATLs) were confirmed in repeated field experiments and their T-DNA insertion loci were determined. The T-DNA insertion loci in the ATLs were determined by Southern-by-Sequencing method (Zastrow-Hayes G. M. et al. (2015), The Plant Genome, 8:1-15). The genes near by the left border and right border of the T-DNA were cloned and the functional genes were recapitulated by field screens. Only the recapitulated functional genes are showed herein. Based on LOC IDs and the corresponding gene sequences of these genes shown in Table 2, primers were designed for cloning the rice drought tolerance genes OsCCP1, OsGPR89A, OsDN-DTP13, OsCTPS1, OsDN-DTP14, OsLPA1, OsPE1, OsDN-DTP15, OsDN-DTP16, and OsCAS2.

TABLE 2

Rice gene names, Gene IDs (from TIGR) and Construct IDs

| Gene name | LOC ID | Construct ID |
|---|---|---|
| OsCCP1 | LOC_Os01g74480.1 | DP0927 |
| OsGPR89A | LOC_Os04g51180.1 | DP1545 |
| OsDN-DTP13 | LOC_Os09g39360.1 | DP1013 |
| OsCTPS1 | LOC_Os05g49770.1 | DP2283 |
| OsDN-DTP14 | LOC_Os11g14690.1 | DP1539 |
| OsLPA1 | LOC_Os05g28150.1 | DP1408 |
| OsPE1 | LOC_Os01g19440.1 | DP0921 |
| OsDN-DTP15 | LOC_Os06g13780.1 | DP1410 |
| OsDN-DTP16 | LOC_Os04g20380.1 | DP2220 |
| OsCAS2 | LOC_Os02g04760.1 | DP1110 |

PCR amplified products were extracted after the agarose gel electrophoresis using a column kit and then ligated with TA cloning vectors. The sequences and orientation in these constructs were confirmed by sequencing. Each gene was cloned into a plant binary construct.

Example 2

Transformation and Gene Expression Analysis of Transgenic Rice Lines

Zhonghua 11 (*Oryza sativa* L.) were transformed with either a vector prepared in Example 1 or an empty vector (DP0158) by Agrobacteria-mediated transformation as described by Lin and Zhang ((2005) *Plant Cell Rep.* 23:540-547). Transgenic seedlings ($T_0$) generated in the transformation laboratory were transplanted in field to get $T_1$ seeds. The $T_1$ and subsequent $T_2$ seeds were screened to confirm transformation and positively identified transgenic seeds were used in the following trait screens.

The gene expression levels in the leaves of the transgenic rice plants were determined by RT-PCR. Primers were designed for the RT-PCR for OsLPA1 gene in the overexpression transgenic rice. The level of expression in ZH11-TC (tissue cultured ZH11 rice) was set at 1.00, and the expression levels in the DP1408-transgenic rice plants were compared to ZH11-TC. Gene expression was normalized based on the EF-1α mRNA levels, and the results from the gene expression analysis are provided in Table 3 below.

TABLE 3

Relative Expression Level Fold Increase in Transgenic Rice Plants

| Gene name | Construct ID | Relative Expression Level Fold Increase |
|---|---|---|
| OsLPA1 | DP1408 | From 49.34 to 9656.49 |

Example 3

Characterization of the Transgenic Rice Plants

The transgenic rice plants from Example 2 and ZH11-TC and DP0158 rice plants were tested for drought tolerance.

$T_2$ seeds from the plants of Example 2 were sterilized by 800 ppm carbendazol for 8 hours at 32° C. and washed 3-5 time, soaked in water for 16 hours at 32° C., and germinated for 18 hours at 35-37° C. in an incubator. Germinated seeds were used as follows for the drought tolerance test.

Drought tolerance assay—The germinated seeds were planted in a seedbed field. At 3-leaf stage, the seedlings were transplanted into the testing field with 4 replicates and 10 plants per replicate for each transgenic line, and the 4 replicates were planted in the same block. ZH11-TC and DP0158 seedlings were nearby the transgenic lines in the same block, and were used as controls in the statistical analysis. The rice plants were managed by normal practice using pesticides and fertilizers. Watering was stopped at the panicle initiation stage, so as to give drought stress at flowering stage depending on the weather conditions (temperature and humidity). The soil water content was measured every 4 days at about 10 sites per block using TDR30 (Spectrum Technologies, Inc.). Plant phenotypes were observed and recorded during the experiments. The phenotypes include heading date, leaf rolling degree, drought sensitivity and drought tolerance. Special attention was paid to leaf rolling degree at noontime. At the end of the growing season, six representative plants of each transgenic line were harvested from the middle of the row per line, and grain yield per plant was measured. The grain yield data were statistically analyzed using mixed linear model.

The results from these studies are provided in Table 4, which provides the combined data of the transgenic lines for each of the constructs.

TABLE 4

Agronomic Characteristics of the Transgenic Rice Plants

| No | Construct ID | Avg. yield per plant under field drought conditions (g/plant) |
|---|---|---|
| 1 | ZH11-TC | 4.96 ± 0.87 |
|   | DP0158 | 4.92 ± 0.87 |
|   | DP0927 | 7.33 ± 0.73 [a, b] |
| 2 | ZH11-TC | 6.11 ± 0.34 |
|   | DP0158 | 4.02 ± 0.34 |
|   | DP1545 | 7.07 ± 0.32 [a, b] |
| 3 | ZH11-TC | 7.23 ± 1.08 |
|   | DP0158 | 6.38 ± 1.08 |
|   | DP1013 | 9.83 ± 0.83 [a, b] |
| 4 | ZH11-TC | 9.40 ± 2.44 |
|   | DP0158 | 10.04 ± 2.47 |
|   | DP2283 | 15.06 ± 2.14 [a, b] |
| 5 | ZH11-TC | 6.14 ± 0.87 |
|   | DP0158 | 5.32 ± 0.87 |
|   | DP1539 | 9.20 ± 0.85 [a, b] |
| 6 | ZH11-TC | 3.67 ± 0.91 |
|   | DP0158 | 3.10 ± 1.00 |
|   | DP1408 | 5.07 ± 0.70 [b] |
| 7 | ZH11-TC | 3.42 ± 0.76 |
|   | DP0158 | 3.47 ± 0.85 |
|   | DP0921 | 5.31 ± 0.69 [a, b] |
| 8 | ZH11-TC | 4.51 ± 0.97 |
|   | DP0158 | 4.54 ± 0.97 |
|   | DP1410 | 6.51 ± 0.73 [a, b] |
| 9 | ZH11-TC | 2.00 ± 0.49 |
|   | DP0158 | 2.24 ± 0.36 |
|   | DP2220 | 3.02 ± 0.33 [a, b] |
| 10 | ZH11-TC | 3.10 ± 1.00 |
|   | DP0158 | 3.22 ± 0.54 |
|   | DP1110 | 4.45 ± 0.43 [a, b] |

[a] $P \leq 0.1$ compared to ZH11-TC control;
[b] $P \leq 0.1$ compared to DP0158 control.

DP0927-transgenic rice plants were tested two times in Hainan field in two years. The results consistently showed that the average yield per plant of DP0927-transgenic rice increased under field drought conditions compared to the controls. As shown in Table 4, twelve lines were tested, and two lines observed good seed setting rate in Hainan field. Six lines showed a significant increase (P<0.1) in yield as compared to the yield of the ZH11-TC and DP0158 controls. The average yield per plant of these 12 lines is 48% and 49% higher than that of ZH11-TC and DP0158 controls, respectively. These data show that OsCCP1 is a rice drought tolerance gene.

DP1545-transgenic rice plants were tested two times in Hainan field in two years. The results consistently showed that the average yield per plant of DP1545-transgenic rice increased under field drought conditions compared to the controls. As shown in Table 4, ten lines were tested, and six lines observed good seed setting rate in Hainan field. Ten lines showed a significant increase (P<0.1) in yield as compared to the yield of the DP0158 control, and six lines showed a significant increase in yield as compared to the yield of the ZH11-TC control. The average yield per plant of these 10 lines is 16% and 76% higher than that of ZH11-TC and DP0158 controls, respectively. These data show that OsGPR89A is a rice drought tolerance gene.

DP1013-transgenic rice plants were tested two times in Hainan field in two years. The results consistently showed that the average yield per plant of DP1013-transgenic rice increased under field drought conditions compared to the controls. As shown in Table 4, twelve lines were tested, and three lines observed good seed setting rate in Hainan field. Seven lines showed a significant increase (P<0.1) in yield as compared to the yield of the DP0158 control, and six lines showed a significant increase in yield as compared to the yield of the ZH11-TC control. The average yield per plant of these 12 lines is 36% and 54% higher than that of ZH11-TC and DP0158 controls, respectively. These results demonstrate that OsDN-DTP13 transgenic rice plants had enhanced drought tolerance compared to both controls.

DP2283-transgenic rice plants were tested in Hainan and Ningxia field in two years. The results consistently showed that the average yield per plant of DP2283-transgenic rice increased under field drought conditions compared to the controls. As shown in Table 4, eight lines were tested, and five lines observed good seed setting rate in Ningxia field. Five lines showed a significant increase (P<0.1) in yield as compared to the yield of the DP0158 control, and four lines showed a significant increase in yield as compared to the yield of the ZH11-TC control. The average yield per plant of these 8 lines is 113% and 55% higher than that of ZH11-TC and DP0158 controls, respectively. These data show that OsCTPS1 is a rice drought tolerance gene.

DP1539-transgenic rice plants were tested in Hainan and Ningxia field in two years. The results consistently showed that the average yield per plant of DP1539-transgenic rice increased under field drought conditions compared to the controls. As shown in Table 4, twelve lines were tested, and two lines observed good seed setting rate in Ningxia field. Eleven lines showed a significant increase (P<0.1) in yield as compared to the yield of the DP0158 control, and seven lines showed a significant increase in yield as compared to the yield of the ZH11-TC control. The average yield per plant of these 12 lines is 50% and 73% higher than that of ZH11-TC and DP0158 controls, respectively. These data show that OsDN-DTP14 is a rice drought tolerance gene.

DP1408-transgenic rice plants were tested two times in Hainan and Ningxia field in two years. All of them showed that the average yield per plant of DP1408-transgenic rice increased under field drought conditions compared to the controls. As shown in Table 4, eight lines were tested, and one lines observed good seed setting rate in Hainan field. Seven lines showed a significant increase (P<0.1) in yield as compared to the yield of the DP0158 control, and one line showed a significant increase in yield as compared to the yield of the ZH11-TC control. The average yield per plant of these 8 lines is 38% and 64% higher than that of ZH11-TC and DP0158 controls, respectively. These data show that OsLPA1 is a rice drought tolerance gene.

DP0921-transgenic rice plants were tested two times in Hainan field in two years. The results consistently that the average yield per plant of DP0921-transgenic rice increased under field drought conditions compared to the controls. As shown in Table 4, twelve lines were tested, seven lines showed a significant increase (P<0.1) in yield as compared to the yield of the DP0158 control, and six lines showed a significant increase in yield as compared to the yield of the ZH11-TC control. The average yield per plant of these 12 lines is 55% and 53% higher than that of ZH11-TC and DP0158 controls, respectively. These data show that OsPE1 is a rice drought tolerance gene.

DP1410-transgenic rice plants were tested two times in Hainan field in two years. The results consistently showed that the average yield per plant of DP1410-transgenic rice increased under field drought conditions compared to the controls. As shown in Table 4, eight lines were tested, and four lines observed good seed setting rate in Hainan field. Seven lines showed a significant increase (P<0.1) in yield as compared to the yield of the DP0158 control, and seven lines showed a significant increase in yield as compared to the yield of the ZH11-TC control. The average yield per plant of these 8 lines is 44% and 43% higher than that of ZH11-TC and DP0158 controls, respectively. These data show that OsDN-DTP15 is a rice drought tolerance gene.

DP2220-transgenic rice plants were tested two times in Hainan field in two years. The results consistently showed that the average yield per plant of DP2220-transgenic rice increased under field drought conditions compared to the controls. As shown in Table 4, eight lines were tested, and four lines observed good seed setting rate in Hainan field. Three lines showed a significant increase (P<0.1) in yield as compared to the yield of the DP0158 control, and three lines showed a significant increase in yield as compared to the yield of the ZH11-TC control. The average yield per plant of these 8 lines is 51% and 35% higher than that of ZH11-TC and DP0158 controls, respectively. These data show that OsDN-DTP16 is a rice drought tolerance gene.

DP1110-transgenic rice plants were tested two times in Hainan field in two years. The results consistently showed that the average yield per plant of DP1110-transgenic rice increased under field drought conditions compared to the controls. As shown in Table 4, twelve lines were tested, and five lines observed good seed setting rate in Hainan field. Six lines showed a significant increase (P<0.1) in yield as compared to the yield of the DP0158 control, and six lines showed a significant increase in yield as compared to the yield of the ZH11-TC control. The average yield per plant of these 12 lines is 44% and 38% higher than that of ZH11-TC and DP0158 controls, respectively. These data show that OsCAS2 is a rice drought tolerance gene.

Taken together, these results indicate that OsCCP1, OsGPR89A, OsDN-DTP13, OsCTPS1, OsDN-DTP14, OsLPA1, OsPE1, OsDN-DTP15, OsDN-DTP16 and OsCAS2 transgenic rice plants have increased tolerance to drought stress compared to control plants under field conditions.

Example 4

Transformation and Evaluation of Maize with Rice Drought Tolerance Genes

Maize plants will be transformed with one of the polynucleotides encoding the polypeptides described herein or a corresponding homolog from maize, *Arabidopsis*, or other species. Expression of the gene in the maize transformation vector can be under control of a constitutive promoter such as the maize ubiquitin promoter (Christensen et al. (1989) *Plant Mol. Biol.* 12:619-632 and Christensen et al. (1992) *Plant Mol. Biol.* 18:675-689) or under control of another promoter, such as a stress-responsive promoter or a tissue-preferred promoter. The recombinant DNA construct can be introduced into maize cells by particle bombardment substantially as described in International Patent Publication WO 2009/006276. Alternatively, maize plants can be transformed with the recombinant DNA construct by *Agrobacterium*-mediated transformation substantially as described by Zhao et al. in *Meth. Mol. Biol.* 318:315-323 (2006) and in Zhao et al., *Mol. Breed.* 8:323-333 (2001) and U.S. Pat. No. 5,981,840 issued Nov. 9, 1999.

Progeny of the regenerated plants, such as $T_1$ plants, can be subjected to a soil-based drought stress. Using image analysis, plant area, volume, growth rate and color can be measured at multiple times before and during drought stress. Significant delay in wilting or leaf area reduction, a reduced yellow-color accumulation, and/or an increased growth rate during drought stress, relative to a control, will be considered evidence that the gene functions in maize to enhance drought tolerance.

Example 5

Laboratory Drought Screening of Rice Drought Tolerance Genes in *Arabidopsis*

To understand whether rice drought tolerance genes can improve dicot plants' drought tolerance, or other traits, the rice expression vectors described herein can be transformed into *Arabidopsis* (Columbia) using floral dip method by *Agrobacterium* mediated transformation procedure and transgenic plants were identified (Clough, S. T. and Bent, A. F. (1998) *The Plant Journal* 16, 735-743; Zhang, X. et al. (2006) *Nature Protocols* 1: 641-646).

Progeny of the regenerated plants, such as $T_1$ plants, can be subjected to a soil-based drought stress. Using image analysis, plant area, volume, growth rate and color can be measured at multiple times before and during drought stress. Significant delay in wilting or leaf area reduction, a reduced yellow-color accumulation, and/or an increased growth rate during drought stress, relative to a control, will be considered evidence that the gene functions in dicot plants to enhance drought tolerance.

What is claimed is:

1. A modified plant or modified seed comprising an increased expression of at least one polynucleotide encoding a polypeptide comprising an amino acid sequence that is at least 95% identical to SEQ ID NO: 9 wherein the modified plant or plant grown from the modified seed has improved drought tolerance when compared to a control plant.

2. The modified plant or modified seed of claim 1, wherein the modified plant or modified seed comprises in its genome a recombinant DNA construct comprising a polynucleotide encoding a polypeptide comprising an amino acid sequence that is at least 95% identical to SEQ ID NO: 9 operably linked to at least one regulatory element.

3. The modified plant or modified seed of claim 1, wherein the modified plant or modified seed comprises a targeted genetic modification at an endogenous genomic locus encoding a polypeptide comprising an amino acid sequence that is at least 95% identical to SEQ ID NO: 9, thereby increasing expression of the polypeptide.

4. The modified plant or modified seed of claim 1, wherein said plant is selected from the group consisting of rice, maize, soybean, sunflower, sorghum, canola, wheat, alfalfa, cotton, barley, millet, sugar cane and switchgrass.

5. A method of increasing drought tolerance in a plant, the method comprising:

(a) introducing in a regenerable plant cell a targeted genetic modification at an endogenous genomic locus encoding a polypeptide comprising an amino acid sequence that is at least 95% identical to SEQ ID NO: 9, the targeted genetic modification introducing a modification increasing expression or activity of the polypeptide; and (b) generating the plant, wherein the plant comprises the targeted genetic modification and has increased drought tolerance as compared to a control plant not comprising the targeted genetic modification.

6. The method of claim 5, wherein the targeted genetic modification is introduced using an enzyme selected from the group consisting of a polynucleotide-guided endonuclease, CRISPR-Cas endonucleases, base editing deaminases, a zinc finger nuclease, a transcription activator-like effector nuclease (TALEN), and engineered site-specific meganucleases.

7. The method of claim 5, wherein the targeted genetic modification is present in (a) the coding region; (b) a non-coding region; (c) a regulatory sequence; (d) an untranslated region; or (e) any combination of (a)-(d) of the endogenous genomic locus.

8. A method of increasing drought tolerance in a plant, the method comprising:
  (a) expressing in a regenerable plant cell, a polynucleotide operably linked to at least one heterologous regulatory element, the polynucleotide encoding a polypeptide comprising having an amino acid sequence that is at least 95% identical to SEQ ID NO: 9; and
  (b) generating a plant from the regenerable plant cell, wherein the plant comprises in its genome the polynucleotide operably linked to the at least one heterologous regulatory element and has increased drought tolerance as compared to a control plant not comprising the polynucleotide operably linked to the at least one heterologous regulatory element.

9. The method of claim 8, wherein the heterologous regulatory element is a promoter.

10. The method of claim 8, wherein said plant is selected from the group consisting of rice, maize, soybean, sunflower, sorghum, canola, wheat, alfalfa, cotton, barley, millet, sugar cane and switchgrass.

11. The modified plant or modified seed of claim 1, wherein the polynucleotide comprises the nucleotide sequence of SEQ ID NO: 7 or SEQ ID NO: 8.

12. The modified plant or modified seed of claim 1, wherein the encoded polypeptide comprises the amino acid sequence of SEQ ID NO: 9.

13. The modified plant or seed of claim 1, wherein the modified plant or plant grown from the seed has increased grain yield under drought conditions.

14. The modified plant or seed of claim 2, wherein the regulatory element is a heterologous promoter.

* * * * *

SEQUENCE LISTING

```
<160> NUMBER OF SEQ ID NOS: 112

<210> SEQ ID NO 1
<211> LENGTH: 1182
<212> TYPE: DNA
<213> ORGANISM: Oryza sativa

<400> SEQUENCE: 1
cacttcctag caattaagat catggtgcag cgcacttcat ccgattcggc ggcgtcggct      60
gaggccatgg tcatggacct gagtcccaag cgtcccgcca agtcctacgg cggcgaaggc     120
ggctcgtact tgattggtc cccctccgag ctgcccatgc tccgcgccgc ctccatcggc      180
gccgccaaac tctcgcttgc cgccggaggc ctcgccctcc ccttctactc cgattcggct     240
aaggtggcct acgtcctcca gggcaagggc acctgcgccg ttctcctccc cgagaccccc     300
tccgagaaga tcctacccat caaagagggc gacgcgctcg cccttccatt cggcgttgtc     360
acctggtggc acaacctgca cgccgccacc accgaactcg tcgtcctctt cctcggggac     420
acatccaagg gccacaccgc cggccgcttc accaacatgc agctcaccgg ctccaccggc     480
atcttcaccg gcttctccac cgagttcgtc gcccgcgcct gggacctccc gcaggacgcc     540
gctgcctccc tcgtctccac ccagcccggc gccggcatcg tgaagctcaa ggatggcttc     600
aggatgcccg agggttgcga caaggacagg gagggcatgg tgctcaactg cttggaggcg     660
ccgctggacg tggacatcaa gaacggggc cgcgtggtgg tgctgaacac gcagaacctg     720
ccgctggtga aggaggtggg gctgggcgcc gacctggtga ggatcgacgg ccactccatg     780
tgctcgccgg ggttctcgtg cgactcggcg taccaggtga cgtacatcgt gcggggcagc     840
gggcgcgtgc aggtggtggg catcgacggg acgcgcgtgc tggagacccg cgccgagggt     900
ggctgcctct tcatcgtccc caggttcttc gtcgtctcca agatcgccga cgacaccggc     960
atggagtggt tctccatcat caccactccc aacccatct tctcccacct cgccgggagg    1020
acctccgtct ggaaggccat ctcccccgcc gtgctccagg cctccttcaa caccaccccg    1080
gagatggaga acctcttccg ctccaagagg ctcgactccg agatcttctt cgccccaat    1140 tcgaattcga tttgatggac aatatccatc ctccatctcc ag                      1182

<210> SEQ ID NO 2
<211> LENGTH: 1134
<212> TYPE: DNA
<213> ORGANISM: Oryza sativa

<400> SEQUENCE: 2
atggtgcagc gcacttcatc cgattcggcg gcgtcggctg aggccatggt catggacctg     60
```

```
agtcccaagc gtcccgccaa gtcctacggc ggcgaaggcg gctcgtactt tgattggtcc    120
ccctccgagc tgcccatgct ccgcgccgcc tccatcggcg ccgccaaact ctcgcttgcc    180
gccggaggcc tcgccctccc cttctactcc gattcggcta aggtggccta cgtcctccag    240
ggcaagggca cctgcgccgt tctcctcccc gagaccccct ccgagaagat cctacccatc    300
aaagagggcg acgcgctcgc ccttccattc ggcgttgtca cctggtggca caacctgcac    360
gccgccacca ccgaactcgt cgtcctcttc ctcggggaca catccaaggg ccacaccgcc    420
ggccgcttca ccaacatgca gctcaccggc tccaccggca tcttcaccgg cttctccacc    480
gagttcgtcg cccgcgcctg ggacctcccg caggacgccg ctgcctccct cgtctccacc    540
cagcccggcg ccggcatcgt gaagctcaag gatggcttca ggatgccga gggttgcgac    600 aaggacaggg agggcatggt gctcaactgc ttggaggcgc cgctggacgt ggacatcaag    660
aacgggggcc gcgtggtggt gctgaacacg cagaacctgc cgctggtgaa ggaggtgggg    720
ctgggcgccg acctggtgag gatcgacggc cactccatgt gctcgccggg gttctcgtgc    780
gactcggcgt accaggtgac gtacatcgtg cggggcagcg ggcgcgtgca ggtggtgggc    840
atcgacggga cgcgcgtgct ggagacccgc gccgagggtg gctgcctctt catcgtcccc    900
aggttcttcg tcgtctccaa gatcgccgac gacaccggca tggagtggtt ctccatcatc    960
accactccca accccatctt ctcccacctc gccgggagga cctccgtctg gaaggccatc   1020
tcccccgccg tgctccaggc ctccttcaac accaccccgg agatggagaa cctcttccgc   1080
tccaagaggc tcgactccga gatcttcttc gcccccaatt cgaattcgat ttga         1134

<210> SEQ ID NO 3
<211> LENGTH: 377
<212> TYPE: PRT
<213> ORGANISM: Oryza sativa

<400> SEQUENCE: 3

Met Val Gln Arg Thr Ser Ser Asp Ser Ala Ala Ser Ala Glu Ala Met
1               5                   10                  15

Val Met Asp Leu Ser Pro Lys Arg Pro Ala Lys Ser Tyr Gly Gly Glu
            20                  25                  30

Gly Gly Ser Tyr Phe Asp Trp Ser Pro Ser Glu Leu Pro Met Leu Arg
        35                  40                  45

Ala Ala Ser Ile Gly Ala Ala Lys Leu Ser Leu Ala Ala Gly Gly Leu
    50                  55                  60

Ala Leu Pro Phe Tyr Ser Asp Ser Ala Lys Val Ala Tyr Val Leu Gln
65                  70                  75                  80

Gly Lys Gly Thr Cys Ala Val Leu Leu Pro Glu Thr Pro Ser Glu Lys
                85                  90                  95

Ile Leu Pro Ile Lys Glu Gly Asp Ala Leu Ala Leu Pro Phe Gly Val
            100                 105                 110

Val Thr Trp Trp His Asn Leu His Ala Ala Thr Thr Glu Leu Val Val
        115                 120                 125

Leu Phe Leu Gly Asp Thr Ser Lys Gly His Thr Ala Gly Arg Phe Thr
    130                 135                 140

Asn Met Gln Leu Thr Gly Ser Thr Gly Ile Phe Thr Gly Phe Ser Thr
145                 150                 155                 160

Glu Phe Val Ala Arg Ala Trp Asp Leu Pro Gln Asp Ala Ala Ala Ser
                165                 170                 175

Leu Val Ser Thr Gln Pro Gly Ala Gly Ile Val Lys Leu Lys Asp Gly
            180                 185                 190
```

Phe Arg Met Pro Glu Gly Cys Asp Lys Asp Arg Glu Gly Met Val Leu
        195                 200                 205

Asn Cys Leu Glu Ala Pro Leu Asp Val Asp Ile Lys Asn Gly Gly Arg
        210                 215                 220

Val Val Val Leu Asn Thr Gln Asn Leu Pro Leu Val Lys Glu Val Gly
225                 230                 235                 240

Leu Gly Ala Asp Leu Val Arg Ile Asp Gly His Ser Met Cys Ser Pro
                245                 250                 255

Gly Phe Ser Cys Asp Ser Ala Tyr Gln Val Thr Tyr Ile Val Arg Gly
            260                 265                 270

Ser Gly Arg Val Gln Val Gly Ile Asp Gly Thr Arg Val Leu Glu
        275                 280                 285

Thr Arg Ala Glu Gly Gly Cys Leu Phe Ile Val Pro Arg Phe Phe Val
        290                 295                 300

Val Ser Lys Ile Ala Asp Asp Thr Gly Met Glu Trp Phe Ser Ile Ile
305                 310                 315                 320

Thr Thr Pro Asn Pro Ile Phe Ser His Leu Ala Gly Arg Thr Ser Val
                325                 330                 335

Trp Lys Ala Ile Ser Pro Ala Val Leu Gln Ala Ser Phe Asn Thr Thr
            340                 345                 350

Pro Glu Met Glu Asn Leu Phe Arg Ser Lys Arg Leu Asp Ser Glu Ile
        355                 360                 365

Phe Phe Ala Pro Asn Ser Asn Ser Ile
        370                 375

<210> SEQ ID NO 4
<211> LENGTH: 1767
<212> TYPE: DNA
<213> ORGANISM: Oryza sativa

<400> SEQUENCE: 4

```
tttccccttg cgagatccat ctccggctcc ggcgccggcg cgcgcgcgag gcgtggaggt    60
ggggtgggggg aggggggaat gggttggggc gcggtggtgt acgagggcgg cgtggtgggg   120
gcgtcgctgg tggggctcgg ctgggcgggg ctgtggttcc tcaaccggcg gctgtacaag   180
gagtacgagg agcggcgggc gctggtgcag atcctcttcg gcctcgtctt cgccttctcc   240
tgcaacctct tccagctcgt cctcttcgag atcctccccg tcctctccaa gcacgcccgc   300
ttcctcaact ggcacctcga cctcttctgc ctcatcctcc tcctcgtctt cgtcctcccc   360
tactaccact gctacctgct gctgcgcaac tcaggggtgc ggagggagcg ggctctgctc   420
gtcgcggcgc tgttcctgct ggtcttcctc tatggcttct ggcgcatggg gattcatttc   480
cccatgcctt ctccggaaaa agggttttc acgatgcccc agttggttag taggattggc   540
gtgattggag taagtgtcat ggctgttctt tctggttttg gtgccgtcaa tctgccttac   600
agctatctgt cactgtttat cagggaaatt gatgaaaagg acatcaaaac attggaaagg   660
cagctcatgc aatccatgga gacatgcatc gctaagaaaa agaaaattgt tctgtccaaa   720
atggagatgg agaggattca aggatcagaa gagaagctaa aagccagatc atttctaaag   780
cgtatcgttg ggacagttgt tcgatctgtg caagaagatc aaactgagca ggatatcaaa   840
agcttggatg cagaggtcca ggcactagaa gaactttcca acaactatt tcttgagata   900
tatgaactcc gtcaagcaaa gatagctgct gcgttttctc gaacttggag aggccatgct   960
cagaatctac taggatatgc tttgtcagtg tattgtgttt ataagatgct caagtccttg  1020
```

| | |
|---|---|
| cagagtgttg tctttaaaga ggcaggttct gttgatccag taaccatgac aattaccatc | 1080 |
| ttcttgaggc attttgacat tggtattgat gtcactcttt tatcacagta tatatctctc | 1140 |
| atatttatcg ggatgttggt tgtcatatct gttcgaggtt tcttggcaaa tgttatgaag | 1200 |
| ttcttctttg ctgtttctag agttgggagt ggttcaacaa ccaatgttgt cctttttcta | 1260 |
| tctgagatca tgggaatgta cttcatatca tctattcttc tcataaggaa aagcctggca | 1320 |
| aatgagtata gggtgatcat tacagatgtt ttgggtggtg atatccagtt tgacttttac | 1380 |
| caccgctggt ttgatgctat atttgtggct agtgcatttc tgtccttgct tctgatttct | 1440 |
| gcccaataca cctcccggca aacagacaag cacccaattg attgatgctt ttgtaccatt | 1500 |
| tgtgcatagt gttctttta ccactttgtc caaggttgac ccattcattc taccagtttc | 1560 |
| caaaggttgt cgtttctcca tggacttcca tatacagtta cagaacataa tacatcagtt | 1620 |
| aacttgaagg tgtctccttg ttttggagta tgtttcctga cgttgaatca tggtgaaaca | 1680 |
| gtttctccat atgcaagtca ttaggaatgc tttgcatcgt gatgatgcag aactgcaaat | 1740 |
| ggggccggtt gtaatgttgt gtccaca | 1767 |

<210> SEQ ID NO 5
<211> LENGTH: 1407
<212> TYPE: DNA
<213> ORGANISM: Oryza sativa

<400> SEQUENCE: 5

| | |
|---|---|
| atgggttggg gcgcggtggt gtacgagggc ggcgtggtgg gggcgtcgct ggtggggctc | 60 |
| ggctgggcgg ggctgtggtt cctcaaccgg cggctgtaca aggagtacga ggagcggcgg | 120 |
| gcgctggtgc agatcctctt cggcctcgtc ttcgccttct cctgcaacct cttccagctc | 180 |
| gtcctcttcg agatcctccc cgtcctctcc aagcacgccc gcttcctcaa ctggcacctc | 240 |
| gacctcttct gcctcatcct cctcctcgtc ttcgtcctcc cctactacca ctgctacctg | 300 |
| ctgctgcgca actcagggt gcggagggag cgggctctgc tcgtcgcggc gctgttcctg | 360 |
| ctggtcttcc tctatggctt ctggcgcatg gggattcatt tccccatgcc ttctccggaa | 420 |
| aaagggtttt tcacgatgcc ccagttggtt agtaggattg gcgtgattgg agtaagtgtc | 480 |
| atggctgttc tttctggttt tggtgccgtc aatctgcctt acagctatct gtcactgttt | 540 |
| atcagggaaa ttgatgaaaa ggacatcaaa acattggaaa ggcagctcat gcaatccatg | 600 |
| gagacatgca tcgctaagaa aaagaaaatt gttctgtcca aaatggagat ggagaggatt | 660 |
| caaggatcag aagagaagct aaaagccaga tcatttctaa agcgtatcgt tgggacagtt | 720 |
| gttcgatctg tgcaagaaga tcaaactgag caggatatca aaagcttgga tgcagaggtc | 780 |
| caggcactag aagaactttc caaacaacta tttcttgaga tatatgaact ccgtcaagca | 840 |
| aagatagctg ctgcgttttc tcgaacttgg agaggccatg ctcagaatct actaggatat | 900 |
| gctttgtcag tgtattgtgt ttataagatg ctcaagtcct tgcagagtgt tgtctttaaa | 960 |
| gaggcaggtt ctgttgatcc agtaaccatg acaattacca tcttcttgag gcattttgac | 1020 |
| attggtattg atgtcactct tttatcacag tatatatctc tcatatttat cgggatgttg | 1080 |
| gttgtcatat ctgttcgagg tttcttggca atgttatga agttcttctt tgctgttttct | 1140 |
| agagttggga gtggttcaac aaccaatgtt gtcctttttc tatctgagat catgggaatg | 1200 |
| tacttcatat catctattct tctcataagg aaaagcctgg caaatgagta tagggtgatc | 1260 |
| attacagatg ttttgggtgg tgatatccag tttgactttt accaccgctg gtttgatgct | 1320 |
| atatttgtgg ctagtgcatt tctgtccttg cttctgattt ctgcccaata cacctcccgg | 1380 | caaacagaca agcacccaat tgattga        1407

<210> SEQ ID NO 6
<211> LENGTH: 468
<212> TYPE: PRT
<213> ORGANISM: Oryza sativa

<400> SEQUENCE: 6

```
Met Gly Trp Gly Ala Val Val Tyr Glu Gly Gly Val Val Gly Ala Ser
1               5                   10                  15

Leu Val Gly Leu Gly Trp Ala Gly Leu Trp Phe Leu Asn Arg Arg Leu
            20                  25                  30

Tyr Lys Glu Tyr Glu Arg Ala Leu Val Gln Ile Leu Phe Gly
        35                  40                  45

Leu Val Phe Ala Phe Ser Cys Asn Leu Phe Gln Leu Val Leu Phe Glu
        50                  55                  60

Ile Leu Pro Val Leu Ser Lys His Ala Arg Phe Leu Asn Trp His Leu
65                  70                  75                  80

Asp Leu Phe Cys Leu Ile Leu Leu Val Phe Val Leu Pro Tyr Tyr
                    85                  90                  95

His Cys Tyr Leu Leu Arg Asn Ser Gly Val Arg Arg Glu Arg Ala
                100                 105                 110

Leu Leu Val Ala Ala Leu Phe Leu Leu Val Phe Leu Tyr Gly Phe Trp
            115                 120                 125

Arg Met Gly Ile His Phe Pro Met Pro Ser Pro Glu Lys Gly Phe Phe
130                 135                 140

Thr Met Pro Gln Leu Val Ser Arg Ile Gly Val Ile Gly Val Ser Val
145                 150                 155                 160

Met Ala Val Leu Ser Gly Phe Gly Ala Val Asn Leu Pro Tyr Ser Tyr
                    165                 170                 175

Leu Ser Leu Phe Ile Arg Glu Ile Asp Glu Lys Asp Ile Lys Thr Leu
                180                 185                 190

Glu Arg Gln Leu Met Gln Ser Met Glu Thr Cys Ile Ala Lys Lys Lys
            195                 200                 205

Lys Ile Val Leu Ser Lys Met Glu Met Glu Arg Ile Gln Gly Ser Glu
        210                 215                 220

Glu Lys Leu Lys Ala Arg Ser Phe Leu Lys Arg Ile Val Gly Thr Val
225                 230                 235                 240

Val Arg Ser Val Gln Glu Asp Gln Thr Glu Gln Asp Ile Lys Ser Leu
                    245                 250                 255

Asp Ala Glu Val Gln Ala Leu Glu Glu Leu Ser Lys Gln Leu Phe Leu
                260                 265                 270

Glu Ile Tyr Glu Leu Arg Gln Ala Lys Ile Ala Ala Phe Ser Arg
            275                 280                 285

Thr Trp Arg Gly His Ala Gln Asn Leu Leu Gly Tyr Ala Leu Ser Val
        290                 295                 300

Tyr Cys Val Tyr Lys Met Leu Lys Ser Leu Gln Ser Val Val Phe Lys
305                 310                 315                 320

Glu Ala Gly Ser Val Asp Pro Val Thr Met Thr Ile Thr Ile Phe Leu
                    325                 330                 335

Arg His Phe Asp Ile Gly Ile Asp Val Thr Leu Leu Ser Gln Tyr Ile
                340                 345                 350

Ser Leu Ile Phe Ile Gly Met Leu Val Val Ile Ser Val Arg Gly Phe
            355                 360                 365
```

Leu Ala Asn Val Met Lys Phe Phe Ala Val Ser Arg Val Gly Ser
    370                 375                 380

Gly Ser Thr Thr Asn Val Val Leu Phe Leu Ser Glu Ile Met Gly Met
385                 390                 395                 400

Tyr Phe Ile Ser Ser Ile Leu Leu Ile Arg Lys Ser Leu Ala Asn Glu
            405                 410                 415

Tyr Arg Val Ile Ile Thr Asp Val Leu Gly Gly Asp Ile Gln Phe Asp
                420                 425                 430

Phe Tyr His Arg Trp Phe Asp Ala Ile Phe Val Ala Ser Ala Phe Leu
        435                 440                 445

Ser Leu Leu Leu Ile Ser Ala Gln Tyr Thr Ser Arg Gln Thr Asp Lys
    450                 455                 460

His Pro Ile Asp
465

<210> SEQ ID NO 7
<211> LENGTH: 496
<212> TYPE: DNA
<213> ORGANISM: Oryza sativa

<400> SEQUENCE: 7
cacctcgtgt gctacaagtg ctacagtaat ctacatttac taatgacgga ttgattataa      60
tcttttgtgt atgttttcct attataaact cttctattat aaaattttaa tgtgtttctg     120
taaaaaaaaa tccgtatttt tttccatcgt cgtgtcggtt tatttcccac acgacgcaac     180
cgcgctcact cagccaatct acgcattcgc ttacagatac acgcgcgccc agctgaccat     240
ctgccccctta ggctcttggc tgccgcagct ggacaatggc catgcctcac ctgagccaaa     300
tggtctaatg ggttttctt tttttatta ttctctgttt tcacctactc actttgatat      360
atcttggtat aaataaactg gatgagatat tatacaatat gtatggtaaa tcccataact      420
ttatcaagcc atgcattttt catgtgacgt ttgtggtgtg tattttttttt ccactgaacc      480
acttttagct actccc                                                     496

<210> SEQ ID NO 8
<211> LENGTH: 306
<212> TYPE: DNA
<213> ORGANISM: Oryza sativa

<400> SEQUENCE: 8
atgttttcct attataaact cttctattat aaaattttaa tgtgtttctg taaaaaaaaa      60
tccgtatttt tttccatcgt cgtgtcggtt tatttcccac acgacgcaac cgcgctcact     120
cagccaatct acgcattcgc ttacagatac acgcgcgccc agctgaccat ctgccccctta     180
ggctcttggc tgccgcagct ggacaatggc catgcctcac ctgagccaaa tggtctaatg     240
ggttttctt tttttatta ttctctgttt tcacctactc actttgatat atcttggtat      300
aaataa                                                                306

<210> SEQ ID NO 9
<211> LENGTH: 101
<212> TYPE: PRT
<213> ORGANISM: Oryza sativa

<400> SEQUENCE: 9

Met Phe Phe Tyr Tyr Lys Leu Phe Tyr Tyr Lys Ile Leu Met Cys Phe
1               5                   10                  15

```
Cys Lys Lys Lys Ser Val Phe Phe Ser Ile Val Ser Val Tyr Phe
             20                  25                  30

Pro His Asp Ala Thr Ala Leu Thr Gln Pro Ile Tyr Ala Phe Ala Tyr
         35                  40                  45

Arg Tyr Thr Arg Ala Gln Leu Thr Ile Cys Pro Leu Gly Ser Trp Leu
     50                  55                  60

Pro Gln Leu Asp Asn Gly His Ala Ser Pro Glu Pro Asn Gly Leu Met
 65              70                  75                  80

Gly Phe Ser Phe Phe Tyr Tyr Ser Leu Phe Ser Pro Thr His Phe Asp
                 85                  90                  95

Ile Ser Trp Tyr Lys
            100

<210> SEQ ID NO 10
<211> LENGTH: 1838
<212> TYPE: DNA
<213> ORGANISM: Oryza sativa

<400> SEQUENCE: 10
cgatgaagta cgtgctggtg acgggcgggg tggtgagcgg cctcgggaag ggggtgacgg      60
cgagcagcat cggcgtcgtg ctcaaggact gcggcctccg cgtcacctcc atcaagatcg     120
atccttacct caacaccgat gctggaacca tgtctccatt cgagcacggt gaagtgtttg     180
ttttggacga tggtggtgag gtggacttgg accttggaaa ttatgagcga tttctggaca     240
tcaagttgac tcgtgacaac aatataacca cgggaaagat ctatcaggct gttattgaca     300
aggaacgaag aggagactac ttgggaaaaa ctgttcaggt gtaccacac attacggatg      360 aaatacagga gtggattgaa cgtgtggcaa tgaatccagt tgatggcaca gatgagccag     420
ctgatgtttg tgtaatagaa cttggtggca ctataggga tattgaatca atgccttta      480 ttgaagcatt aggtcaattt tcataccgcg tagggctgg aaacttttgc ctagttcatg      540
tcagtcttgt accagttcta aatgtagttg gtgaacagaa aaccaaacct acccaacata     600
gtgtccgtgg actaagagga cttggactga tacctgatat tttagcatgt cgcagtactc     660
agccacttga agaaaatgtg aaagtgaaac tcgcacaatt ttgccacgtt ccgatctcaa     720
atattgtcaa tcttcacgat gttaccaaca tctggcacat cccttttgttg cttagggacc    780 agaaggctca tgaatctatt ctgaaagttt tagatcttca atgtgtggga aaagtgcctc     840
gagcacctaa gctgactgaa tggactgaaa gagccagcaa attcgacaaa ctgaaaactc     900
ctgttaggat tgccatggtt ggaaagtata ctggcctatc agactcctac ttgtcagttt     960
tgaaggctct tctgcatgca tcggttgctt tggacagaaa acttgtggtg gattgggttc    1020
cttcctgtga tcttgaagat tctgcagcca cagagactcc tgatgcatat gaaaaagctt    1080
gggatctact aaagggtgca catggtgtac tagttccagg aggctttgga gatagagggg    1140
tccagggaaa aattcttgct gcaaaatatg cgcgagaaaa caatgttcca tatcttggta    1200
tttgcctggg catgcaaatt gcagtgatcg aattcgcccg ctctgtcatg aagttgcgtg    1260
gtgctaatag tacagagttt gatccagcta caacgacgcc atgtgttatt ttcatgccgg    1320
agggctctaa aacccatatg ggggcaacaa tgcgccttgg atcaaggagg accttcttcc    1380
aggccaatac atgcaaatca gctaagctgt atggcaatgc aagctatgta gatgaaaggc    1440
accgccaccg atatgaggtg aatcctgaaa tggttccaga atttgagaag gcaggtctct    1500
cttttgttgg cagggatgaa agcgggacac gcatggagat aattgagcta ccaactcata    1560
ggttttttgt tggcgcacaa tttcatcctg aattcaagtc aagacctgga aagccatccc    1620
```

```
cactttttcat gggattaata gcagcttcat caggacagct tgaccattta cttcagcaat    1680
cttgcggcgt tgtcagctcg ccagtcagac gtggcaacta ctgcaacgga gccacgaaac    1740
aacagaagct ataccaaaat ggacatgtca agaacggcct ggtgaacggc tgctactatg    1800
caaacggcaa cagcattctt catacttagc agcatagc                            1838

<210> SEQ ID NO 11
<211> LENGTH: 1827
<212> TYPE: DNA
<213> ORGANISM: Oryza sativa

<400> SEQUENCE: 11
atgaagtacg tgctggtgac gggcggggtg gtgagcggcc tcgggaaggg ggtgacggcg      60
agcagcatcg cgtcgtgct caaggactgc ggcctccgcg tcacctccat caagatcgat     120
ccttacctca acaccgatgc tggaaccatg tctccattcg agcacggtga agtgtttgtt     180
ttggacgatg tggtgaggt ggacttggac cttggaaatt atgagcgatt tctggacatc     240
aagttgactc gtgacaacaa tataaccacg ggaaagatct atcaggctgt tattgacaag     300
gaacgaagag gagactactt gggaaaaaact gttcaggttg taccacacat tacgatgaa      360 atacaggagt ggattgaacg tgtggcaatg aatccagttg atggcacaga tgagccagct     420
gatgtttgtg taatagaact tggtggcact ataggggata ttgaatcaat gccttttatt     480
gaagcattag gtcaatttttc ataccgcgta ggggctggaa acttttgcct agttcatgtc     540
agtcttgtac cagttctaaa tgtagttggt gaacagaaaa ccaaacctac ccaacatagt     600
gtccgtggac taagaggact tggactgata cctgatattt tagcatgtcg cagtactcag     660
ccacttgaag aaaatgtgaa agtgaaactc gcacaatttt gccacgttcc gatctcaaat     720
attgtcaatc ttcacgatgt taccaacatc tggcacatcc ctttgttgct tagggaccag     780
aaggctcatg aatctattct gaaagtttta gatcttcaat gtgtgggaaa agtgcctcga     840
gcacctaagc tgactgaatg gactgaaaga gccagcaaat tcgacaaact gaaaactcct     900
gttaggattg ccatggttgg aaagtatact ggcctatcag actcctactt gtcagttttg     960
aaggctcttc tgcatgcatc ggttgctttg gacagaaaac ttgtggtgga ttgggttcct    1020
tcctgtgatc ttgaagattc tgcagccaca gagactcctg atgcatatga aaaagcttgg    1080
gatctactaa agggtgcaca tggtgtacta gttccaggag gctttggaga tagaggggtc    1140
cagggaaaaa ttcttgctgc aaaatatgcg cgagaaaaca atgttccata tcttggtatt    1200
tgcctgggca tgcaaattgc agtgatcgaa ttcgcccgct ctgtcatgaa gttgcgtggt    1260
gctaatagta cagagtttga tccagctaca acgacgccat gttattttt catgccggag    1320 ggctctaaaa cccatatggg ggcaacaatg cgccttggat caaggaggac cttcttccag    1380
gccaatacat gcaaatcagc taagctgtat ggcaatgcaa gctatgtaga tgaaaggcac    1440
cgccaccgat atgaggtgaa tcctgaaatg gttccagaat ttgagaaggc aggtctctct    1500
tttgttggca gggatgaaag cgggacacgc atggagataa ttgagctacc aactcatagg    1560
ttttttgttg cgcacaaatt tcatcctgaa ttcaagtcaa gacctggaaa gccatcccca    1620
cttttcatgg gattaatagc agcttcatca ggacagcttg accatttact tcagcaatct    1680
tgcggcgttg tcagctcgcc agtcagacgt ggcaactact gcaacggagc cacgaaacaa    1740
cagaagctat accaaaatgg acatgtcaag aacggcctgg tgaacggctg ctactatgca    1800
aacggcaaca gcattcttca tacttag                                        1827
```

<210> SEQ ID NO 12
<211> LENGTH: 608
<212> TYPE: PRT
<213> ORGANISM: Oryza sativa

<400> SEQUENCE: 12

```
Met Lys Tyr Val Leu Val Thr Gly Gly Val Ser Gly Leu Gly Lys
1               5                   10                  15

Gly Val Thr Ala Ser Ser Ile Gly Val Val Leu Lys Asp Cys Gly Leu
            20                  25                  30

Arg Val Thr Ser Ile Lys Ile Asp Pro Tyr Leu Asn Thr Asp Ala Gly
        35                  40                  45

Thr Met Ser Pro Phe Glu His Gly Glu Val Phe Val Leu Asp Asp Gly
    50                  55                  60

Gly Glu Val Asp Leu Asp Leu Gly Asn Tyr Glu Arg Phe Leu Asp Ile
65                  70                  75                  80

Lys Leu Thr Arg Asp Asn Asn Ile Thr Thr Gly Lys Ile Tyr Gln Ala
                85                  90                  95

Val Ile Asp Lys Glu Arg Arg Gly Asp Tyr Leu Gly Lys Thr Val Gln
            100                 105                 110

Val Val Pro His Ile Thr Asp Glu Ile Gln Glu Trp Ile Glu Arg Val
        115                 120                 125

Ala Met Asn Pro Val Asp Gly Thr Asp Glu Pro Ala Asp Val Cys Val
    130                 135                 140

Ile Glu Leu Gly Gly Thr Ile Gly Asp Ile Glu Ser Met Pro Phe Ile
145                 150                 155                 160

Glu Ala Leu Gly Gln Phe Ser Tyr Arg Val Gly Ala Gly Asn Phe Cys
                165                 170                 175

Leu Val His Val Ser Leu Val Pro Val Leu Asn Val Val Gly Glu Gln
            180                 185                 190

Lys Thr Lys Pro Thr Gln His Ser Val Arg Gly Leu Arg Gly Leu Gly
        195                 200                 205

Leu Ile Pro Asp Ile Leu Ala Cys Arg Ser Thr Gln Pro Leu Glu Glu
    210                 215                 220

Asn Val Lys Val Lys Leu Ala Gln Phe Cys His Val Pro Ile Ser Asn
225                 230                 235                 240

Ile Val Asn Leu His Asp Val Thr Asn Ile Trp His Ile Pro Leu Leu
                245                 250                 255

Leu Arg Asp Gln Lys Ala His Glu Ser Ile Leu Lys Val Leu Asp Leu
            260                 265                 270

Gln Cys Val Gly Lys Val Pro Arg Ala Pro Lys Leu Thr Glu Trp Thr
        275                 280                 285

Glu Arg Ala Ser Lys Phe Asp Lys Leu Lys Thr Pro Val Arg Ile Ala
    290                 295                 300

Met Val Gly Lys Tyr Thr Gly Leu Ser Asp Ser Tyr Leu Ser Val Leu
305                 310                 315                 320

Lys Ala Leu Leu His Ala Ser Val Ala Leu Asp Arg Lys Leu Val Val
                325                 330                 335

Asp Trp Val Pro Ser Cys Asp Leu Glu Asp Ser Ala Ala Thr Glu Thr
            340                 345                 350

Pro Asp Ala Tyr Glu Lys Ala Trp Asp Leu Leu Lys Gly Ala His Gly
        355                 360                 365

Val Leu Val Pro Gly Gly Phe Gly Asp Arg Gly Val Gln Gly Lys Ile
    370                 375                 380
```

Leu Ala Ala Lys Tyr Ala Arg Glu Asn Asn Val Pro Tyr Leu Gly Ile
385                 390                 395                 400

Cys Leu Gly Met Gln Ile Ala Val Ile Glu Phe Ala Arg Ser Val Met
            405                 410                 415

Lys Leu Arg Gly Ala Asn Ser Thr Glu Phe Asp Pro Ala Thr Thr Thr
            420                 425                 430

Pro Cys Val Ile Phe Met Pro Glu Gly Ser Lys Thr His Met Gly Ala
            435                 440                 445

Thr Met Arg Leu Gly Ser Arg Arg Thr Phe Phe Gln Ala Asn Thr Cys
        450                 455                 460

Lys Ser Ala Lys Leu Tyr Gly Asn Ala Ser Tyr Val Asp Glu Arg His
465                 470                 475                 480

Arg His Arg Tyr Glu Val Asn Pro Glu Met Val Pro Glu Phe Glu Lys
                485                 490                 495

Ala Gly Leu Ser Phe Val Gly Arg Asp Glu Ser Gly Thr Arg Met Glu
            500                 505                 510

Ile Ile Glu Leu Pro Thr His Arg Phe Phe Val Gly Ala Gln Phe His
            515                 520                 525

Pro Glu Phe Lys Ser Arg Pro Gly Lys Pro Ser Pro Leu Phe Met Gly
        530                 535                 540

Leu Ile Ala Ala Ser Ser Gly Gln Leu Asp His Leu Leu Gln Gln Ser
545                 550                 555                 560

Cys Gly Val Val Ser Ser Pro Val Arg Arg Gly Asn Tyr Cys Asn Gly
            565                 570                 575

Ala Thr Lys Gln Gln Lys Leu Tyr Gln Asn Gly His Val Lys Asn Gly
            580                 585                 590

Leu Val Asn Gly Cys Tyr Tyr Ala Asn Gly Asn Ser Ile Leu His Thr
        595                 600                 605

<210> SEQ ID NO 13
<211> LENGTH: 845
<212> TYPE: DNA
<213> ORGANISM: Oryza sativa

<400> SEQUENCE: 13
cggaggcagt gacaacgaca gcgtggagct aaggcggagg tcggttgggg cgatggttgg      60
cgatggtgat ggctggatgg gtgtgggatt gatccaccgt cccccttgacc atggcgtgg    120 caacggcaag gcgaggcgg tgcagttcga ccttgaaggt gtgactgcat gcgggaggtc    180
ggtaaggtgc gtatgaggtg gaggccaaca tgtcacgcgg cctgcaggga gtgagaccat    240
ggctggtagt ggaggcggcg gagtgtagcc gtggagtaca cagtggtgga gcaccacgct    300
ggatgcaacc gcgaaccgag tgcgggatgc agcgtgatga caattggcaa ggcgtcggcg    360
tggcggacat gcagcctaag gtggtgcaat ataggcagcc tggccaaggt ggcgaggaag    420
gtggcaccgt gaggtcggat tgagggtctg cgacaggaac ctctcccata cggttgtcct    480
cttgcggcga tagcttgctg ccgaaagatg ccacgttag tgggctagtg cggggagtg     540 gggatccagc cttctctctc accctctccc tctccaaccc aactgtgtgg atagggttg    600 agcatgtcgg aggccgtgct cctccttgat gatcagctag tggcgagatg ttggtgtgat   660
gactatgtgt tgaaggtgtt cagttggcaa tggcgacgct gcggccgcc gcactgccct    720 tagggtgttt ctacggaatc tcactcattc cctgttggaa ttccttagtt gaaaaccacg    780
tcatgttgct acgacgaacg gtggtggtgc ttcgttttct tccctggaga cgtcgtttga    840

|  |  |
| --- | --- |
| ggatc | 845 |

<210> SEQ ID NO 14
<211> LENGTH: 231
<212> TYPE: DNA
<213> ORGANISM: Oryza sativa

<400> SEQUENCE: 14

| | |
|---|---|
| atggttggcg atggtgatgg ctggatgggt gtgggattga tccaccgtcc ccttgaccat | 60 |
| ggcggtggca acggcaaggg cgaggcggtg cagttcgacc ttgaaggtgt gactgcatgc | 120 |
| gggaggtcgg taaggtgttc agttggcaat ggcgacgctt gcggccgccg cactgccctt | 180 |
| agggtgtttc tacggaatct cactcattcc ctgttggatt tccttagttg a | 231 |

<210> SEQ ID NO 15
<211> LENGTH: 76
<212> TYPE: PRT
<213> ORGANISM: Oryza sativa

<400> SEQUENCE: 15

Met Val Gly Asp Gly Asp Gly Trp Met Gly Val Gly Leu Ile His Arg
1               5                   10                  15

Pro Leu Asp His Gly Gly Gly Asn Gly Lys Gly Glu Ala Val Gln Phe
            20                  25                  30

Asp Leu Glu Gly Val Thr Ala Cys Gly Arg Ser Val Arg Cys Ser Val
        35                  40                  45

Gly Asn Gly Asp Ala Cys Gly Arg Arg Thr Ala Leu Arg Val Phe Leu
    50                  55                  60

Arg Asn Leu Thr His Ser Leu Leu Asp Phe Leu Ser
65                  70                  75

<210> SEQ ID NO 16
<211> LENGTH: 1159
<212> TYPE: DNA
<213> ORGANISM: Oryza sativa

<400> SEQUENCE: 16

| | |
|---|---|
| ccttcctcct ctctctctca ctcttgtgac cacgtcggac aagcattccg ctacggcgag | 60 |
| atggcgcagg cgacgtacga cgccttcaac cgcgagaagc tctcgccgca tgcgggcctc | 120 |
| tcgaggttcg ccatacgccg cttcttcgag tgggcgcagc tgcggggcca cgccgcggcg | 180 |
| taccgcgtca ccaggttcct gtacgcgacg tcgtgcgtcg ccgtgccggt aatggccaca | 240 |
| acaaggacag tgctcgagat caggtaatgg ccggagtagc gcggcactgt cacctgcaac | 300 |
| attgttactg atcgacatgg atgttgccat gcaggtgttg agcgaggtgg cgaggctggt | 360 |
| gagcatgtat caggacgagg agctgagcat cacggcgacg gacacaacc tcggcgccgc | 420 |
| actcgcgacg ctgaacgcgt tcgacatcgt cgccaacgga tacaacaggc accccggtca | 480 |
| ccgcgttcgt attcgccaac ccgcacgtcg cgggcacgg cttcaagagt cgcttcgacg | 540 |
| gcgcacgtgg ccttggcctc cgcctcctcc gcgtccacaa cgcacgcgac gtcgtcccca | 600 |
| ggtactcgac ggcgccgccg aaccgcggcg tgggcaccga gctggcgatc gacacgggcg | 660 |
| agtcgccgta cctgagaagg ctcgcgaacg agctggtgtg gcacaaactc gatagctacc | 720 |
| tgcacggcgt ggccggcgcg gcggcggtg aggccgggcg gttcaagctc gccgcgaacg | 780 |
| ctggcgaaca aggcctacgg cgcgctgggc gaggagcacg ctcgaaatca acggcggcg | 840 |
| gcgagcgggg ctgagcggcg gccggcggcg tgcgagcgcg cggaagccga cggagcagag | 900 |

```
cggcggtggg cgagcgcgtg gcagagggcg gagcgaagcg gtggcgcgga gcggcgggca      960
agcgcgcggt ggccgacgga gcggaacggc ggcggtctgc cgccggggga ggagctgggc     1020
gagggcggca gccaccgagc caccgcctcc tctgggcccc gccttcgagc tcctcgccga     1080
cgaccgcggc cacccacct cctcccttc cacgcggtgg tgctcgccgg cgacggtgga      1140
tttggacttg ggaggagct                                                  1159
```

<210> SEQ ID NO 17
<211> LENGTH: 645
<212> TYPE: DNA
<213> ORGANISM: Oryza sativa

<400> SEQUENCE: 17

```
atggcgcagg cgacgtacga cgccttcaac cgcgagaagc tctcgccgca tgcgggcctc       60
tcgaggttcg ccatacgccg cttcttcgag tgggcgcagc tgcggggcca cgccgcggcg      120
taccgcgtca ccaggttcct gtacgcgacg tcgtgcgtcg ccgtgccggt gttgagcgag      180
gtggcgaggc tggtgagcat gtatcaggac gaggagctga gcatcaccgg cacgggacac      240
aacctcggcg ccgcactcgc gacgctgaac gcgttcgaca tcgtcgccaa cggatacaac      300
aggcaccccg gtcaccgcag tcgcttcgac ggcgcacgtg gccttggcct ccgcctcctc      360
cgcgtccaca acgcacgcga cgtcgtcccc aggtactcga cggcgccgcc gaaccgcggc      420
gtgggcaccg agctggcgat cgacacgggc gagtcgccgt acctgagaag gctcgcgaac      480
gagctggtgt ggcacaaact cgatagctac ctgcacggcg tggccggcgc gcgcggcggt      540
gaggccgggc ggttcaagct cgccgcgaac gctggcgaac aaggcctacg gcgcgctggg      600
cgaggagcac gctcgaaatc aacgggcggc ggcgagcggg gctga                     645
```

<210> SEQ ID NO 18
<211> LENGTH: 214
<212> TYPE: PRT
<213> ORGANISM: Oryza sativa

<400> SEQUENCE: 18

```
Met Ala Gln Ala Thr Tyr Asp Ala Phe Asn Arg Glu Lys Leu Ser Pro
1               5                   10                  15

His Ala Gly Leu Ser Arg Phe Ala Ile Arg Arg Phe Phe Glu Trp Ala
            20                  25                  30

Gln Leu Arg Gly His Ala Ala Ala Tyr Arg Val Thr Arg Phe Leu Tyr
        35                  40                  45

Ala Thr Ser Cys Val Ala Val Pro Val Leu Ser Glu Val Ala Arg Leu
    50                  55                  60

Val Ser Met Tyr Gln Asp Glu Glu Leu Ser Ile Thr Ala Thr Gly His
65                  70                  75                  80

Asn Leu Gly Ala Ala Leu Ala Thr Leu Asn Ala Phe Asp Ile Val Ala
                85                  90                  95

Asn Gly Tyr Asn Arg His Pro Gly His Arg Ser Arg Phe Asp Gly Ala
            100                 105                 110

Arg Gly Leu Gly Leu Arg Leu Leu Arg Val His Asn Ala Arg Asp Val
        115                 120                 125

Val Pro Arg Tyr Ser Thr Ala Pro Pro Asn Arg Gly Val Gly Thr Glu
    130                 135                 140

Leu Ala Ile Asp Thr Gly Glu Ser Pro Tyr Leu Arg Arg Leu Ala Asn
145                 150                 155                 160

Glu Leu Val Trp His Lys Leu Asp Ser Tyr Leu His Gly Val Ala Gly
```

|  |  |  | 165 |  |  |  | 170 |  |  |  | 175 |  |
|---|---|---|---|---|---|---|---|---|---|---|---|---|
| Ala | Arg | Gly | Gly | Glu | Ala | Gly | Arg | Phe | Lys | Leu | Ala | Ala | Asn | Ala | Gly |
|  |  |  | 180 |  |  |  | 185 |  |  |  | 190 |  |

| Glu | Gln | Gly | Leu | Arg | Arg | Ala | Gly | Arg | Gly | Ala | Arg | Ser | Lys | Ser | Thr |
|  |  | 195 |  |  |  | 200 |  |  |  | 205 |  |  |

| Gly | Gly | Gly | Glu | Arg | Gly |
|  | 210 |

<210> SEQ ID NO 19
<211> LENGTH: 1759
<212> TYPE: DNA
<213> ORGANISM: Oryza sativa

<400> SEQUENCE: 19

| gatctatcaa gtttgtcagg cgagatgaag caagttctgg cccccataat agccttggtc | 60 |
| attggaattg gaacactagc tttcatggcc attagtcctc aggtttgcca tgctgctgca | 120 |
| ggaggaagtg ctactgtggc gagaagcatc ttcgtcagca agaagggtag tggtgctgat | 180 |
| ttcacaagga tacaagacgc catcaactcc gtcccattcg ccaaccggcg gtggatccgg | 240 |
| attcacatcg ccgccggcgt ctacaagtaa cacatgcaat tcattcttg ttcaaagcat | 300 |
| gcattttcc tcttctgatg tacactactg atgagtctgt gaaattgtgt aagtgattgt | 360 |
| taggacctat tcagagtcta acagtgatct tttgatatta aatgagcaat cgttttgatt | 420 |
| gatcagaggt gcatggatga cttaaatcaa gacggatttt gtttcgaaat tgggagtgca | 480 |
| gaagattttg gtgattatga tttgattgtt tgtgctaatt aattaatttt ggttttgtgt | 540 |
| cattgggttt ggaagggaga aggtgagcat accggcgaac aagagcttca tcttgctgga | 600 |
| aggcgagggg aggcagcaga cgtcgatcga gtgggcggac cacgccggcg gcggcggcgg | 660 |
| ggactccggc acggccgact cgccgacgtt cgcctcgtac gccgccgact tcatggcccg | 720 |
| cgacatcacc ttcaaggtac gtacgtcggt gccaccacac gacgacgtac gacgaggtgg | 780 |
| tgaccgaccg tgtcgatcgc gccattgctg catgcagaac acgtacggga ggatggcgcc | 840 |
| ggcggtggcg cgctggtgg ccggagaccg tcggcgttc taccggtgcg gcttcgtggg | 900 |
| gctgcaggac acgctgagcg acctgctggg gaggcactac tacgagcgct gctacgtcga | 960 |
| gggcgccgtc gacttcatct tcggggaagc ccagtccatc ttccaccgct gccacatctc | 1020 |
| caccgcggcg gcggcggcgc ccgggttcat cacggcgcag gccggagca gcgcgtccga | 1080 |
| cgcgagcggg ttcgtgttca cctcgtgcac cgtcggcggc gccgccccgg cgtacctggg | 1140 |
| ccgcgcgtgg cgtgcctacg cgcgcgtcgt gttctaccgg acagccatgt ccgccgccgt | 1200 |
| cgtcggcctc ggctgggacg cctgggacta caagggcaaa gagtgagtct tgagtcatgc | 1260 |
| actactagaa aaagtatttt cgcgggaaaa ataggtcttc gaggtggacg ccggctccgc | 1320 |
| ctgcaaagat cgttttcgca ggcggcacct tatgttgtat gcctgcgata agctgtcttc | 1380 |
| gcaggcaaac ggccaactcc tcctcggtaa tcattttcgt cggcgggatt tcgctccga | 1440 |
| tggccatatc cgcctgcgaa aaaaaaagc ctaacaacgg tgaaaatgtt ttttctaagt | 1500 |
| agtgatggtc atcgccgtcg tcggtgcatg atcggaagtg gctgattgct acgtggatgc | 1560 |
| gtgcaggag acgctggaga tggtggagtc ggggtgcacg gggccggggt cgaacaggac | 1620 |
| ggggagggtg ccatgggaga agacgctgag cggggaggag ctcgccaagc tcgtcgacat | 1680 |
| ctcgtacgtc tcccgcgacg gctggctcgc cgctcagcca ggtagctag cgctcaacat | 1740 |
| ggggattgca aataaagtg | 1759 |

<210> SEQ ID NO 20
<211> LENGTH: 1008
<212> TYPE: DNA
<213> ORGANISM: Oryza sativa

<400> SEQUENCE: 20

| | | |
|---|---|---|
| atgaagcaag ttctggcccc cataatagcc ttggtcattg gaattggaac actagctttc | 60 |
| atggccatta gtcctcaggt ttgccatgct gctgcaggag gaagtgctac tgtggcgaga | 120 |
| agcatcttcg tcagcaagaa gggtagtggt gctgatttca aaggataca agacgccatc | 180 |
| aactccgtcc cattcgccaa ccggcggtgg atccggattc acatcgccgc cggcgtctac | 240 |
| aaggagaagg tgagcatacc ggcgaacaag agcttcatct tgctggaagg cgaggggagg | 300 |
| cagcagacgt cgatcgagtg gcggaccac gccggcggcg gcggcgggga ctccggcacg | 360 |
| gccgactcgc cgacgttcgc ctcgtacgcc gccgacttca tggcccgcga catcaccttc | 420 |
| aagaacacgt acgggaggat ggcgccggcg gtggcggcgc tggtggccgg agaccggtcg | 480 |
| gcgttctacc ggtgcggctt cgtggggctg caggacacgc tgagcgacct gctggggagg | 540 |
| cactactacg agcgctgcta cgtcgagggc gccgtcgact tcatcttcgg gaagcccag | 600 |
| tccatcttcc accgctgcca catctccacc gcggcggcgg cggcgccgg gttcatcacg | 660 |
| gcgcagggcc ggagcagcgc gtccgacgcg agcgggttcg tgttcacctc gtgcaccgtc | 720 |
| ggcggcgccg ccccggcgta cctggccgc gcgtggcgtg cctacgcgcg cgtcgtgttc | 780 |
| taccggacag ccatgtccgc cgccgtcgtc ggcctcggct gggacgcctg gactacaag | 840 |
| ggcaaagagg agacgctgga gatggtggag tcggggtgca cggggccggg gtcgaacagg | 900 |
| acggggaggg tgccatggga aagacgctg agcgggagg agctcgccaa gctcgtcgac | 960 |
| atctcgtacg tctcccgcga cggctggctc gccgctcagc cacggtag | 1008 |

<210> SEQ ID NO 21
<211> LENGTH: 335
<212> TYPE: PRT
<213> ORGANISM: Oryza sativa

<400> SEQUENCE: 21

Met Lys Gln Val Leu Ala Pro Ile Ile Ala Leu Val Ile Gly Ile Gly
1               5                   10                  15

Thr Leu Ala Phe Met Ala Ile Ser Pro Gln Val Cys His Ala Ala Ala
            20                  25                  30

Gly Gly Ser Ala Thr Val Ala Arg Ser Ile Phe Val Ser Lys Lys Gly
        35                  40                  45

Ser Gly Ala Asp Phe Thr Arg Ile Gln Asp Ala Ile Asn Ser Val Pro
    50                  55                  60

Phe Ala Asn Arg Arg Trp Ile Arg Ile His Ile Ala Ala Gly Val Tyr
65                  70                  75                  80

Lys Glu Lys Val Ser Ile Pro Ala Asn Lys Ser Phe Ile Leu Leu Glu
                85                  90                  95

Gly Glu Gly Arg Gln Gln Thr Ser Ile Glu Trp Ala Asp His Ala Gly
            100                 105                 110

Gly Gly Gly Gly Asp Ser Gly Thr Ala Asp Ser Pro Thr Phe Ala Ser
        115                 120                 125

Tyr Ala Ala Asp Phe Met Ala Arg Asp Ile Thr Phe Lys Asn Thr Tyr
    130                 135                 140

Gly Arg Met Ala Pro Ala Val Ala Ala Leu Val Ala Gly Asp Arg Ser
145                 150                 155                 160

Ala Phe Tyr Arg Cys Gly Phe Val Gly Leu Gln Asp Thr Leu Ser Asp
                165                 170                 175

Leu Leu Gly Arg His Tyr Tyr Glu Arg Cys Tyr Val Glu Gly Ala Val
            180                 185                 190

Asp Phe Ile Phe Gly Glu Ala Gln Ser Ile Phe His Arg Cys His Ile
        195                 200                 205

Ser Thr Ala Ala Ala Ala Pro Gly Phe Ile Thr Ala Gln Gly Arg
    210                 215                 220

Ser Ser Ala Ser Asp Ala Ser Gly Phe Val Phe Thr Ser Cys Thr Val
225                 230                 235                 240

Gly Gly Ala Ala Pro Ala Tyr Leu Gly Arg Ala Trp Arg Ala Tyr Ala
                245                 250                 255

Arg Val Val Phe Tyr Arg Thr Ala Met Ser Ala Val Val Gly Leu
            260                 265                 270

Gly Trp Asp Ala Trp Asp Tyr Lys Gly Lys Glu Glu Thr Leu Glu Met
        275                 280                 285

Val Glu Ser Gly Cys Thr Gly Pro Gly Ser Asn Arg Thr Gly Arg Val
    290                 295                 300

Pro Trp Glu Lys Thr Leu Ser Gly Glu Glu Leu Ala Lys Leu Val Asp
305                 310                 315                 320

Ile Ser Tyr Val Ser Arg Asp Gly Trp Leu Ala Ala Gln Pro Arg
                325                 330                 335

<210> SEQ ID NO 22
<211> LENGTH: 688
<212> TYPE: DNA
<213> ORGANISM: Oryza sativa

<400> SEQUENCE: 22
cttctcactc ttctcgcgtc cttgcaggct ttttcctcca tcgtcgtcag cccatcgatg      60
gcagttcgtc ccacatcgat tgccataggg gcagcatcaa tagatagcat catctcgatg     120
gtctgcgagc tcgagctcga gatgtggtat ttccccatct catgcgaatc ctttgagcct     180
tccggatgcc aactcctgaa gcgtccaggg cgtatccgtc tccatcgtca ggcgctgctg     240
ttgttcaaac aagctgatct accgtctctc cttttcaagg t gaacacctat gcccagtctt     300
cccttccaac cctgtttctt ctacttcacc ttcactccat cattccccat ttgcatgaat     360
accattttgt ttagttacat agttcaagtc gtcattcatt acttcgacaa acagtctgcc     420
gagttcatca actcagctgc tggggccatc accgtctcct acgtcatgca gctactgact     480
ggtaccatct ttatccatca ttaaataaaa acctggatcg atctatgaat atccctgat      540 cctaattttg catcttaata ttgaatcaac aatttatttt ctaaacttgg ctgcagggag     600
gatatgcata atgtgctttt tacagaggga caatgttcta ggtgtttgca aagagcgcgt     660
gtgagggaac aaatccatac taaggcag                                         688

<210> SEQ ID NO 23
<211> LENGTH: 396
<212> TYPE: DNA
<213> ORGANISM: Oryza sativa

<400> SEQUENCE: 23
atggcagttc gtcccacatc gattgccata ggggcagcat caatagatag catcatctcg      60
atggtctgcg agctcgagct cgagatgtgg tatttcccca tctcatgcga atcctttgag     120
ccttccggat gccaactcct gaagcgtcca gggcgtatcc gtctccatcg tcaggcgctg     180

```
ctgttgttca aacaagctga tctaccgtct ctcctttcaa gttacatagt tcaagtcgtc    240
attcattact tcgacaaaca gtctgccgag ttcatcaact cagctgctgg ggccatcacc    300
gtctcctacg tcatgcagct actgactggg aggatatgca taatgtgctt tttacagagg    360
gacaatgttc taggtgtttg caaagagcgc gtgtga                              396
```

<210> SEQ ID NO 24
<211> LENGTH: 131
<212> TYPE: PRT
<213> ORGANISM: Oryza sativa

<400> SEQUENCE: 24

```
Met Ala Val Arg Pro Thr Ser Ile Ala Ile Gly Ala Ala Ser Ile Asp
1               5                   10                  15

Ser Ile Ile Ser Met Val Cys Glu Leu Glu Leu Glu Met Trp Tyr Phe
            20                  25                  30

Pro Ile Ser Cys Glu Ser Phe Glu Pro Ser Gly Cys Gln Leu Leu Lys
        35                  40                  45

Arg Pro Gly Arg Ile Arg Leu His Arg Gln Ala Leu Leu Leu Phe Lys
    50                  55                  60

Gln Ala Asp Leu Pro Ser Leu Leu Ser Ser Tyr Ile Val Gln Val Val
65                  70                  75                  80

Ile His Tyr Phe Asp Lys Gln Ser Ala Glu Phe Ile Asn Ser Ala Ala
                85                  90                  95

Gly Ala Ile Thr Val Ser Tyr Val Met Gln Leu Leu Thr Gly Arg Ile
            100                 105                 110

Cys Ile Met Cys Phe Leu Gln Arg Asp Asn Val Leu Gly Val Cys Lys
        115                 120                 125

Glu Arg Val
    130
```

<210> SEQ ID NO 25
<211> LENGTH: 300
<212> TYPE: DNA
<213> ORGANISM: Oryza sativa

<400> SEQUENCE: 25

```
cagcgatgga tattgaaccg ggaggcggtg gcggcgtcga ggaggaggcg gcggcggtcg     60
ggaggcgacg gcttggagga ggaggaggcg gcgtcagcgg tggcggagga ggaggaggcg    120
acgacggcgg tggatctgag agagtgagag tgtgagagag tgagaggcgg cgtcggcggt    180
ggataaggac ccgtggatga ggattgacta agtaaaccct agtcaatcct catctctatc    240
gggcagacta ttatacccga tgcagatgac actcatccgt gacgggcgtt agtactctgc    300
```

<210> SEQ ID NO 26
<211> LENGTH: 165
<212> TYPE: DNA
<213> ORGANISM: Oryza sativa

<400> SEQUENCE: 26

```
atggatattg aaccgggagg cgtggcggc gtcgaggagg aggcggcggc ggtcgggagg      60
cgacggcttg gaggaggagg aggcggcgtc agcggtggcg gaggaggagg aggcgacgac    120
ggcggtggat ctgagagaat gacactcatc cgtgacgggc gttag                    165
```

<210> SEQ ID NO 27
<211> LENGTH: 54

```
<212> TYPE: PRT
<213> ORGANISM: Oryza sativa

<400> SEQUENCE: 27

Met Asp Ile Glu Pro Gly Gly Gly Gly Val Glu Glu Ala Ala
1               5                   10                  15

Ala Val Gly Arg Arg Leu Gly Gly Gly Gly Val Ser Gly
            20                  25                  30

Gly Gly Gly Gly Gly Asp Asp Gly Gly Ser Glu Arg Met Thr
        35                  40                  45

Leu Ile Arg Asp Gly Arg
    50

<210> SEQ ID NO 28
<211> LENGTH: 4245
<212> TYPE: DNA
<213> ORGANISM: Oryza sativa

<400> SEQUENCE: 28
catgtggagg ttgaaggttg cggagagcgg tggcacgccg ttgctgcggt cgacgaatgg      60
cttccttggg cgagcggtgt gggagttcga ccccgaccac ggcacgccgg aggaccgcgc     120
cgacgtcgag agggtgcgcc gtgagttcac cgaccaccgc cttcaccacc gggagtcagc     180
tgacctcctc atgcgcatgc aagtatatat taattacata cgctcattca tcccttagtt     240
ttttaaatat ataatgtcgc tattcgttta ttaataaaag tattcagttg ttatatactt     300
ctattttggt tatggttata tcatcactgc agtacattaa gaacgactta tatatagaga     360
gagaaagcat tatgaacggt caaatatatg tttaaaaatc aataatctca tatattaaag     420
aacaaaggaa gtaataaaca cgaatggctc tgtatctttc gaaaatcaat aaccacctca     480
tatattaaag aaaaaaggga gtaataaaca cgaatggttc tatatctctt atttgtatat     540
attatataat aattacttat tagttaaact gcaatttact ccaatacttt ttgagaaacg     600
caatttaccc caatatgaaa ctgtacggtg tgttcgcttt catttgattt tgttgcaggg     660
tttcgttcat ttcatacggt gttattttca tttccttttg tgttgcaatt tgcatagcaa     720
aacaagcatc aacgtcgtcg ttatcgtatt ccacccgtca ataataagct tggagagaag     780
gaggaggtga ctgaagaaat cgccatggct tcgttgagac gagctctcga cgagttctct     840
tctctgcaag cagacgacgg acactggcct ggagacttca gtggtgttat gttcatcatg     900
cctggcttgg tagtatattt aaattgtatc tgtctctggc taaataattt atgcttagct     960
atttcgtggt ttaatttctg gtgatctagc taatttctgt acaaataaat gcagatattt    1020
gccttatatg tcactggatc actggacact atcatatcac cagagcatcg gcgggagata    1080
tgtcgctata tctataacca tcaggcatat ttttttccgt atatatggac gactgaccat    1140
aaaataatta taatatgctc atgtattcat ggtttaataa ttttaattat agaagaacgt    1200
gtgttactcc agtacttgca gtacgaatgt ttataaaaac aaaaatgggt ggtttgcata    1260
aattaaagca cgagttcaga cttatttgct cagacaaaat ataagcatat ttttctaagt    1320
aacaattaaa tgtcattagt ataaaaaaca ctgagtaaat ttcccaaaac tacatataac    1380
ttaaccaaac tgtgtcaaaa ctatagattt aagataacgt atcacaaaac acaaatttac    1440
catcaaaatt atcattaaaa tattgcaaaa gtacatatct aataatgttt ttgtcacaag    1500
actataggtt ttatttaaat tactcgaact atatattatt atattagagt ataagttaat    1560
gatgaatttg gtgctaaacc tataatttgt tgataacttt attattaaat ctataatatt    1620
```

```
atgatactcg ctcttaaatc tgcaattccg cgataaattt aatattaatt ctatagtttt    1680
atgatacacc attttaaata tataatttta taatagcttg gttagagaat atgtaatttt    1740
gtgaaattca ctttaaaaac atttgatttt ccatattttg tgactgcaaa ttctgcacat    1800
gcatgtgtta tatagaacga ggatggtgga tggggcagtt tgatgttgag ctcgagcacc    1860
atgtttggca catgttcaaa ctatatcacc cttaggcttc tcggtgaaga gacaagcaat    1920
gagcaattag ccaaagggcg catatggatc atattgcatg gcggcactac ctttgttcca    1980
caatggggaa agatatggct ctcggtctgt ctactatatt atcgcatgaa tccacacaat    2040
aatgaatttt gctaaacaat tgctttcgtt gatttttgta gggttcagtt tactttcgaa    2100
acatcttgat ttatataaac atgactaata taatggttaa ctaaatgata ggtatattta    2160
gcactttcta atcgtaccaa ccgattcata ttttaattaa agtactttca cacgattggt    2220
tttatagtac aaggttttca ctttcgcgcc aaaaatttcg gccattttgg tagaaacgaa    2280
atttctggat ttttgggatt ttcggcgttt tttagaccat ttttttgaaat tttaacacaa    2340 tttaactgaa tttgactaaa ttcacaaaaa agttagaaaa atcgaaaatt tcaaccgaga    2400
taatcatttg cctgggtaag aattggaggc agggttcaat ctatcgggaa ggggaaaaat    2460 ttcagggtc accgaaattt cgaaaatctt tcagaaattt cgaacggaat tttcaaacaa    2520
aatttgaatt taaacaataa aaataaagaa attttaccaa gatcagagta tagatgagca    2580
tcgagtctat tcaatccaaa gcagaggaac aggagattga aacacagtaa cacgtaagga    2640
tgcgaggctt gtgcggcttg tgtcgtcgtc cggtcatcgt cgtgctgccg aagagcgatg    2700
gagccgccag cggcaactct agccaaacgg aggatgcgag gcccgcggct tgtatcgtcg    2760
tcgtggtgcc gaagagccac ggagacgccg ccggccactc caaccaaccc gccgcctccg    2820
gttccggcca ccgccgcggc cgctgttcgc tagcttggga ggatggcgac ctgctgcctg    2880
ctgggcgagc tgtcggagga tagcgaagca gcagcagcct ttggtatata agtgaggagg    2940
ggataggaaa ttgaggattt ttaccatgaa cattgttttg ccgaaatttt tgaccggagc    3000
tcatgtttat caggacccac caatagaccc gaaatttcgt aaatttcgtt ccgaaatttt    3060
gaaccctgat tagagggaag gtagaaaaaa aaagcccaaa aggcaaaaag aaaggagaaa    3120
aaacgaaata agaaaagaaa aacggcggaa aaaaacctaa gcccgaaaaa aaaagggacg    3180
gaggaaaaga aaaagatgg aaaaagaaa ataacagcga aaaagaaaa aaggacaaaa    3240 agagaaccgg aaaccttaat tattatatat ataggtataa aaaagaaaaa acagcgaaaa    3300
aagaaaaaaa cggacggaaa gagaacagga aaccttactt atttttctta ttaggtatag    3360
ataagccata tgactttttt ctagtcaaac ttctttaagt ttgaccaatt ttatataaaa    3420
atttagtagt attttcaaca caaaacaaac atattatcag aatatattca atgttatatt    3480
taatgaaact aatttgatat tttagatgtt gttaaatttt tctataaatt tgggccaact    3540
tgacaaagtt taattatgaa aaaaatcaaa cgacttataa tataacgcgt tgattgattt    3600
cggacaaatt aatttgattc actacagata cttggagtgt acgagtgggc aggaaacaac    3660
cccatcttcc ctgagctatg gctgacccca caatttcttc cttttcatcc aggtatatat    3720
atactagtaa taatcatact gtatactcct acatcaaata gtagctagtt gcacacaaat    3780
caaaaacagt ttaatggcaa tgcctggagt ttatatcaga cttaaggttc atgaaaattc    3840
tttaattttg aactgaattt acttttgtgc aggcaaattc tggtgcttaa ctcgcatggt    3900 ataccctgccg atggcctacc tatacggcaa gaagttcgtg ggccccaccg cgccgaccat    3960
cctggcgctg cgagaggaga tttactcggc ccactacctc acaatcgatt gggcccaggc    4020
```

```
ccgcagcgcc tgcgccaagg taattttttgg gccgggccga atttgttggg cttcttgttg    4080
ggggaggagt gccccgcgag gagaattttt tttatttata attttttta ttaaaagtttg    4140 tacaaaaata attttccatt ttgaaaattg acgaatgtag tcgcctaccg ccctctggga    4200
gggcgatttt taaaaatcgc cctctcagag ggcggcgaaa atgac                     4245

<210> SEQ ID NO 29
<211> LENGTH: 867
<212> TYPE: DNA
<213> ORGANISM: Oryza sativa

<400> SEQUENCE: 29
atgtggaggt tgaaggttgc ggagagcggt ggcacgccgt tgctgcggtc gacgaatggc     60
ttccttgggc gagcggtgtg ggagttcgac cccgaccacg gcacgccgga ggaccgcgcc    120
gacgtcgaga gggtgcgccg tgagttcacc gaccaccgcc ttcaccaccg ggagtcagct    180
gacctcctca tgcgcatgca acaaaacaag catcaacgtc gtcgttatcg tattccaccc    240
gtcaataata agcttggaga aggaggag gtgactgaag aaatcgccat ggcttcgttg    300
agacgagctc tcgacgagtt ctcttctctg caagcagacg acggacactg gcctggagac    360
ttcagtggtg ttatgttcat catgcctggc ttgaacgagg atggtggatg gggcagtttg    420
atgttgagct cgagcaccat gtttggcaca tgttcaaact atatcaccct taggcttctc    480
ggtgaagaga caagcaatga gcaattagcc aaagggcgca tatggatcat attgcatggc    540
ggcactacct ttgttccaca atgggggaaag atatggctct cgatacttgg agtgtacgag    600
tgggcaggaa acaaccccat cttccctgag ctatggctga ccccacaatt tcttcctttt    660
catccaggca aattctggtg cttaactcgc atggtatacc tgccgatggc ctacctatac    720
ggcaagaagt tcgtgggccc caccgcgccg accatcctgg cgctgcgaga ggagatttac    780
tcggcccact acctcacaat cgattgggcc caggcccgca gcgcctgcgc caagtcgcct    840
accgccctct gggagggcga ttttttaa                                       867

<210> SEQ ID NO 30
<211> LENGTH: 288
<212> TYPE: PRT
<213> ORGANISM: Oryza sativa

<400> SEQUENCE: 30

Met Trp Arg Leu Lys Val Ala Glu Ser Gly Gly Thr Pro Leu Leu Arg
1               5                   10                  15

Ser Thr Asn Gly Phe Leu Gly Arg Ala Val Trp Glu Phe Asp Pro Asp
            20                  25                  30

His Gly Thr Pro Glu Asp Arg Ala Asp Val Glu Arg Val Arg Arg Glu
        35                  40                  45

Phe Thr Asp His Arg Leu His His Arg Glu Ser Ala Asp Leu Leu Met
    50                  55                  60

Arg Met Gln Gln Asn Lys His Gln Arg Arg Tyr Arg Ile Pro Pro
65                  70                  75                  80

Val Asn Asn Lys Leu Gly Glu Lys Glu Val Thr Glu Glu Ile Ala
                85                  90                  95

Met Ala Ser Leu Arg Arg Ala Leu Asp Glu Phe Ser Ser Leu Gln Ala
            100                 105                 110

Asp Asp Gly His Trp Pro Gly Asp Phe Ser Gly Val Met Phe Ile Met
        115                 120                 125
```

```
Pro Gly Leu Asn Glu Asp Gly Gly Trp Gly Ser Leu Met Leu Ser Ser
    130                 135                 140

Ser Thr Met Phe Gly Thr Cys Ser Asn Tyr Ile Thr Leu Arg Leu Leu
145                 150                 155                 160

Gly Glu Glu Thr Ser Asn Glu Gln Leu Ala Lys Gly Arg Ile Trp Ile
                165                 170                 175

Ile Leu His Gly Gly Thr Thr Phe Val Pro Gln Trp Gly Lys Ile Trp
            180                 185                 190

Leu Ser Ile Leu Gly Val Tyr Glu Trp Ala Gly Asn Asn Pro Ile Phe
        195                 200                 205

Pro Glu Leu Trp Leu Thr Pro Gln Phe Leu Pro Phe His Pro Gly Lys
    210                 215                 220

Phe Trp Cys Leu Thr Arg Met Val Tyr Leu Pro Met Ala Tyr Leu Tyr
225                 230                 235                 240

Gly Lys Lys Phe Val Gly Pro Thr Ala Pro Thr Ile Leu Ala Leu Arg
                245                 250                 255

Glu Glu Ile Tyr Ser Ala His Tyr Leu Thr Ile Asp Trp Ala Gln Ala
            260                 265                 270

Arg Ser Ala Cys Ala Lys Ser Pro Thr Ala Leu Trp Glu Gly Asp Phe
        275                 280                 285

<210> SEQ ID NO 31
<211> LENGTH: 27
<212> TYPE: DNA
<213> ORGANISM: Artificial Sequence
<220> FEATURE:
<223> OTHER INFORMATION: Forward primer for cloning cDNA of OsCCP1 gene

<400> SEQUENCE: 31
cacttcctag caattaagat catggtg                                          27

<210> SEQ ID NO 32
<211> LENGTH: 25
<212> TYPE: DNA
<213> ORGANISM: Artificial Sequence
<220> FEATURE:
<223> OTHER INFORMATION: Reverse primer for cloning cDNA of OsCCP1 gene

<400> SEQUENCE: 32
ctggagatgg aggatggata ttgtc                                            25

<210> SEQ ID NO 33
<211> LENGTH: 31
<212> TYPE: DNA
<213> ORGANISM: Artificial Sequence
<220> FEATURE:
<223> OTHER INFORMATION: Forward primer for cloning cDNA of OsGPR89A
      gene

<400> SEQUENCE: 33
ctgctgaggt ttccccttgc gagatccatc t                                     31

<210> SEQ ID NO 34
<211> LENGTH: 33
<212> TYPE: DNA
<213> ORGANISM: Artificial Sequence
<220> FEATURE:
<223> OTHER INFORMATION: Reverse primer for cloning cDNA of OsGPR89A
      gene

<400> SEQUENCE: 34
ccgctgaggt gtggacacaa cattacaacc ggc                                   33
```

<210> SEQ ID NO 35
<211> LENGTH: 23
<212> TYPE: DNA
<213> ORGANISM: Artificial Sequence
<220> FEATURE:
<223> OTHER INFORMATION: Forward primer for cloning cDNA of OsDN-DTP13
       gene

<400> SEQUENCE: 35
cacctcgtgt gctacaagtg cta                                           23

<210> SEQ ID NO 36
<211> LENGTH: 25
<212> TYPE: DNA
<213> ORGANISM: Artificial Sequence
<220> FEATURE:
<223> OTHER INFORMATION: Reverse primer for cloning cDNA of OsDN-DTP13
       gene

<400> SEQUENCE: 36
gggagtagct aaaagtggtt cagtg                                         25

<210> SEQ ID NO 37
<211> LENGTH: 31
<212> TYPE: DNA
<213> ORGANISM: Artificial Sequence
<220> FEATURE:
<223> OTHER INFORMATION: Forward primer for cloning cDNA of OsCTPS1 gene

<400> SEQUENCE: 37
ctgctgaggc gatgaagtac gtgctggtga c                                  31

<210> SEQ ID NO 38
<211> LENGTH: 35
<212> TYPE: DNA
<213> ORGANISM: Artificial Sequence
<220> FEATURE:
<223> OTHER INFORMATION: Reverse primer for cloning cDNA of OsCTPS1 gene

<400> SEQUENCE: 38
ccgctgaggg ctatgctgct aagtatgaag aatgc                              35

<210> SEQ ID NO 39
<211> LENGTH: 31
<212> TYPE: DNA
<213> ORGANISM: Artificial Sequence
<220> FEATURE:
<223> OTHER INFORMATION: Forward primer for cloning gDNA of OsDN-DTP14
       gene

<400> SEQUENCE: 39
ctgctgaggc ggaggcagtg acaacgacag c                                  31

<210> SEQ ID NO 40
<211> LENGTH: 33
<212> TYPE: DNA
<213> ORGANISM: Artificial Sequence
<220> FEATURE:
<223> OTHER INFORMATION: Reverse primer for cloning gDNA of OsDN-DTP14
       gene

<400> SEQUENCE: 40
ccgctgaggg atcctcaaac gacgtctcca ggg                                33

<210> SEQ ID NO 41

```
<211> LENGTH: 35
<212> TYPE: DNA
<213> ORGANISM: Artificial Sequence
<220> FEATURE:
<223> OTHER INFORMATION: Forward primer for cloning gDNA of OsLPA1 gene

<400> SEQUENCE: 41
ctgctgaggc cttcctcctc tctctctcac tcttg                              35

<210> SEQ ID NO 42
<211> LENGTH: 33
<212> TYPE: DNA
<213> ORGANISM: Artificial Sequence
<220> FEATURE:
<223> OTHER INFORMATION: Reverse primer for cloning gDNA of OsLPA1 gene

<400> SEQUENCE: 42
ccgctgagga gctcctccca agtccaaatc cac                                33

<210> SEQ ID NO 43
<211> LENGTH: 36
<212> TYPE: DNA
<213> ORGANISM: Artificial Sequence
<220> FEATURE:
<223> OTHER INFORMATION: Forward primer for cloning gDNA of OsPE1 gene

<400> SEQUENCE: 43
ctgctgaggg atctatcaag tttgtcaggc gagatg                             36

<210> SEQ ID NO 44
<211> LENGTH: 34
<212> TYPE: DNA
<213> ORGANISM: Artificial Sequence
<220> FEATURE:
<223> OTHER INFORMATION: Reverse primer for cloning gDNA of OsPE1 gene

<400> SEQUENCE: 44
ccgctgaggc actttatttg caatccccat gttg                               34

<210> SEQ ID NO 45
<211> LENGTH: 33
<212> TYPE: DNA
<213> ORGANISM: Artificial Sequence
<220> FEATURE:
<223> OTHER INFORMATION: Forward primer for cloning gDNA of OsDN-DTP15
      gene

<400> SEQUENCE: 45
ctgctgaggc ttctcactct tctcgcgtcc ttg                                33

<210> SEQ ID NO 46
<211> LENGTH: 37
<212> TYPE: DNA
<213> ORGANISM: Artificial Sequence
<220> FEATURE:
<223> OTHER INFORMATION: Reverse primer for cloning gDNA of OsDN-DTP15
      gene

<400> SEQUENCE: 46
ccgctgaggc tgccttagta tggatttgtt ccctcac                            37

<210> SEQ ID NO 47
<211> LENGTH: 33
<212> TYPE: DNA
<213> ORGANISM: Artificial Sequence
<220> FEATURE:
<223> OTHER INFORMATION: Forward primer for cloning gDNA of OsDN-DTP16
```

```
                                gene

<400> SEQUENCE: 47
ctgctgaggc agcgatggat attgaaccgg gag                                   33

<210> SEQ ID NO 48
<211> LENGTH: 32
<212> TYPE: DNA
<213> ORGANISM: Artificial Sequence
<220> FEATURE:
<223> OTHER INFORMATION: Reverse primer for cloning gDNA of OsDN-DTP16
      gene

<400> SEQUENCE: 48
ccgctgaggg cagagtacta acgcccgtca cg                                    32

<210> SEQ ID NO 49
<211> LENGTH: 34
<212> TYPE: DNA
<213> ORGANISM: Artificial Sequence
<220> FEATURE:
<223> OTHER INFORMATION: Forward primer for cloning gDNA of OsCAS2 gene

<400> SEQUENCE: 49
ctgctgaggc atgtggaggt tgaaggttgc ggag                                  34

<210> SEQ ID NO 50
<211> LENGTH: 33
<212> TYPE: DNA
<213> ORGANISM: Artificial Sequence
<220> FEATURE:
<223> OTHER INFORMATION: Reverse primer for cloning gDNA of OsCAS2 gene

<400> SEQUENCE: 50
ccgctgaggg tcattttcgc cgccctctga gag                                   33

<210> SEQ ID NO 51
<211> LENGTH: 21
<212> TYPE: DNA
<213> ORGANISM: Artificial Sequence
<220> FEATURE:
<223> OTHER INFORMATION: Forward primer for real-time PCR analysis of
      OsLPA1 gene

<400> SEQUENCE: 51
tggcacaaac tcgatagcta c                                                21

<210> SEQ ID NO 52
<211> LENGTH: 18
<212> TYPE: DNA
<213> ORGANISM: Artificial Sequence
<220> FEATURE:
<223> OTHER INFORMATION: Reverse primer for real-time PCR analysis of
      OsLPA1 gene

<400> SEQUENCE: 52
ccgcccgttg atttcgag                                                    18

<210> SEQ ID NO 53
<211> LENGTH: 1080
<212> TYPE: DNA
<213> ORGANISM: Oryza sativa

<400> SEQUENCE: 53
atggcgtccg tggatctgac cccgaggcag gcgaggaagg cgtacggcgg cgatggtggg      60
```

-continued

| | |
|---|---|
| acctactacg agtggagccc cgcagacctg cccatgctgg aactcgccaa catcggcggc | 120 |
| gccaagctgt cgctcaacgc cggtggcctc gccctgccca gcttttccga ctccggaaag | 180 |
| gttgcgtatg ttcttcaagg caagggcact tgtggcattg tcctgccgga ggcgagcaag | 240 |
| gagaaggtga tcgccgtgaa ggagggagac tccctggcac tccccttggg cgtggtgaca | 300 |
| tggtggcata acctcccgga gtccccaatc gagctcgtca tcctcttcct cggcgacaca | 360 |
| tcgaaggcgc acaaggccgg ccaattcaca aacatgcagc tcaccggtgc caccggcatc | 420 |
| ttcaccggct ctccacgga gttcgtcggc cgcgcatggg acctcgccga gtccgacgcc | 480 |
| gtcaagctcg tgtccagcca gcctgcctcc ggcatcgtca agatcaagtc cggccagaag | 540 |
| ctccccgagc cgtcggccgc cgaccgcgag ggcatggcgc tcaactgcct ggaggcgccg | 600 |
| ctcgacgtgg acatcaagaa cggcggccgc gtggtggtgc tcaacacggc gaacctgccg | 660 |
| atggtgaagg aggtcgggct cggcgccgac ctggtgagga tcgacggcca ctccatgtgc | 720 |
| tcgccggggt tctcgtgcga ctcggcgtac caggtcacct acttcatccg cggcagcggc | 780 |
| cgcgtccagg tggtcggcgc cgacgggaag cgcgtgctgg acacccacgt cgagggcggc | 840 |
| aacctgttca tcgtgccgcg cttctgcgtc gtctccaaga tcgccgacgc ctccggcctg | 900 |
| cagtggttct ccattatcac cacaccaaac ccgatcttca gtcacctggc ggggaagacg | 960 |
| tcggtgtgga aggcgatctc gccggaggtg ctggaggcgt cgttcaacgc gacgccggag | 1020 |
| atggagaagc tgttccggtc caaaaggatc gactcggaga tcttcttcgc gcccaactga | 1080 |

<210> SEQ ID NO 54
<211> LENGTH: 359
<212> TYPE: PRT
<213> ORGANISM: Oryza sativa

<400> SEQUENCE: 54

Met Ala Ser Val Asp Leu Thr Pro Arg Gln Ala Arg Lys Ala Tyr Gly
1               5                   10                  15

Gly Asp Gly Gly Thr Tyr Tyr Glu Trp Ser Pro Ala Asp Leu Pro Met
            20                  25                  30

Leu Glu Leu Ala Asn Ile Gly Gly Ala Lys Leu Ser Leu Asn Ala Gly
        35                  40                  45

Gly Leu Ala Leu Pro Ser Phe Ser Asp Ser Gly Lys Val Ala Tyr Val
    50                  55                  60

Leu Gln Gly Lys Gly Thr Cys Gly Ile Val Leu Pro Glu Ala Ser Lys
65                  70                  75                  80

Glu Lys Val Ile Ala Val Lys Glu Gly Asp Ser Leu Ala Leu Pro Phe
                85                  90                  95

Gly Val Val Thr Trp Trp His Asn Leu Pro Glu Ser Pro Ile Glu Leu
            100                 105                 110

Val Ile Leu Phe Leu Gly Asp Thr Ser Lys Ala His Lys Ala Gly Gln
        115                 120                 125

Phe Thr Asn Met Gln Leu Thr Gly Ala Thr Gly Ile Phe Thr Gly Phe
    130                 135                 140

Ser Thr Glu Phe Val Gly Arg Ala Trp Asp Leu Ala Glu Ser Asp Ala
145                 150                 155                 160

Val Lys Leu Val Ser Ser Gln Pro Ala Ser Gly Ile Val Lys Ile Lys
                165                 170                 175

Ser Gly Gln Lys Leu Pro Glu Pro Ser Ala Ala Asp Arg Glu Gly Met
            180                 185                 190

Ala Leu Asn Cys Leu Glu Ala Pro Leu Asp Val Asp Ile Lys Asn Gly

|  | 195 |  |  | 200 |  |  | 205 |  |  |
|---|---|---|---|---|---|---|---|---|---|

Gly Arg Val Val Leu Asn Thr Ala Asn Leu Pro Met Val Lys Glu
    210                      215                  220

Val Gly Leu Gly Ala Asp Leu Val Arg Ile Asp Gly His Ser Met Cys
225                    230                  235              240

Ser Pro Gly Phe Ser Cys Asp Ser Ala Tyr Gln Val Thr Tyr Phe Ile
            245                  250                255

Arg Gly Ser Gly Arg Val Gln Val Gly Ala Asp Gly Lys Arg Val
          260                  265                270

Leu Asp Thr His Val Glu Gly Gly Asn Leu Phe Ile Val Pro Arg Phe
        275                  280                285

Cys Val Val Ser Lys Ile Ala Asp Ala Ser Gly Leu Gln Trp Phe Ser
290                    295                  300

Ile Ile Thr Thr Pro Asn Pro Ile Phe Ser His Leu Ala Gly Lys Thr
305                  310                315              320

Ser Val Trp Lys Ala Ile Ser Pro Glu Val Leu Glu Ala Ser Phe Asn
          325                  330              335

Ala Thr Pro Glu Met Glu Lys Leu Phe Arg Ser Lys Arg Ile Asp Ser
        340                  345              350

Glu Ile Phe Phe Ala Pro Asn
      355

<210> SEQ ID NO 55
<211> LENGTH: 1119
<212> TYPE: DNA
<213> ORGANISM: Zea mays

<400> SEQUENCE: 55

```
atggtgcacc ggacttccat agccgatgtg catgtgatgt gcatggatct aagcccaaag    60
aaacccaaca aggccagcgc cagcgacggc ggagcctact acgactggtc ccccgccgat   120
ctgcccatgc tcggcgttgc ctccattggt gccgccaagc tctgcctcac cgccggaggt   180
cttgccctac ccagctactc cgactctgcc aagatcgcct acgtcctcca aggcaaaggt   240
atattcggcg tggttctccc ggaggcgacc aaggagaagg tcatctccgt caaggaaggc   300
gacgcgctgg cgctcccctt cggcgtcgtc acctggtggc acaacaacgc cgacgccgct   360
atctccgacc tcgtggtgct cttcctcggc gacacctcca cgggccacaa gccgggccag   420
ttcacaaaact tccagctcac cggctccacg ggcatcttca cgggcttctc cacagagttc   480
gttgcccgcg catgggacct cacccaggac gacgccgcca agctcgtctc cacccagccc   540
ggatccggca ttgtcagggt caaggacggg cacaagatgc ccgaggcgcg cgacgaggac   600
aggcagggcc tggtcctcaa ctgcctagag gcgccgcttg acgtcgacat caagaacgga   660
gggcgcgtcg tggtcctcaa cacccagaac ctgccgctcg tcaaggaggt cgggctcggt   720
gctgaccttg tcaggatcga cgcccactcc atgtgctcgc ccggcttctc ctgcgactcc   780
gcctaccagg tcacctacat cgtgcgcggc agtggccgcg tccaggttgt tgggatcgac   840
ggcacgcgag tgctcgagac ccgcgccgag ggaggctgcc tcttcatcgt gccaaggttc   900
ttcgttgtct caaagatcgc cgacgaaacc ggcatggagt ggttctccat catcaccacc  960
cccaacccaa tctttagcca cttggcgggc cggacatcgg tgtggaaggc aatatctccg  1020
gcggtcttgc agtcgtcgtt caacaccacg ccggagatgg agaagctgtt ccgtagcaag  1080
aggcttgact cggagatctt ctttgcgcct tcaaactga                          1119
```

```
<210> SEQ ID NO 56
<211> LENGTH: 372
<212> TYPE: PRT
<213> ORGANISM: Zea mays

<400> SEQUENCE: 56

Met Val His Arg Thr Ser Ile Ala Asp Val His Val Met Cys Met Asp
1               5                   10                  15

Leu Ser Pro Lys Lys Pro Asn Lys Ala Ser Ala Ser Asp Gly Gly Ala
            20                  25                  30

Tyr Tyr Asp Trp Ser Pro Ala Asp Leu Pro Met Leu Gly Val Ala Ser
        35                  40                  45

Ile Gly Ala Ala Lys Leu Cys Leu Thr Ala Gly Gly Leu Ala Leu Pro
    50                  55                  60

Ser Tyr Ser Asp Ser Ala Lys Ile Ala Tyr Val Leu Gln Gly Lys Gly
65                  70                  75                  80

Ile Phe Gly Val Val Leu Pro Glu Ala Thr Lys Glu Lys Val Ile Ser
                85                  90                  95

Val Lys Glu Gly Asp Ala Leu Ala Leu Pro Phe Gly Val Val Thr Trp
            100                 105                 110

Trp His Asn Asn Ala Asp Ala Ala Ile Ser Asp Leu Val Val Leu Phe
        115                 120                 125

Leu Gly Asp Thr Ser Thr Gly His Lys Pro Gly Gln Phe Thr Asn Phe
    130                 135                 140

Gln Leu Thr Gly Ser Thr Gly Ile Phe Thr Gly Phe Ser Thr Glu Phe
145                 150                 155                 160

Val Ala Arg Ala Trp Asp Leu Thr Gln Asp Ala Ala Lys Leu Val
                165                 170                 175

Ser Thr Gln Pro Gly Ser Gly Ile Val Arg Val Lys Asp Gly His Lys
            180                 185                 190

Met Pro Glu Ala Arg Asp Glu Asp Arg Gln Gly Leu Val Leu Asn Cys
        195                 200                 205

Leu Glu Ala Pro Leu Asp Val Asp Ile Lys Asn Gly Gly Arg Val Val
    210                 215                 220

Val Leu Asn Thr Gln Asn Leu Pro Leu Val Lys Glu Val Gly Leu Gly
225                 230                 235                 240

Ala Asp Leu Val Arg Ile Asp Ala His Ser Met Cys Ser Pro Gly Phe
                245                 250                 255

Ser Cys Asp Ser Ala Tyr Gln Val Thr Tyr Ile Val Arg Gly Ser Gly
            260                 265                 270

Arg Val Gln Val Val Gly Ile Asp Gly Thr Arg Val Leu Glu Thr Arg
        275                 280                 285

Ala Glu Gly Gly Cys Leu Phe Ile Val Pro Arg Phe Phe Val Val Ser
    290                 295                 300

Lys Ile Ala Asp Glu Thr Gly Met Glu Trp Phe Ser Ile Ile Thr Thr
305                 310                 315                 320

Pro Asn Pro Ile Phe Ser His Leu Ala Gly Arg Thr Ser Val Trp Lys
                325                 330                 335

Ala Ile Ser Pro Ala Val Leu Gln Ser Ser Phe Asn Thr Thr Pro Glu
            340                 345                 350

Met Glu Lys Leu Phe Arg Ser Lys Arg Leu Asp Ser Glu Ile Phe Phe
        355                 360                 365

Ala Pro Ser Asn
    370
```

<210> SEQ ID NO 57
<211> LENGTH: 1128
<212> TYPE: DNA
<213> ORGANISM: Sorghum bicolor

<400> SEQUENCE: 57

| | | |
|---|---|---|
| atggtgcagc ggacttccac cgcccaagtg atgtccatgg acctcagccc aaagaaaccc | 60 |
| aacaaggcct acggcagcga tggcggcgcc tactacgact ggtccccccgc cgacctgccc | 120 |
| atgctcggcg ctgcctccat tggcgccgcc aagctctgcc tctccgccgg aggccttgct | 180 |
| ctgcctagct actctgactc tgccaaggtc gcctacgtcc tccaaggtaa gggtacgtgc | 240 |
| ggcgtggttc tgccggaggc gaccaaggag aaggtgatcc ccgtgaagga gggtgactcg | 300 |
| ctcgcgctcc ctttcggcgt cgtcacctgg tggcacaacg cgcacgccgc ctgcagcagc | 360 |
| tccgactccg acgacctcgt ggtcctcttc ctcggcgaca cgtccacggg ccacaagcgg | 420 |
| ggccagttca ccaacttcca gctcaccggc tccacgggca tcttcacggg cctgtccacc | 480 |
| gagttcgtcg cccgcgcatg ggacctcacc ccggacgccg ccgccgagct cgtctcctcc | 540 |
| cagcccggcg ccggcatcat cagggtcaag gacgggcacc ggatgcccca ggcccgcgac | 600 |
| gaggacaggg agggcatggt cctcaactgc ctggaggcgc cgctcgacgt cgacatcaag | 660 |
| aacgggggcc gcgtcgtcgt cctcaacacc cggaacctgc cgctcgtgga ggaggtcggt | 720 |
| ctcggcgccg acctcgtcag gatcgacgcg cactccatgt gctcgccggg gttctcctgc | 780 |
| gactccgcct accaggtcac ctacatcgtg cgcggcagtg gccgcgtcca ggtcgttggg | 840 |
| atcgacggca cgcgggtgct ggagacccgc gccgagggag gctgcctctt catcgtgccc | 900 |
| aggttcttcg ttgtctccaa gatcgccgac gaaactggca tggagtggtt ctccatcatc | 960 |
| accaccccca acccaatctt tagccacttg gcgggcagga catcggtgtg gaaggcaata | 1020 |
| tctcctgcgg tcctggaggc gtcgttcaac accacgccgg agaaggagaa gctgttccgt | 1080 |
| tccaagaggc ttgactcgga gatcttcttc gcgcctgctt caaactaa | 1128 |

<210> SEQ ID NO 58
<211> LENGTH: 375
<212> TYPE: PRT
<213> ORGANISM: Sorghum bicolor

<400> SEQUENCE: 58

Met Val Gln Arg Thr Ser Thr Ala Gln Val Met Ser Met Asp Leu Ser
1               5                   10                  15

Pro Lys Lys Pro Asn Lys Ala Tyr Gly Ser Asp Gly Gly Ala Tyr Tyr
            20                  25                  30

Asp Trp Ser Pro Ala Asp Leu Pro Met Leu Gly Ala Ala Ser Ile Gly
        35                  40                  45

Ala Ala Lys Leu Cys Leu Ser Ala Gly Gly Leu Ala Leu Pro Ser Tyr
    50                  55                  60

Ser Asp Ser Ala Lys Val Ala Tyr Val Leu Gln Gly Lys Gly Thr Cys
65                  70                  75                  80

Gly Val Val Leu Pro Glu Ala Thr Lys Glu Lys Val Ile Pro Val Lys
                85                  90                  95

Glu Gly Asp Ser Leu Ala Leu Pro Phe Gly Val Val Thr Trp Trp His
            100                 105                 110

Asn Ala His Ala Ala Cys Ser Ser Ser Asp Ser Asp Asp Leu Val Val
        115                 120                 125

Leu Phe Leu Gly Asp Thr Ser Thr Gly His Lys Arg Gly Gln Phe Thr

```
                130              135               140
Asn Phe Gln Leu Thr Gly Ser Thr Gly Ile Phe Thr Gly Leu Ser Thr
145                 150                 155                 160
Glu Phe Val Ala Arg Ala Trp Asp Leu Thr Pro Asp Ala Ala Ala Glu
                165                 170                 175
Leu Val Ser Ser Gln Pro Gly Ala Gly Ile Ile Arg Val Lys Asp Gly
                180                 185                 190
His Arg Met Pro Gln Ala Arg Asp Glu Asp Arg Glu Gly Met Val Leu
                195                 200                 205
Asn Cys Leu Glu Ala Pro Leu Asp Val Asp Ile Lys Asn Gly Gly Arg
210                 215                 220
Val Val Val Leu Asn Thr Arg Asn Leu Pro Leu Val Glu Glu Val Gly
225                 230                 235                 240
Leu Gly Ala Asp Leu Val Arg Ile Asp Ala His Ser Met Cys Ser Pro
                245                 250                 255
Gly Phe Ser Cys Asp Ser Ala Tyr Gln Val Thr Tyr Ile Val Arg Gly
                260                 265                 270
Ser Gly Arg Val Gln Val Gly Ile Asp Gly Thr Arg Val Leu Glu
                275                 280                 285
Thr Arg Ala Glu Gly Gly Cys Leu Phe Ile Val Pro Arg Phe Phe Val
290                 295                 300
Val Ser Lys Ile Ala Asp Glu Thr Gly Met Glu Trp Phe Ser Ile Ile
305                 310                 315                 320
Thr Thr Pro Asn Pro Ile Phe Ser His Leu Ala Gly Arg Thr Ser Val
                325                 330                 335
Trp Lys Ala Ile Ser Pro Ala Val Leu Glu Ala Ser Phe Asn Thr Thr
                340                 345                 350
Pro Glu Lys Glu Lys Leu Phe Arg Ser Lys Arg Leu Asp Ser Glu Ile
                355                 360                 365
Phe Phe Ala Pro Ala Ser Asn
370                 375
```

<210> SEQ ID NO 59
<211> LENGTH: 1071
<212> TYPE: DNA
<213> ORGANISM: Arabidopsis thaliana

<400> SEQUENCE: 59

| | | | | | |
|---|---|---|---|---|---|
| atggaattgg | atctatcacc | aaggctcccg | aaaaaggtgt | acggaggaga | cggtggttcg | 60 |
| tactttgcat | ggtgccctga | agagttgcca | atgctccgag | atggtaacat | ggagcctct | 120 |
| aagctcgctc | ttgagaagta | tggcttggct | cttcctcgct | actctgactc | ccccaaggtc | 180 |
| gcttatgttc | ttcaaggagc | tggaacagct | ggaatcgtgc | tccctgagaa | ggaggagaaa | 240 |
| gtgatagcaa | tcaagaaagg | agactccata | gctttacctt | tggtgtagt | gacatggtgg | 300 |
| ttcaacaatg | aggacactga | gctagtcgtt | ctcttccttg | gtgagactca | aagggtcac | 360 |
| aaagctggac | agttcaccga | cttttaccta | accggatcca | atggaatctt | caccggtttc | 420 |
| tctactgagt | ttgttggcag | agcttgggat | ctcgatgaga | ccaccgtgaa | gaagcttgtc | 480 |
| ggatctcaga | caggtaacgg | tatcgtgaag | gttgatgcga | gcttgaagat | gcctgaacca | 540 |
| aagaaaggtg | accgaaaagg | gtttgttttg | aactgtttgg | aggctcctct | tgatgttgac | 600 |
| attaaggatg | aggaagagt | tgttgtgttg | aacacaaaga | atcttccttt | ggttggtgaa | 660 |
| gttggatttg | gagctgatct | tgtgagaatc | gatggacact | ctatgtgttc | tcctggattc | 720 |

-continued

```
tcttgtgact cggctcttca agttacttac attgttggtg gaagtggtcg tgttcagatt    780
gttggtgctg atgggaagag agttcttgag actcatgtga aagctggtgt tttgttcatt    840
gttcctaggt tctttgttgt ctccaagatt gctgattctg atggcttgtc ttggttctcc    900
attgtgacca ctcctgatcc aatattcact catttggccg ggaggacttc ggtgtggaag    960
gctttgtcgc cggaggtttt gcaggcagcg ttcaaggtgg atcccgaggt tgagaaggct   1020
ttccgatcta agaggacctc tgatgccatt ttcttctctc cttccaacta g            1071
```

<210> SEQ ID NO 60
<211> LENGTH: 356
<212> TYPE: PRT
<213> ORGANISM: Arabidopsis thaliana

<400> SEQUENCE: 60

```
Met Glu Leu Asp Leu Ser Pro Arg Leu Pro Lys Lys Val Tyr Gly Gly
1               5                   10                  15

Asp Gly Gly Ser Tyr Phe Ala Trp Cys Pro Glu Glu Leu Pro Met Leu
            20                  25                  30

Arg Asp Gly Asn Ile Gly Ala Ser Lys Leu Ala Leu Glu Lys Tyr Gly
        35                  40                  45

Leu Ala Leu Pro Arg Tyr Ser Asp Ser Pro Lys Val Ala Tyr Val Leu
    50                  55                  60

Gln Gly Ala Gly Thr Ala Gly Ile Val Leu Pro Glu Lys Glu Glu Lys
65                  70                  75                  80

Val Ile Ala Ile Lys Lys Gly Asp Ser Ile Ala Leu Pro Phe Gly Val
                85                  90                  95

Val Thr Trp Trp Phe Asn Asn Glu Asp Thr Glu Leu Val Val Leu Phe
            100                 105                 110

Leu Gly Glu Thr His Lys Gly His Lys Ala Gly Gln Phe Thr Asp Phe
        115                 120                 125

Tyr Leu Thr Gly Ser Asn Gly Ile Phe Thr Gly Phe Ser Thr Glu Phe
    130                 135                 140

Val Gly Arg Ala Trp Asp Leu Asp Glu Thr Thr Val Lys Lys Leu Val
145                 150                 155                 160

Gly Ser Gln Thr Gly Asn Gly Ile Val Lys Val Asp Ala Ser Leu Lys
                165                 170                 175

Met Pro Glu Pro Lys Lys Gly Asp Arg Lys Gly Phe Val Leu Asn Cys
            180                 185                 190

Leu Glu Ala Pro Leu Asp Val Asp Ile Lys Asp Gly Gly Arg Val Val
        195                 200                 205

Val Leu Asn Thr Lys Asn Leu Pro Leu Val Gly Glu Val Gly Phe Gly
    210                 215                 220

Ala Asp Leu Val Arg Ile Asp Gly His Ser Met Cys Ser Pro Gly Phe
225                 230                 235                 240

Ser Cys Asp Ser Ala Leu Gln Val Thr Tyr Ile Val Gly Gly Ser Gly
                245                 250                 255

Arg Val Gln Ile Val Gly Ala Asp Gly Lys Arg Val Leu Glu Thr His
            260                 265                 270

Val Lys Ala Gly Val Leu Phe Ile Val Pro Arg Phe Phe Val Val Ser
        275                 280                 285

Lys Ile Ala Asp Ser Asp Gly Leu Ser Trp Phe Ser Ile Val Thr Thr
    290                 295                 300

Pro Asp Pro Ile Phe Thr His Leu Ala Gly Arg Thr Ser Val Trp Lys
305                 310                 315                 320
```

Ala Leu Ser Pro Glu Val Leu Gln Ala Ala Phe Lys Val Asp Pro Glu
            325                 330                 335

Val Glu Lys Ala Phe Arg Ser Lys Arg Thr Ser Asp Ala Ile Phe Phe
        340                 345                 350

Ser Pro Ser Asn
        355

<210> SEQ ID NO 61
<211> LENGTH: 1071
<212> TYPE: DNA
<213> ORGANISM: Glycine max

<400> SEQUENCE: 61

| | | | | | |
|---|---|---|---|---|---|
| atggacattg | atctttctcc | tcagttgccc | aagaaagttt | acggtgccaa | tggtggctcc | 60 |
| tactacgcat | ggtccccctc | cgaccttccc | atgctccacc | aaggcaacat | tggtgccgct | 120 |
| aagcttgctc | tcaacaaaaa | cgcctttgct | cttcctcgtt | actctgactc | ttccaaagtc | 180 |
| gcttatgttc | ttcaaggtag | tggagtggct | ggaatagtgt | tgcctgaatc | agaagagaag | 240 |
| gttgttgcaa | taagaaggg | tgatgccttg | gcactcccct | tggtgttgt | gacctggtgg | 300 |
| tataacaagg | aagaaactga | gttggttgtt | ctgttccttg | gggacacttc | caaggctcac | 360 |
| aaggctggtg | aattcactga | ctttttctg | actggttcca | atggaatctt | cactggcttt | 420 |
| tccaccgagt | ttgtgggcag | ggcttgggac | ttggaagaga | gtcatgtcaa | gacccttgtt | 480 |
| ggaaaacaac | cagccaaagg | gattgtgcag | ctggaaggaa | acatcagcct | cccgaccct | 540 |
| aaaccggagc | accgaaatgg | catggccttg | aactgtgaag | aggctccatt | ggatgttgac | 600 |
| atcaagggtg | gtggaagggt | tgtggtgttg | aacaccaaga | tcttcccctt | ggttggcgag | 660 |
| gttggactag | gggctgatct | tgtgaggctg | atggaagag | ccatgtgttc | gcctggattc | 720 |
| tcttgtgatt | ctgctttgca | ggttacttat | attgtcaggg | gtagtggccg | ggttcaggtt | 780 |
| gttggtgttg | acgccgtag | ggttttggag | acaaccgtga | aagctggtaa | tttgttcatt | 840 |
| gtgccaaggt | tttttgtggt | gtccaagatt | gctgatcctg | atggactgga | gtggttctct | 900 |
| atcatcacta | cccctaatcc | tatatttacc | cacttggcag | gaagttcttc | cgtgtggaag | 960 |
| gctttatcac | cttcggtttt | gcaagctgct | ttcaatgtag | atccagaagt | tgagcaactg | 1020 |
| ttccgttcaa | agaggactgc | cgatgccatt | tccttccctc | accaaacta | g | 1071 |

<210> SEQ ID NO 62
<211> LENGTH: 356
<212> TYPE: PRT
<213> ORGANISM: Glycine max

<400> SEQUENCE: 62

Met Asp Ile Asp Leu Ser Pro Gln Leu Pro Lys Lys Val Tyr Gly Ala
1               5                   10                  15

Asn Gly Gly Ser Tyr Tyr Ala Trp Ser Pro Ser Asp Leu Pro Met Leu
            20                  25                  30

His Gln Gly Asn Ile Gly Ala Ala Lys Leu Ala Leu Asn Lys Asn Ala
        35                  40                  45

Phe Ala Leu Pro Arg Tyr Ser Asp Ser Ser Lys Val Ala Tyr Val Leu
    50                  55                  60

Gln Gly Ser Gly Val Ala Gly Ile Val Leu Pro Glu Ser Glu Glu Lys
65                  70                  75                  80

Val Val Ala Ile Lys Lys Gly Asp Ala Leu Ala Leu Pro Phe Gly Val
                85                  90                  95

Val Thr Trp Trp Tyr Asn Lys Glu Thr Glu Leu Val Val Leu Phe
                100                 105                 110

Leu Gly Asp Thr Ser Lys Ala His Lys Ala Gly Phe Thr Asp Phe
        115                 120                 125

Phe Leu Thr Gly Ser Asn Gly Ile Phe Thr Gly Phe Ser Thr Glu Phe
    130                 135                 140

Val Gly Arg Ala Trp Asp Leu Glu Glu Ser His Val Lys Thr Leu Val
145                 150                 155                 160

Gly Lys Gln Pro Ala Lys Gly Ile Val Gln Leu Glu Gly Asn Ile Ser
                165                 170                 175

Leu Pro Asp Pro Lys Pro Glu His Arg Asn Gly Met Ala Leu Asn Cys
            180                 185                 190

Glu Glu Ala Pro Leu Asp Val Asp Ile Lys Gly Gly Arg Val Val
        195                 200                 205

Val Leu Asn Thr Lys Asn Leu Pro Leu Val Gly Glu Val Gly Leu Gly
    210                 215                 220

Ala Asp Leu Val Arg Leu Asp Gly Arg Ala Met Cys Ser Pro Gly Phe
225                 230                 235                 240

Ser Cys Asp Ser Ala Leu Gln Val Thr Tyr Ile Val Arg Gly Ser Gly
                245                 250                 255

Arg Val Gln Val Val Gly Val Asp Gly Arg Arg Val Leu Glu Thr Thr
            260                 265                 270

Val Lys Ala Gly Asn Leu Phe Ile Val Pro Arg Phe Phe Val Val Ser
        275                 280                 285

Lys Ile Ala Asp Pro Asp Gly Leu Glu Trp Phe Ser Ile Ile Thr Thr
    290                 295                 300

Pro Asn Pro Ile Phe Thr His Leu Ala Gly Ser Ser Ser Val Trp Lys
305                 310                 315                 320

Ala Leu Ser Pro Ser Val Leu Gln Ala Ala Phe Asn Val Asp Pro Glu
                325                 330                 335

Val Glu Gln Leu Phe Arg Ser Lys Arg Thr Ala Asp Ala Ile Phe Phe
            340                 345                 350

Pro Pro Pro Asn
        355

<210> SEQ ID NO 63
<211> LENGTH: 1407
<212> TYPE: DNA
<213> ORGANISM: Zea mays

<400> SEQUENCE: 63
atggggtggg gcacagtggt ttacgagggc gcggtcgtcg gctcgtcgct ggtggggctc      60
ggctgggcgg ggctgtggtt cctgaaccgg cggctgtaca aggagtacga ggagcggcgg     120
gtgctggtgc agatcctctt cggcctcgtc tttgccttct cctgcaacct cttcgagctc     180
gttctcttcg atcctgcc cgtcctctcc aagcacgcgc gcttcctcaa ctggcacctc     240
gacctcttct gcctcatcct cctcctcgtc ttcgtactcc cctactacca ctgctatctt     300
ctgctccgta actcagggat gaggagggac cgggcgtggc tcgtcgcggc gctctttctg     360
ctggtcttcc tatacgggtt ctggcgcatg gggattcact tccccatgcc ttcaccggag     420
aagggtttct ttacgatgcc gcagttggtc agtaggattg gggtgattgg agttagtgtc     480
atggctgttc tttctggttt tggtgccgtc aatctgccat acagttatct gtcgctattc     540
atcagggaaa ttgatgaaac agacatcaaa accttggaac gccagttgat gcaatccatc     600

```
gagacatgta ctgctaagaa gaagaaaatt attttgtccc agatggagat ggagaggatt      660
caaggatcag aggagaagtt aaaggccaga tcgtttctga agcgtatagt gggaacagtt      720
gttagatctg tgcaggaaga tcaaactgag caggatataa aaacttaga agcagaagtc      780 caggcactgg aagagctttc caaacagctg tttcttgaga tatatgaact tcgtcaagct      840
aagatagctg ctgcgtattc tcgaacttgg agaggtcatc ttcagaatct acttggatat      900
gctttatcag tctattgtgt ttataagatg ctcaagtcct tgcagagtgt agtctttaag      960
gagtcaggct ctgttgatcc tgtaacaatg tcaataacga ttttcctgag acattttgac     1020
attggcattg atgttgcact gttatctcag tacatatctt tgatgttcat cgggatgttg     1080
gttgtcatat ctgttcgagg tttcctggca aatgttatga agttcttctt cgctgtttct     1140
agagttggga gtgggtcgac aaccaatgtt gtccttttcc tatcagagat catgggaatg     1200
tacttcatat cttccattct tcttataaga aaaagcctgg caaatgaata tagggtgatc     1260
attactgatg tcttgggtgg tgatatccaa tttgacttct accatcgctg gtttgatgct     1320
atatttgtgg ctagtgcgtt cctctccttg cttcttatat ctgcccaata caccaccagg     1380
caaacagaca agcatccgat tgattga                                         1407
```

<210> SEQ ID NO 64
<211> LENGTH: 468
<212> TYPE: PRT
<213> ORGANISM: Zea mays

<400> SEQUENCE: 64

```
Met Gly Trp Gly Thr Val Val Tyr Glu Gly Ala Val Val Gly Ser Ser
1               5                   10                  15

Leu Val Gly Leu Gly Trp Ala Gly Leu Trp Phe Leu Asn Arg Arg Leu
            20                  25                  30

Tyr Lys Glu Tyr Glu Glu Arg Arg Val Leu Val Gln Ile Leu Phe Gly
        35                  40                  45

Leu Val Phe Ala Phe Ser Cys Asn Leu Phe Glu Leu Val Leu Phe Glu
    50                  55                  60

Ile Leu Pro Val Leu Ser Lys His Ala Arg Phe Leu Asn Trp His Leu
65                  70                  75                  80

Asp Leu Phe Cys Leu Ile Leu Leu Val Phe Val Leu Pro Tyr Tyr
                85                  90                  95

His Cys Tyr Leu Leu Leu Arg Asn Ser Gly Met Arg Arg Asp Arg Ala
            100                 105                 110

Trp Leu Val Ala Ala Leu Phe Leu Leu Val Phe Leu Tyr Gly Phe Trp
        115                 120                 125

Arg Met Gly Ile His Phe Pro Met Pro Ser Pro Glu Lys Gly Phe Phe
    130                 135                 140

Thr Met Pro Gln Leu Val Ser Arg Ile Gly Val Ile Gly Val Ser Val
145                 150                 155                 160

Met Ala Val Leu Ser Gly Phe Gly Ala Val Asn Leu Pro Tyr Ser Tyr
                165                 170                 175

Leu Ser Leu Phe Ile Arg Glu Ile Asp Glu Thr Asp Ile Lys Thr Leu
            180                 185                 190

Glu Arg Gln Leu Met Gln Ser Ile Glu Thr Cys Thr Ala Lys Lys Lys
        195                 200                 205

Lys Ile Ile Leu Ser Gln Met Glu Met Glu Arg Ile Gln Gly Ser Glu
    210                 215                 220
```

Glu Lys Leu Lys Ala Arg Ser Phe Leu Lys Arg Ile Val Gly Thr Val
225                 230                 235                 240

Val Arg Ser Val Gln Glu Asp Gln Thr Glu Gln Asp Ile Lys Asn Leu
            245                 250                 255

Glu Ala Glu Val Gln Ala Leu Glu Glu Leu Ser Lys Gln Leu Phe Leu
            260                 265                 270

Glu Ile Tyr Glu Leu Arg Gln Ala Lys Ile Ala Ala Tyr Ser Arg
        275                 280                 285

Thr Trp Arg Gly His Leu Gln Asn Leu Leu Gly Tyr Ala Leu Ser Val
290                 295                 300

Tyr Cys Val Tyr Lys Met Leu Lys Ser Leu Gln Ser Val Val Phe Lys
305                 310                 315                 320

Glu Ser Gly Ser Val Asp Pro Val Thr Met Ser Ile Thr Ile Phe Leu
            325                 330                 335

Arg His Phe Asp Ile Gly Ile Asp Val Ala Leu Leu Ser Gln Tyr Ile
            340                 345                 350

Ser Leu Met Phe Ile Gly Met Leu Val Val Ile Ser Val Arg Gly Phe
        355                 360                 365

Leu Ala Asn Val Met Lys Phe Phe Ala Val Ser Arg Val Gly Ser
370                 375                 380

Gly Ser Thr Thr Asn Val Val Leu Phe Leu Ser Glu Ile Met Gly Met
385                 390                 395                 400

Tyr Phe Ile Ser Ser Ile Leu Leu Ile Arg Lys Ser Leu Ala Asn Glu
            405                 410                 415

Tyr Arg Val Ile Ile Thr Asp Val Leu Gly Gly Asp Ile Gln Phe Asp
        420                 425                 430

Phe Tyr His Arg Trp Phe Asp Ala Ile Phe Val Ala Ser Ala Phe Leu
        435                 440                 445

Ser Leu Leu Leu Ile Ser Ala Gln Tyr Thr Thr Arg Gln Thr Asp Lys
450                 455                 460

His Pro Ile Asp
465

<210> SEQ ID NO 65
<211> LENGTH: 1182
<212> TYPE: DNA
<213> ORGANISM: Sorghum bicolor

<400> SEQUENCE: 65
atggggtggg gcacagtggt ttacgagggg gcggtcgtcg gctcgtcgct ggtggggctg      60
ggctgggcgg ggctgtggtt cctgaaccgg cggctgtaca aggagtacga ggagcggcgg     120
gtgctggtgc agatcctctt cggcctcgtc ttcgccttct cctgcaacct cttcgagctc     180
gttctcttcg agatcctccc cgtcctctcc aagcacgcgc gcttcctcaa ctggcacctc     240
gacctcttct gcctcattct cctcctcgtc ttcgtactcc cctactacca ctgctatctt     300
ctgctccgta actcaggtcc cggcccccaa tcaatctccc attgcttcat ttctctctcc     360
ctttctgggg gggtgaggag ggagcgggcg tggctcgtcg cggcgctctt tctgctggtc     420
ttcctatacg ggttctggcg catggggatt cacttcccca tgccttcacc ggagaagggt     480
ttgttgacgg aaattgatga agcagacatc aaaaccttgg aaaggcagct gatgcaatcc     540
atggagacat gtacttctaa gaagaagaaa attatcttgt cccagatgga gatggagagg     600
attcaaggat cagaggagat agctgctgcg tattctcgaa cgtggagagg catcttcag      660 aatctacttg gatatgcttt gtcggtgtat tgtgtttata gatgctcaa gtccttgcag      720

-continued

```
        agtgtagtct ttaaggagtc aggctctgtt gatcctgtaa caatgacaat aacaatttc    780 ctgagacatt ttgacattgg cattgatgtt gcactgttat ctcagtacat atctttgatg    840
ttcatcggga tgttggttgt catatctgtt cgaggtttct tggcaaatgt tatgaagttc    900
ttctttgccg tttctagagt tgggagtgga tcgacaacca atgttgtcct tttcctatca    960
gagatcatgg gcatgtactt catatcttcc attcttctta taagaaaaag cctggcaaat   1020
gaatataggg tgatcattac tgatgttttg ggtggtgata tccaatttga cttctaccac   1080
cgctggtttg atgctatatt tgtggctagt gcgttcctgt ccttgcttct gatttctgcc   1140
caatacacca ccaggcaaac agacaagcat ccgattgatt ga                     1182
```

<210> SEQ ID NO 66
<211> LENGTH: 393
<212> TYPE: PRT
<213> ORGANISM: Sorghum bicolor

<400> SEQUENCE: 66

```
Met Gly Trp Gly Thr Val Val Tyr Glu Gly Ala Val Val Gly Ser Ser
1               5                   10                  15

Leu Val Gly Leu Gly Trp Ala Gly Leu Trp Phe Leu Asn Arg Arg Leu
            20                  25                  30

Tyr Lys Glu Tyr Glu Glu Arg Arg Val Leu Val Gln Ile Leu Phe Gly
        35                  40                  45

Leu Val Phe Ala Phe Ser Cys Asn Leu Phe Glu Leu Val Leu Phe Glu
    50                  55                  60

Ile Leu Pro Val Leu Ser Lys His Ala Arg Phe Leu Asn Trp His Leu
65                  70                  75                  80

Asp Leu Phe Cys Leu Ile Leu Leu Val Phe Val Leu Pro Tyr Tyr
                85                  90                  95

His Cys Tyr Leu Leu Leu Arg Asn Ser Gly Pro Gly Pro Gln Ser Ile
            100                 105                 110

Ser His Cys Phe Ile Ser Leu Ser Leu Ser Gly Gly Val Arg Arg Glu
        115                 120                 125

Arg Ala Trp Leu Val Ala Ala Leu Phe Leu Leu Val Phe Leu Tyr Gly
    130                 135                 140

Phe Trp Arg Met Gly Ile His Phe Pro Met Pro Ser Pro Glu Lys Gly
145                 150                 155                 160

Leu Leu Thr Glu Ile Asp Glu Ala Asp Ile Lys Thr Leu Glu Arg Gln
                165                 170                 175

Leu Met Gln Ser Met Glu Thr Cys Thr Ser Lys Lys Lys Ile Ile
            180                 185                 190

Leu Ser Gln Met Glu Met Glu Arg Ile Gln Gly Ser Glu Glu Ile Ala
        195                 200                 205

Ala Ala Tyr Ser Arg Thr Trp Arg Gly His Leu Gln Asn Leu Leu Gly
    210                 215                 220

Tyr Ala Leu Ser Val Tyr Cys Val Tyr Lys Met Leu Lys Ser Leu Gln
225                 230                 235                 240

Ser Val Val Phe Lys Glu Ser Gly Ser Val Asp Pro Val Thr Met Thr
                245                 250                 255

Ile Thr Ile Phe Leu Arg His Phe Asp Ile Gly Ile Asp Val Ala Leu
            260                 265                 270

Leu Ser Gln Tyr Ile Ser Leu Met Phe Ile Gly Met Leu Val Val Ile
        275                 280                 285
```

```
Ser Val Arg Gly Phe Leu Ala Asn Val Met Lys Phe Phe Ala Val
290                 295                 300

Ser Arg Val Gly Ser Gly Ser Thr Thr Asn Val Val Leu Phe Leu Ser
305                 310                 315                 320

Glu Ile Met Gly Met Tyr Phe Ile Ser Ser Ile Leu Leu Ile Arg Lys
                325                 330                 335

Ser Leu Ala Asn Glu Tyr Arg Val Ile Ile Thr Asp Val Leu Gly Gly
                340                 345                 350

Asp Ile Gln Phe Asp Phe Tyr His Arg Trp Phe Asp Ala Ile Phe Val
            355                 360                 365

Ala Ser Ala Phe Leu Ser Leu Leu Leu Ile Ser Ala Gln Tyr Thr Thr
370                 375                 380

Arg Gln Thr Asp Lys His Pro Ile Asp
385                 390
```

<210> SEQ ID NO 67
<211> LENGTH: 1407
<212> TYPE: DNA
<213> ORGANISM: Arabidopsis thaliana

<400> SEQUENCE: 67

```
atgagttacg gatgggcgat atacgaaggc acggtggtga tagcttcact aagtctctta      60
ggatgggcag gttatggtt tcttaatcgg agattataca aagagtatga agagaaacga     120
gctttggttc aaatcatttt cagtgtcgtc ttcgctttct cttgtaatct attgcagctc     180
gttttgttcg agatcatacc tgttctctct agagaggcaa ggatgataaa ctggaaggtg     240
gatcttttt gtttgatact tcttctggtt ttcatgttgc cgtattacca ttgctatttg     300
atgcttcgta atagtggtgt aagaagggag cgtgcctctg ttggggcttt cttattcttg     360
tcagcattcc tttacgcatt ctggcgtatg ggagttcatt tccctatgcc ttcagcagat     420
aaagggtttt ttaccatgcc tcagctggtc agtagaattg ggtcattgg tgtgaccta      480
atggctgtct tatcaggatt tggagctgta aatttaccct acagctatat atccctcttc    540
attagggaga ttgaagaagc agatataata tctttggaaa ggcaactgat tcagtcaact    600
gagacgtgca tagcaaagaa gaagaaaatt atttgtgtc aattggaggt ggaacgaaat    660
caaggatcag aagagaatca gaaacgtagc tctttcttca gaagaattgt tgggactgtt    720
gtgcggtcgg ttcaagatga ccaaaaggaa caagacataa aaatattgga agcggaggtg    780
gaagccttag aggagctgtc aaaacagtta ttttggaag tatatgagct gcgtcaagca    840
aaggatgctg ctgcttattc tagaacttgg aagggtcatg tgcagaactt acttggttat    900
gcatgttcca tttattgtgt gtataaaatg ttgaagtctc ttcaaagtgt tgtcttcaaa    960
gaggccggta caaagatcc tgtcacgacg atgatcagca tattcttgcg gttgtttgat   1020
ataggagtag atgctgcact cctctcacag tatatatccc tgctgttcat tgggatgttg   1080
attgtgattt ctgtgagggg attcctgacg aacctgatga gttttttctt tgctgtctca   1140
agagtgggaa gtgggtcttc aagcaatgtt gtacttttcc tatctgaaat catgggaatg   1200
tactttttgt cttcaattct tcttatcaga aaaagcttga gaaatgagta caggggaatc   1260
ataacagatg tgttgggtgg agatattcag tttgatttct atcatcgatg gtttgatgca   1320
attttgtgg cgagtgcttt tctttctctc gttttgcttt ctgcacatta cacgtctcgt   1380
caatctgata agcacgccat cgagtaa                                      1407
```

<210> SEQ ID NO 68

```
<211> LENGTH: 468
<212> TYPE: PRT
<213> ORGANISM: Arabidopsis thaliana

<400> SEQUENCE: 68
```

| | | | | | | | | | | | | | | |
|---|---|---|---|---|---|---|---|---|---|---|---|---|---|---|
| Met | Ser | Tyr | Gly | Trp | Ala | Ile | Tyr | Glu | Gly | Thr | Val | Val | Ile | Ala | Ser |
| 1 | | | | 5 | | | | | 10 | | | | | 15 |
| Leu | Ser | Leu | Leu | Gly | Trp | Ala | Gly | Leu | Trp | Phe | Leu | Asn | Arg | Arg | Leu |
| | | | 20 | | | | | 25 | | | | | 30 | |
| Tyr | Lys | Glu | Tyr | Glu | Lys | Arg | Ala | Leu | Val | Gln | Ile | Ile | Phe | Ser |
| | | 35 | | | | | 40 | | | | | 45 | | |
| Val | Val | Phe | Ala | Phe | Ser | Cys | Asn | Leu | Leu | Gln | Leu | Val | Leu | Phe | Glu |
| | 50 | | | | | 55 | | | | | 60 | | | | |
| Ile | Ile | Pro | Val | Leu | Ser | Arg | Glu | Ala | Arg | Met | Ile | Asn | Trp | Lys | Val |
| 65 | | | | | 70 | | | | | 75 | | | | | 80 |
| Asp | Leu | Phe | Cys | Leu | Ile | Leu | Leu | Leu | Val | Phe | Met | Leu | Pro | Tyr | Tyr |
| | | | | 85 | | | | | 90 | | | | | 95 | |
| His | Cys | Tyr | Leu | Met | Leu | Arg | Asn | Ser | Gly | Val | Arg | Arg | Glu | Arg | Ala |
| | | | | 100 | | | | | 105 | | | | | 110 | |
| Ser | Val | Gly | Ala | Phe | Leu | Phe | Leu | Ser | Ala | Phe | Leu | Tyr | Ala | Phe | Trp |
| | | | 115 | | | | | 120 | | | | | 125 | | |
| Arg | Met | Gly | Val | His | Phe | Pro | Met | Pro | Ser | Ala | Asp | Lys | Gly | Phe | Phe |
| | 130 | | | | | 135 | | | | | 140 | | | | |
| Thr | Met | Pro | Gln | Leu | Val | Ser | Arg | Ile | Gly | Val | Ile | Gly | Val | Thr | Leu |
| 145 | | | | | 150 | | | | | 155 | | | | | 160 |
| Met | Ala | Val | Leu | Ser | Gly | Phe | Gly | Ala | Val | Asn | Leu | Pro | Tyr | Ser | Tyr |
| | | | | 165 | | | | | 170 | | | | | 175 | |
| Ile | Ser | Leu | Phe | Ile | Arg | Glu | Ile | Glu | Glu | Ala | Asp | Ile | Ile | Ser | Leu |
| | | | | 180 | | | | | 185 | | | | | 190 | |
| Glu | Arg | Gln | Leu | Ile | Gln | Ser | Thr | Glu | Thr | Cys | Ile | Ala | Lys | Lys | Lys |
| | | | 195 | | | | | 200 | | | | | 205 | | |
| Lys | Ile | Ile | Leu | Cys | Gln | Leu | Glu | Val | Glu | Arg | Asn | Gln | Gly | Ser | Glu |
| | 210 | | | | | 215 | | | | | 220 | | | | |
| Glu | Asn | Gln | Lys | Arg | Ser | Ser | Phe | Phe | Arg | Arg | Ile | Val | Gly | Thr | Val |
| 225 | | | | | 230 | | | | | 235 | | | | | 240 |
| Val | Arg | Ser | Val | Gln | Asp | Asp | Gln | Lys | Glu | Gln | Asp | Ile | Lys | Ile | Leu |
| | | | | 245 | | | | | 250 | | | | | 255 | |
| Glu | Ala | Glu | Val | Glu | Ala | Leu | Glu | Glu | Leu | Ser | Lys | Gln | Leu | Phe | Leu |
| | | | 260 | | | | | 265 | | | | | 270 | | |
| Glu | Val | Tyr | Glu | Leu | Arg | Gln | Ala | Lys | Asp | Ala | Ala | Tyr | Ser | Arg |
| | | 275 | | | | | 280 | | | | | 285 | | | |
| Thr | Trp | Lys | Gly | His | Val | Gln | Asn | Leu | Leu | Gly | Tyr | Ala | Cys | Ser | Ile |
| | 290 | | | | | 295 | | | | | 300 | | | | |
| Tyr | Cys | Val | Tyr | Lys | Met | Leu | Lys | Ser | Leu | Gln | Ser | Val | Val | Phe | Lys |
| 305 | | | | | 310 | | | | | 315 | | | | | 320 |
| Glu | Ala | Gly | Thr | Lys | Asp | Pro | Val | Thr | Thr | Met | Ile | Ser | Ile | Phe | Leu |
| | | | | 325 | | | | | 330 | | | | | 335 | |
| Arg | Leu | Phe | Asp | Ile | Gly | Val | Asp | Ala | Ala | Leu | Leu | Ser | Gln | Tyr | Ile |
| | | | 340 | | | | | 345 | | | | | 350 | | |
| Ser | Leu | Leu | Phe | Ile | Gly | Met | Leu | Ile | Val | Ile | Ser | Val | Arg | Gly | Phe |
| | | | 355 | | | | | 360 | | | | | 365 | | |
| Leu | Thr | Asn | Leu | Met | Lys | Phe | Phe | Ala | Val | Ser | Arg | Val | Gly | Ser |
| | 370 | | | | | 375 | | | | | 380 | | | | |
| Gly | Ser | Ser | Ser | Asn | Val | Val | Leu | Phe | Leu | Ser | Glu | Ile | Met | Gly | Met |

| | | | 385 | | | 390 | | | 395 | | | 400 | |
|---|---|---|---|---|---|---|---|---|---|---|---|---|---|

Tyr Phe Leu Ser Ser Ile Leu Leu Ile Arg Lys Ser Leu Arg Asn Glu
        405      410      415

Tyr Arg Gly Ile Ile Thr Asp Val Leu Gly Gly Asp Ile Gln Phe Asp
      420      425      430

Phe Tyr His Arg Trp Phe Asp Ala Ile Phe Val Ala Ser Ala Phe Leu
     435      440      445

Ser Leu Val Leu Leu Ser Ala His Tyr Thr Ser Arg Gln Ser Asp Lys
   450      455      460

His Ala Ile Glu
465

<210> SEQ ID NO 69
<211> LENGTH: 1407
<212> TYPE: DNA
<213> ORGANISM: Glycine max

<400> SEQUENCE: 69

```
atgggttggg gaaggggaat gttggaaggt gtggtggtgg tgggatgtct gtgtttactg      60
ggttgggcgg gtctgtggtt tttgaaccgt cgactctaca aagagtacga agagaaacgc     120
gtcctcgtcc aaatcatctt cagcgtcgtc tttgccttct cctgcaatct tctccagctc     180
gtcatcttcg aaatcattcc aatcctctcc aaagaggcaa gagtggtgaa ctggaaggtg     240
gacttgttct gtttgatctt gttgctggtc ttccttctcc cctattacca ttgttacttg     300
atgctcaaaa acaatggcgt cagggctgag agggctgcac ttggtgctat tctctttctg     360
ttcgcttttc tctatgcctt tggcgcatg gcattcact ttccaatgcc atctccagat       420
aaaggtttct tcaccatgcc tcaactggtg agtcgaattg gggttattgg tgttactgtc     480
atggctgtgc tatctggttt tggtgctgta aacctcccat acagttactt atcacttttc     540
atcagagaga ttgaggaaac agaaatcaag gccttggaaa gacagctaat gcaatcgatt     600
gagacctgtg tatcaaagaa aagaaaatt attctttgcc aaatggagat ggataacaag     660
caaggatctg aagagaagtt aaatgctaga tctttaatta acgaattgt tggtacggtt       720
gttcgatctg tgcaagagga tcaaaaagag caagatatta aagggttgga agcagaagtt     780
ctggccttag aagagctttc aaagcaattg ttcttggagg tctatgaact cgtcaagca      840
aaggaagctg ctgcttattc tcgaacttgg agaggacaca tgcagaatct acttggctat     900
gcttgttctg tatattgtgt gtataaaatg atcaagtcat gcaaagtgt tgttttcaaa      960
caggatggtt cagttgatcc cgtgacaagg ataataagta tattccttca gttctttgat   1020
ataggaataa atgcagccct attatcacag tacatttcct tgctattcat tggaatgttg   1080
gttgtgatat cagtgcgtgg attcttaaca aacctaatga agttcttttt tgctgtttca   1140
agagttggaa gtggatcttc aagcaatgta gttctgtttt tgtctgagat aatgggaatg   1200
tatttttgtat cttctattct tttaatcagg aaaagcttag caactgaata caggattatt   1260
ataacagagg tattgggtgg tgatatccag tttgactttt atcaccggtg gtttgatgca   1320
atttttgtgg ctagtgcatt cctttcactg cttttacttt ctgcacatta tacatctcgc   1380
caaattgaca acatccaat tgattaa                                         1407
```

<210> SEQ ID NO 70
<211> LENGTH: 468
<212> TYPE: PRT
<213> ORGANISM: Glycine max

```
<400> SEQUENCE: 70

Met Gly Trp Gly Arg Gly Met Leu Glu Gly Val Val Val Gly Cys
1               5                   10                  15

Leu Cys Leu Leu Gly Trp Ala Gly Leu Trp Phe Leu Asn Arg Leu
            20                  25                  30

Tyr Lys Glu Tyr Glu Lys Arg Val Leu Val Gln Ile Ile Phe Ser
        35                  40                  45

Val Val Phe Ala Phe Ser Cys Asn Leu Leu Gln Leu Val Ile Phe Glu
    50                  55                  60

Ile Ile Pro Ile Leu Ser Lys Glu Ala Arg Val Val Asn Trp Lys Val
65                  70                  75                  80

Asp Leu Phe Cys Leu Ile Leu Leu Val Phe Leu Leu Pro Tyr Tyr
                85                  90                  95

His Cys Tyr Leu Met Leu Lys Asn Asn Gly Val Arg Ala Glu Arg Ala
                100                 105                 110

Ala Leu Gly Ala Ile Leu Phe Leu Phe Ala Phe Leu Tyr Ala Phe Trp
            115                 120                 125

Arg Met Gly Ile His Phe Pro Met Pro Ser Pro Asp Lys Gly Phe Phe
130                 135                 140

Thr Met Pro Gln Leu Val Ser Arg Ile Gly Val Ile Gly Val Thr Val
145                 150                 155                 160

Met Ala Val Leu Ser Gly Phe Gly Ala Val Asn Leu Pro Tyr Ser Tyr
                165                 170                 175

Leu Ser Leu Phe Ile Arg Glu Ile Glu Glu Thr Glu Ile Lys Ala Leu
            180                 185                 190

Glu Arg Gln Leu Met Gln Ser Ile Glu Thr Cys Val Ser Lys Lys Lys
        195                 200                 205

Lys Ile Ile Leu Cys Gln Met Glu Met Asp Asn Lys Gln Gly Ser Glu
210                 215                 220

Glu Lys Leu Asn Ala Arg Ser Leu Ile Lys Arg Ile Val Gly Thr Val
225                 230                 235                 240

Val Arg Ser Val Gln Glu Asp Gln Lys Glu Gln Asp Ile Lys Gly Leu
                245                 250                 255

Glu Ala Glu Val Leu Ala Leu Glu Glu Leu Ser Lys Gln Leu Phe Leu
            260                 265                 270

Glu Val Tyr Glu Leu Arg Gln Ala Lys Glu Ala Ala Ala Tyr Ser Arg
        275                 280                 285

Thr Trp Arg Gly His Met Gln Asn Leu Leu Gly Tyr Ala Cys Ser Val
290                 295                 300

Tyr Cys Val Tyr Lys Met Ile Lys Ser Leu Gln Ser Val Val Phe Lys
305                 310                 315                 320

Gln Asp Gly Ser Val Asp Pro Val Thr Arg Ile Ile Ser Ile Phe Leu
                325                 330                 335

Gln Phe Phe Asp Ile Gly Ile Asn Ala Ala Leu Leu Ser Gln Tyr Ile
            340                 345                 350

Ser Leu Leu Phe Ile Gly Met Leu Val Val Ile Ser Val Arg Gly Phe
        355                 360                 365

Leu Thr Asn Leu Met Lys Phe Phe Ala Val Ser Arg Val Gly Ser
370                 375                 380

Gly Ser Ser Ser Asn Val Val Leu Phe Leu Ser Glu Ile Met Gly Met
385                 390                 395                 400

Tyr Phe Val Ser Ser Ile Leu Leu Ile Arg Lys Ser Leu Ala Thr Glu
                405                 410                 415
```

Tyr Arg Ile Ile Ile Thr Glu Val Leu Gly Gly Asp Ile Gln Phe Asp
            420                 425                 430

Phe Tyr His Arg Trp Phe Asp Ala Ile Phe Val Ala Ser Ala Phe Leu
            435                 440                 445

Ser Leu Leu Leu Leu Ser Ala His Tyr Thr Ser Arg Gln Ile Asp Lys
        450                 455                 460

His Pro Ile Asp
465

<210> SEQ ID NO 71
<211> LENGTH: 1833
<212> TYPE: DNA
<213> ORGANISM: Oryza sativa

<400> SEQUENCE: 71

| | |
|---|---|
| atgccggaag caccgaccgc caagacagca ccggcctacg gctacgcccc cggggcgcac | 60 |
| gccgaggcgc tcgagttcat cgagcacgtc acggcgaacg ccgggcaggt gcagcggcgc | 120 |
| gtgctcggcg agatcctggc gcagaacgcg ccggccgagt acctgcgccg gtacggaatc | 180 |
| cccgggtccc ccgacgttgt cgacgccttc cgccgcctcg tcccgctcgt cacatacgag | 240 |
| ggcctccagc cagacatcct ccgcatcgcc aacggcgaca cctcgccgat cttctccggg | 300 |
| aagcctatct ccgaattcct cacgagctcg ggcacgtcgg gaggggagag gaagctcatg | 360 |
| ccgaccatcg ccgacgagat gaacaggcgg tcgctgctgt acagcctgct gatgccggtg | 420 |
| atgagccagt cggtgtccgg gctcgacaaa ggcaaggcga tgtacctgct cttcgtgaag | 480 |
| gcggagtcgc gcacgccggg cgggctcgcg gcgcggccgg tgctcacaag ctactaccgg | 540 |
| agccggcagt tcctcgaccg tccgcgcgac ccctacacat cttacacgag ccccgacgag | 600 |
| gccatcctgt gcgtggactc ctaccagagc atgtacgcgc agctgctctg cggcctcgtc | 660 |
| caccgcgccg acgtgctgcg cgtgggcgcc gtgttcgcct ccggcttcct ccgcgccatc | 720 |
| catttcctcg agaagcactg ggcgcgcctc tgccacgaca tccgcaccgg cgagctcgac | 780 |
| ccggagatca ccgaccgcgt ggtgcgcgac gccgtcgggc gggtgctccg cgccgacccg | 840 |
| gcgctcgccg acgcgatcga ggacgagtgc gctagggcgt cgtgggaggg catcatccgg | 900 |
| cgcctgtggc cacgcaccaa gtacatcgac gtgatcgtga ccggcaccat gtcgcagtac | 960 |
| atcccgacgc tcgagttcta cggcggcggc ctgccgctga cgtgcaccat gtacgcctct | 1020 |
| tcggagtgct acttcggcct caacctgaat cccatgtgca agcccagcga cgtcgcctac | 1080 |
| acgctcatcc ccaccatgtg ctactacgag ttcctcccccg tcaattgcaa caatgccact | 1140 |
| gccgaggcga ccaccgcgca cctcgtcgac ctggtcgacg taaagctcgg cacgagtac | 1200 |
| gagctcgtgg tcaccacgta ttccggggttg tatcgttatc gcgtgggcga cgtgctgagg | 1260 |
| gtggcggggt tcaagaacaa ggccccgatg ttcagcttcg tgcggcggca gaacgtggcg | 1320 |
| ctgagcgtcg actcggacaa gacggacgag acggagctgc acgcggcggt gagcggcgcg | 1380 |
| gtgcagcacc tggcgccgtt cggcgcgtcg ctggtggagt acacgagcta cgcggacgcg | 1440 |
| gccaccatcc cgggccacta cgtgctgttc tgggagctgc cgccggcag cacggcggtg | 1500 |
| ccggcgtccg tgttcgagga gtgctgcctg tccgtggagg aggcactgaa cagcgtctac | 1560 |
| cggcagggcc gcgcgtgcga caggtccatc ggcccgctcg agatacgcgt cgtggcggag | 1620 |
| ggcaccttcg acaagctcat ggactacgcg atcagccggg gcgcgtccat caaccagtac | 1680 |
| aaggcgccgc ggtgcgtgcg ccctggcccg gtcgtcgagc tgctcgacgc gagggtgcag | 1740 |

-continued

```
ggcaagtact tcagtcccaa gtgccccaag tggagccccg ggaacaagca atggaacaaa    1800
agcaaggatc tggtcggcaa gggagacgcc taa                                 1833
```

<210> SEQ ID NO 72
<211> LENGTH: 610
<212> TYPE: PRT
<213> ORGANISM: Oryza sativa

<400> SEQUENCE: 72

| | | | | | | | | | | | | | | |
|---|---|---|---|---|---|---|---|---|---|---|---|---|---|---|
| Met | Pro | Glu | Ala | Pro | Thr | Ala | Lys | Thr | Ala | Pro | Ala | Tyr | Gly | Tyr | Ala |
| 1 | | | | 5 | | | | | 10 | | | | | 15 | |
| Pro | Gly | Ala | His | Ala | Glu | Ala | Leu | Glu | Phe | Ile | Glu | His | Val | Thr | Ala |
| | | | | 20 | | | | | 25 | | | | | 30 | |
| Asn | Ala | Gly | Gln | Val | Gln | Arg | Arg | Val | Leu | Gly | Glu | Ile | Leu | Ala | Gln |
| | | | 35 | | | | | 40 | | | | | 45 | | |
| Asn | Ala | Pro | Ala | Glu | Tyr | Leu | Arg | Arg | Tyr | Gly | Ile | Pro | Gly | Ser | Pro |
| | 50 | | | | | 55 | | | | | 60 | | | | |
| Asp | Val | Val | Asp | Ala | Phe | Arg | Arg | Leu | Val | Pro | Leu | Val | Thr | Tyr | Glu |
| 65 | | | | | 70 | | | | | 75 | | | | | 80 |
| Gly | Leu | Gln | Pro | Asp | Ile | Leu | Arg | Ile | Ala | Asn | Gly | Asp | Thr | Ser | Pro |
| | | | | 85 | | | | | 90 | | | | | 95 | |
| Ile | Phe | Ser | Gly | Lys | Pro | Ile | Ser | Glu | Phe | Leu | Thr | Ser | Ser | Gly | Thr |
| | | | | 100 | | | | | 105 | | | | | 110 | |
| Ser | Gly | Gly | Glu | Arg | Lys | Leu | Met | Pro | Thr | Ile | Ala | Asp | Glu | Met | Asn |
| | | | 115 | | | | | 120 | | | | | 125 | | |
| Arg | Arg | Ser | Leu | Leu | Tyr | Ser | Leu | Leu | Met | Pro | Val | Met | Ser | Gln | Ser |
| 130 | | | | | 135 | | | | | 140 | | | | | |
| Val | Ser | Gly | Leu | Asp | Lys | Gly | Lys | Ala | Met | Tyr | Leu | Leu | Phe | Val | Lys |
| 145 | | | | | 150 | | | | | 155 | | | | | 160 |
| Ala | Glu | Ser | Arg | Thr | Pro | Gly | Gly | Leu | Ala | Ala | Arg | Pro | Val | Leu | Thr |
| | | | | 165 | | | | | 170 | | | | | 175 | |
| Ser | Tyr | Tyr | Arg | Ser | Arg | Gln | Phe | Leu | Asp | Arg | Pro | Arg | Asp | Pro | Tyr |
| | | | 180 | | | | | 185 | | | | | 190 | | |
| Thr | Ser | Tyr | Thr | Ser | Pro | Asp | Glu | Ala | Ile | Leu | Cys | Val | Asp | Ser | Tyr |
| | | | | 195 | | | | | 200 | | | | | 205 | |
| Gln | Ser | Met | Tyr | Ala | Gln | Leu | Leu | Cys | Gly | Leu | Val | His | Arg | Ala | Asp |
| | 210 | | | | | 215 | | | | | 220 | | | | |
| Val | Leu | Arg | Val | Gly | Ala | Val | Phe | Ala | Ser | Gly | Phe | Leu | Arg | Ala | Ile |
| 225 | | | | | 230 | | | | | 235 | | | | | 240 |
| His | Phe | Leu | Glu | Lys | His | Trp | Ala | Arg | Leu | Cys | His | Asp | Ile | Arg | Thr |
| | | | | 245 | | | | | 250 | | | | | 255 | |
| Gly | Glu | Leu | Asp | Pro | Glu | Ile | Thr | Asp | Arg | Val | Val | Arg | Asp | Ala | Val |
| | | | | 260 | | | | | 265 | | | | | 270 | |
| Gly | Arg | Val | Leu | Arg | Ala | Asp | Pro | Ala | Leu | Ala | Asp | Ala | Ile | Glu | Asp |
| | | | 275 | | | | | 280 | | | | | 285 | | |
| Glu | Cys | Ala | Arg | Ala | Ser | Trp | Glu | Gly | Ile | Ile | Arg | Arg | Leu | Trp | Pro |
| | | 290 | | | | | 295 | | | | | 300 | | | |
| Arg | Thr | Lys | Tyr | Ile | Asp | Val | Ile | Val | Thr | Gly | Thr | Met | Ser | Gln | Tyr |
| 305 | | | | | 310 | | | | | 315 | | | | | 320 |
| Ile | Pro | Thr | Leu | Glu | Phe | Tyr | Gly | Gly | Gly | Leu | Pro | Leu | Thr | Cys | Thr |
| | | | | 325 | | | | | 330 | | | | | 335 | |
| Met | Tyr | Ala | Ser | Ser | Glu | Cys | Tyr | Phe | Gly | Leu | Asn | Leu | Asn | Pro | Met |
| | | | 340 | | | | | 345 | | | | | 350 | | |
| Cys | Lys | Pro | Ser | Asp | Val | Ala | Tyr | Thr | Leu | Ile | Pro | Thr | Met | Cys | Tyr |

|     |     |     |     |     | 355 |     |     |     |     | 360 |     |     |     |     | 365 |     |     |

Tyr Glu Phe Leu Pro Val Asn Cys Asn Asn Ala Thr Ala Glu Ala Ser
        370                     375                 380

His Arg Asp Leu Val Asp Leu Val Asp Val Lys Leu Gly His Glu Tyr
385                     390                     395                 400

Glu Leu Val Val Thr Thr Tyr Ser Gly Leu Tyr Arg Tyr Arg Val Gly
                405                     410                 415

Asp Val Leu Arg Val Ala Gly Phe Lys Asn Lys Ala Pro Met Phe Ser
            420                     425                 430

Phe Val Arg Arg Gln Asn Val Ala Leu Ser Val Asp Ser Asp Lys Thr
            435                     440                 445

Asp Glu Thr Glu Leu His Ala Ala Val Ser Gly Ala Val Gln His Leu
        450                     455                 460

Ala Pro Phe Gly Ala Ser Leu Val Glu Tyr Thr Ser Tyr Ala Asp Ala
465                     470                     475                 480

Ala Thr Ile Pro Gly His Tyr Val Leu Phe Trp Glu Leu Arg Ala Gly
                485                     490                 495

Ser Thr Ala Val Pro Ala Ser Val Phe Glu Glu Cys Cys Leu Ser Val
            500                     505                 510

Glu Glu Ala Leu Asn Ser Val Tyr Arg Gln Gly Arg Ala Cys Asp Arg
        515                     520                 525

Ser Ile Gly Pro Leu Glu Ile Arg Val Val Ala Glu Gly Thr Phe Asp
530                     535                     540

Lys Leu Met Asp Tyr Ala Ile Ser Arg Gly Ala Ser Ile Asn Gln Tyr
545                     550                     555                 560

Lys Ala Pro Arg Cys Val Arg Pro Gly Pro Val Glu Leu Leu Asp
                565                     570                 575

Ala Arg Val Gln Gly Lys Tyr Phe Ser Pro Lys Cys Pro Lys Trp Ser
            580                     585                 590

Pro Gly Asn Lys Gln Trp Asn Lys Ser Lys Asp Leu Val Gly Lys Gly
        595                     600                 605

Asp Ala
    610

<210> SEQ ID NO 73
<211> LENGTH: 1809
<212> TYPE: DNA
<213> ORGANISM: Oryza sativa

<400> SEQUENCE: 73
atgaagtacg tgctggtgac aggaggggtg gtgagcggcc tcggcaaggg cgtgaccgcg      60
agcagcatcg cgtcgtgct caaggcctgc gggctccgcg tcaccaccat caagattgac     120
ccatacctca acactgatgc tggaaccatg tctccgttcg agcatggtga ggtcttcgtt     180
ttggacgatg gtgagaggt ggacttggac cttggaaatt acgaacgttt tctggacatc     240
aaattgaccc gtgataacaa cataaccacg ggaaaaatat atcagtcagt cattaacaaa     300
gaaaggagag gagactactt ggggaaaacc attcaggttg tgccacatat tacagatgaa     360
attcaagatt ggattgaacg tgtagcgatg aatccggtcg atggtaaaga aggacctcct     420
gatgtttgtg tcatagaact tggtggcacc atagggggata ttgaatcaat gccctttatt     480
gaagcattag gtcaatttc ctaccgtgtt ggacctggaa acttctgtct ggtccatgtc     540
agtcttgttc cagttttaaa tgtagttggt gaacagaaaa ctaaacctac ccagcatagt     600
gttcgtgggc taagaggcct tggattggca cctgacattt tagcatgtcg cagtaccgag     660

-continued

```
ccactggaag aaaacgtgaa agcaaagctc tcacaatttt gtcacgttcc agtctcaagt    720
attattaatc tccatgacgt tacaaacatt tggcacatcc ccttgttgct aagggaccaa    780
agggcccatg aagctattct gaaagttcta gaccttcaat tgtcggtaa agtaccacga     840 gaacccaagt tggttgaatg gaccgaaaga gccagcaagt tgacaagtt gaaggctacg     900 gttaagattg cgatggttgg aaaatatact gggctgtccg attcctacct gtctgttcta    960
aaggcacttt tgcatgcatc ggttgctatg ggaagaaagc ttgtagtgga gtgggttcct   1020
tcctgtgatc ttgaagattc tgcagccaaa gagacccctg aagcccataa aaaagcatgg   1080
aagctactca agggtgcaga gggtatactt gtccctggag gctttggaga tagaggtgtt   1140
cagggaaaaa ttcttgctgc aaaatatgca cgagaaaata atgttcctta ctctcggcatt  1200 tgcttgggta tgcaaattgc agtgattgat tttgcctgtt ctatcatgaa attaccgggt   1260
gcaaatagca cagagtttga cccagataca atgtcaccct gcgtcatttt catgccagag   1320
ggttccaaaa cccatatggg ggcaactatg cggcttggat caaggagaac atatttccat   1380
gccactgcat gcaaatctgc aaagctgtat ggtaatgcta gattcgtaga cgaaagacat   1440
cgacacagat atgaggtaaa tcctgaaatg gtaccagagt ttgagaaggc cggactttca   1500
tttgttggca aggatgagag tggaagacgc atggagatta ttgaactacc cagtcataaa   1560
tttttcattg gagtacagtt ccatcctgaa ttcaagtcaa gaccagggaa gccatctcca   1620
cttttcttag gattaatagc agcagcatct ggacaactag aaactttgct ccaaccaagt   1680
tccaacattg tcaatccaaa tcctatgccc agatttccca ttcccaaaaa gacgatttac   1740
catgccaaga agccactgga cagcttggta aacggatact ttgcaaatgg caacgtcatc   1800
cacacttga                                                          1809
```

<210> SEQ ID NO 74
<211> LENGTH: 602
<212> TYPE: PRT
<213> ORGANISM: Oryza sativa

<400> SEQUENCE: 74

```
Met Lys Tyr Val Leu Val Thr Gly Gly Val Ser Gly Leu Gly Lys
1               5                   10                  15

Gly Val Thr Ala Ser Ser Ile Gly Val Val Leu Lys Ala Cys Gly Leu
                20                  25                  30

Arg Val Thr Thr Ile Lys Ile Asp Pro Tyr Leu Asn Thr Asp Ala Gly
            35                  40                  45

Thr Met Ser Pro Phe Glu His Gly Glu Val Phe Val Leu Asp Asp Gly
        50                  55                  60

Gly Glu Val Asp Leu Asp Leu Gly Asn Tyr Glu Arg Phe Leu Asp Ile
65                  70                  75                  80

Lys Leu Thr Arg Asp Asn Asn Ile Thr Thr Gly Lys Ile Tyr Gln Ser
                85                  90                  95

Val Ile Asn Lys Glu Arg Arg Gly Asp Tyr Leu Gly Lys Thr Ile Gln
                100                 105                 110

Val Val Pro His Ile Thr Asp Glu Ile Gln Asp Trp Ile Glu Arg Val
            115                 120                 125

Ala Met Asn Pro Val Asp Gly Lys Glu Gly Pro Asp Val Cys Val
        130                 135                 140

Ile Glu Leu Gly Gly Thr Ile Gly Asp Ile Glu Ser Met Pro Phe Ile
145                 150                 155                 160
```

```
Glu Ala Leu Gly Gln Phe Ser Tyr Arg Val Gly Pro Gly Asn Phe Cys
                165                 170                 175

Leu Val His Val Ser Leu Val Pro Val Leu Asn Val Val Gly Glu Gln
            180                 185                 190

Lys Thr Lys Pro Thr Gln His Ser Val Arg Gly Leu Arg Gly Leu Gly
        195                 200                 205

Leu Ala Pro Asp Ile Leu Ala Cys Arg Ser Thr Glu Pro Leu Glu Glu
    210                 215                 220

Asn Val Lys Ala Lys Leu Ser Gln Phe Cys His Val Pro Val Ser Ser
225                 230                 235                 240

Ile Ile Asn Leu His Asp Val Thr Asn Ile Trp His Ile Pro Leu Leu
                245                 250                 255

Leu Arg Asp Gln Arg Ala His Glu Ala Ile Leu Lys Val Leu Asp Leu
            260                 265                 270

Gln Phe Val Gly Lys Val Pro Arg Glu Pro Lys Leu Val Glu Trp Thr
        275                 280                 285

Glu Arg Ala Ser Lys Phe Asp Lys Leu Lys Ala Thr Val Lys Ile Ala
    290                 295                 300

Met Val Gly Lys Tyr Thr Gly Leu Ser Asp Ser Tyr Leu Ser Val Leu
305                 310                 315                 320

Lys Ala Leu Leu His Ala Ser Val Ala Met Gly Arg Lys Leu Val Val
                325                 330                 335

Glu Trp Val Pro Ser Cys Asp Leu Glu Asp Ser Ala Ala Lys Glu Thr
            340                 345                 350

Pro Glu Ala His Lys Lys Ala Trp Lys Leu Leu Lys Gly Ala Glu Gly
        355                 360                 365

Ile Leu Val Pro Gly Gly Phe Gly Asp Arg Gly Val Gln Gly Lys Ile
    370                 375                 380

Leu Ala Ala Lys Tyr Ala Arg Glu Asn Asn Val Pro Tyr Leu Gly Ile
385                 390                 395                 400

Cys Leu Gly Met Gln Ile Ala Val Ile Asp Phe Ala Cys Ser Ile Met
                405                 410                 415

Lys Leu Pro Gly Ala Asn Ser Thr Glu Phe Asp Pro Asp Thr Met Ser
            420                 425                 430

Pro Cys Val Ile Phe Met Pro Glu Gly Ser Lys Thr His Met Gly Ala
        435                 440                 445

Thr Met Arg Leu Gly Ser Arg Arg Thr Tyr Phe His Ala Thr Ala Cys
    450                 455                 460

Lys Ser Ala Lys Leu Tyr Gly Asn Ala Arg Phe Val Asp Glu Arg His
465                 470                 475                 480

Arg His Arg Tyr Glu Val Asn Pro Glu Met Val Pro Glu Phe Glu Lys
                485                 490                 495

Ala Gly Leu Ser Phe Val Gly Lys Asp Glu Ser Gly Arg Arg Met Glu
            500                 505                 510

Ile Ile Glu Leu Pro Ser His Lys Phe Ile Gly Val Gln Phe His Pro
        515                 520                 525

Pro Glu Phe Lys Ser Arg Pro Gly Lys Pro Ser Pro Leu Phe Leu Gly
    530                 535                 540

Leu Ile Ala Ala Ala Ser Gly Gln Leu Glu Thr Leu Leu Gln Pro Ser
545                 550                 555                 560

Ser Asn Ile Val Asn Pro Asn Pro Met Pro Arg Phe Pro Ile Pro Lys
                565                 570                 575

Lys Thr Ile Tyr His Ala Lys Lys Pro Leu Asp Ser Leu Val Asn Gly
```

```
                580             585             590
Tyr Phe Ala Asn Gly Asn Val Ile His Thr
            595             600

<210> SEQ ID NO 75
<211> LENGTH: 1818
<212> TYPE: DNA
<213> ORGANISM: Zea mays

<400> SEQUENCE: 75
atgaagtacg tgctggtgac cggcggcgtg gtgagcgggc tcgggaaggg cgtgacggcc      60
agcagcgtcg gggtcgtcct caagtcctgc ggcctccgcg tcacctccat caagatcgat     120
ccatacctca acatcgatgc cggaaccatg tctccgctcg agcatggcga agtgtttgtt     180
ttggacgacg gcggtgaggt ggacttggac cttggaaact acgaacgatt tctggacatc     240
aagctgactc gtgacaacaa cataaccacg gggaagatct accagtctgt tattgacaag     300
gaacgtagag gggattacct aggaaaaact gttcaggttg tgccgcacat cacagatgaa     360
atacaagagt ggattgaacg tgtggcaatg aatccagttg atggcacaga gagccagct      420 gatgtttgtg tcatagaact tggtggcact ataggggaca ttgaatcaat gcctttcatt     480
gaagcattag gtcaatttc ataccgtgta gggcctggaa acttctgctt ggtgcatgtc      540
agtcttgtac cagttttaaa tgtggttggt gagcagaaaa caaagcccac caacatagt     600 gttcgcggac ttagaggact tggactcatg cctgatattt tggcatgccg tagtacacag     660
ccacttgaag aacatgtgaa agtgaagctc gcacaatttt gtcatgttcc gatatcaaat     720
atcattaatc tccgtgatgt aacgaacatt tggcacatcc ctttgttgct cagagaccag     780
aaggcccatg aagctatttt gaaagtgtta gacattcagt gtgtgggtaa agttgctcga     840
gaaccccagt tgtctgaatg gactgaaaga gccagcagat gtgacagatt gaaatctccg     900
gttaggattg ctatggttgg aaagtatact ggcctgtcag attcctacct atctgttatc     960
aaggctcttt tgcatgcgtc ggttgctttg gacaggaaac ttgtggtaga ctgggttcct    1020
tcctgtgatc ttgaagattc tgcagcagaa gagaatcttg atgcctacga aaaagcatgg    1080
gaattgttaa agggtgcaga tggtgtgttg gtgccagggg gttttggaga cagaggagtt    1140
caagggaaaa ttctggctgc aaaatatgcg cgagaaaaca acattccata tcttggcatt    1200
tgcttgggca tgcaaattgc agtgattgag tttgcacgtt ctatcatgaa gttgcacggt    1260
gcaaacagca cagagttcga tccaaccaca aaaccccat gtgttatttt catgccagag     1320
gggtcaaaaa cccatatggg ggcaacaatg cgccttggat caaggaggac ctttttccag    1380
gtcactaact gcaaatctgc taaactgtat gggaatgcta gctacgttga tgaacggcac    1440
cgccacagat acgaggtgaa tcctgatatg gtcccagaat tgagaaggc agggctttct     1500 ttcgttggca gggatgaaag tggtaaacgc atggagatta cgaactgcc aactcatagg     1560 tttttcgtcg gtgcacaatt tcatcctgaa ttcaagtcaa ggcccggcaa gccatctccg    1620
cttttcttag gattggtagc agcgtcatca ggtcagcttg atcacctgct ccaacctggt    1680
cttatcagtt cgactggcag acacacctgc agcaaaggag gagcgcaaaa attaaaggct    1740
gggcacgtca tgaagccact gaatggcctg gtgaacgcac actattcagc aaccggcaat    1800
ggcgccattc ccatctag                                                 1818

<210> SEQ ID NO 76
<211> LENGTH: 605
<212> TYPE: PRT
```

<213> ORGANISM: Zea mays

<400> SEQUENCE: 76

Met Lys Tyr Val Leu Val Thr Gly Gly Val Ser Gly Leu Gly Lys
1               5                   10                  15

Gly Val Thr Ala Ser Ser Val Gly Val Val Leu Lys Ser Cys Gly Leu
            20                  25                  30

Arg Val Thr Ser Ile Lys Ile Asp Pro Tyr Leu Asn Ile Asp Ala Gly
            35                  40                  45

Thr Met Ser Pro Leu Glu His Gly Glu Val Phe Val Leu Asp Asp Gly
        50                  55                  60

Gly Glu Val Asp Leu Asp Leu Gly Asn Tyr Glu Arg Phe Leu Asp Ile
65                  70                  75                  80

Lys Leu Thr Arg Asp Asn Asn Ile Thr Thr Gly Lys Ile Tyr Gln Ser
                85                  90                  95

Val Ile Asp Lys Glu Arg Arg Gly Asp Tyr Leu Gly Lys Thr Val Gln
            100                 105                 110

Val Val Pro His Ile Thr Asp Glu Ile Gln Glu Trp Ile Glu Arg Val
            115                 120                 125

Ala Met Asn Pro Val Asp Gly Thr Glu Pro Ala Asp Val Cys Val
        130                 135                 140

Ile Glu Leu Gly Gly Thr Ile Gly Asp Ile Glu Ser Met Pro Phe Ile
145                 150                 155                 160

Glu Ala Leu Gly Gln Phe Ser Tyr Arg Val Gly Pro Gly Asn Phe Cys
                165                 170                 175

Leu Val His Val Ser Leu Val Pro Val Leu Asn Val Val Gly Glu Gln
            180                 185                 190

Lys Thr Lys Pro Thr Gln His Ser Val Arg Gly Leu Arg Gly Leu Gly
            195                 200                 205

Leu Met Pro Asp Ile Leu Ala Cys Arg Ser Thr Gln Pro Leu Glu Glu
        210                 215                 220

His Val Lys Val Lys Leu Ala Gln Phe Cys His Val Pro Ile Ser Asn
225                 230                 235                 240

Ile Ile Asn Leu Arg Asp Val Thr Asn Ile Trp His Ile Pro Leu Leu
                245                 250                 255

Leu Arg Asp Gln Lys Ala His Glu Ala Ile Leu Lys Val Leu Asp Ile
            260                 265                 270

Gln Cys Val Gly Lys Val Ala Arg Glu Pro Gln Leu Ser Glu Trp Thr
        275                 280                 285

Glu Arg Ala Ser Arg Cys Asp Arg Leu Lys Ser Pro Val Arg Ile Ala
        290                 295                 300

Met Val Gly Lys Tyr Thr Gly Leu Ser Asp Ser Tyr Leu Ser Val Ile
305                 310                 315                 320

Lys Ala Leu Leu His Ala Ser Val Ala Leu Asp Arg Lys Leu Val Val
                325                 330                 335

Asp Trp Val Pro Ser Cys Asp Leu Glu Asp Ser Ala Ala Glu Glu Asn
            340                 345                 350

Leu Asp Ala Tyr Glu Lys Ala Trp Glu Leu Leu Lys Gly Ala Asp Gly
        355                 360                 365

Val Leu Val Pro Gly Gly Phe Gly Asp Arg Gly Val Gln Gly Lys Ile
        370                 375                 380

Leu Ala Ala Lys Tyr Ala Arg Glu Asn Asn Ile Pro Tyr Leu Gly Ile
385                 390                 395                 400

```
Cys Leu Gly Met Gln Ile Ala Val Ile Glu Phe Ala Arg Ser Ile Met
                405                 410                 415
Lys Leu His Gly Ala Asn Ser Thr Glu Phe Asp Pro Thr Thr Lys Thr
            420                 425                 430
Pro Cys Val Ile Phe Met Pro Glu Gly Ser Lys Thr His Met Gly Ala
        435                 440                 445
Thr Met Arg Leu Gly Ser Arg Arg Thr Phe Phe Gln Val Thr Asn Cys
    450                 455                 460
Lys Ser Ala Lys Leu Tyr Gly Asn Ala Ser Tyr Val Asp Glu Arg His
465                 470                 475                 480
Arg His Arg Tyr Glu Val Asn Pro Asp Met Val Pro Glu Phe Glu Lys
                485                 490                 495
Ala Gly Leu Ser Phe Val Gly Arg Asp Glu Ser Gly Lys Arg Met Glu
            500                 505                 510
Ile Ile Glu Leu Pro Thr His Arg Phe Phe Val Gly Ala Gln Phe His
        515                 520                 525
Pro Glu Phe Lys Ser Arg Pro Gly Lys Pro Ser Pro Leu Phe Leu Gly
    530                 535                 540
Leu Val Ala Ala Ser Ser Gly Gln Leu Asp His Leu Leu Gln Pro Gly
545                 550                 555                 560
Leu Ile Ser Ser Thr Gly Arg His Thr Cys Ser Lys Gly Gly Ala Gln
                565                 570                 575
Lys Leu Lys Ala Gly His Val Met Lys Pro Leu Asn Gly Leu Val Asn
            580                 585                 590
Ala His Tyr Ser Ala Thr Gly Asn Gly Ala Ile Pro Ile
        595                 600                 605

<210> SEQ ID NO 77
<211> LENGTH: 1818
<212> TYPE: DNA
<213> ORGANISM: Sorghum bicolor

<400> SEQUENCE: 77
atgaagtacg tgctggtgac cggcggagtg gtgagcgggc tcgggaaggg cgtgacggcc      60
agcagcatcg gcgtccttct caagtcctgc ggcttccgcg tcacctccat caagatcgat     120
ccatacctca acaccgatgc cggaaccatg tctcccttcg agcacggcga ggtgtttgtt     180
ttggacgacg tggtgaggt ggacttggac cttggaaact acgaacgatt tctgacatc      240 aagttgactc gtgacaacaa cataaccacg gggaagatct atcagtctgt cattgacaag     300
gaacgtagag gagattacct aggaaaaact gttcaggttg tgccgcacat cacagatgaa     360
atacaagagt ggattgaacg tgtggcaatg aatccagttg atggcacaga gaggcagct     420 gatgtttgtg tcatagaact tggtggcact ataggggaca ttgaatcaat gcctttcatt     480
gaagcattag gtcaattttc ataccgtgta gggcctggaa acttctgctt ggtgcatgtc     540
agtcttgtac cagttcttaa tgtagttggt gagcagaaaa caaagcccac caacatagt     600 gttcgcggac ttagaggact tggactcatg cctgatattt tggcatgtcg tagtacacat     660
ccacttgaag aacatgtgaa agtgaagctc gcgcaatttt gtcatgttcc gataccaaat     720
atcattaatc tccatgatgt cacaaacatt tggcacatcc ctttgttgct cagagatcag     780
aaggcccatg aagctatttt gaaagtgtta gaccttcagt gtgtgggtaa agttgctcga     840
gaaccccaat tgtctgaatg gactgaaaga gccagcagat gtgacagatt gaaaactccg     900
gttaggattg ctatggttgg aaagtatact ggcttatcag attcctacct atctgttatc     960
```

```
aaggctcttt tgcatgcgtc agttgctttg dacaggaaac ttgtggtgga ctgggttcct    1020
tcctgtgatc ttgaagattc tacagcagaa gagactcctg atgcctatga aaaagcatgg    1080
gagtcgctaa agggtgcaga tggtgtgttg gtgccaggag gttttggaga cagaggagtc    1140
caagggaaaa ttcttgctgc aaaatacgcg cgagaaaaca acattccata tcttggcatt    1200
tgcttgggca tgcaaattgc agtgattgag tttgcacgtt ctatcatgaa gttgcatggt    1260
gctaacagca cagagtttga tccaaccaca aaaacaccat gtgttatttt catgccagag    1320
ggatccaaaa cccatatggg ggcaacaatg cgccttggat caaggaggac cttttccag    1380 gtcactaact gcaaatctgc taaactgtat ggcaatgtta gctacattga tgaaaggcac    1440
cgccacagat acgaggtgaa tcctgatatg gtcccagaat ttgagaaggc agggctttct    1500
ttcgttggca gggatgaaag cggtaaacgc atggagatta tcgaactacc aactcatagg    1560
tttttcgttg gtgtacaatt tcaccctgaa ttcaagtcaa ggcctggcaa cccatctccg    1620 ctttttcttag gattggtagc agcatcatca ggtcagcttg atcaacgtgg cgttatcagt    1680
aagacaagca gatgcatcag caataccgga ggagcatcaa agctaaaagc ttgccagaat    1740
gggcacctca tgaagccact gaagggcctg gtgaacgggc actattcaac aaccagcaat    1800
ggcgccattc ccatctag                                                  1818

<210> SEQ ID NO 78
<211> LENGTH: 605
<212> TYPE: PRT
<213> ORGANISM: Sorghum bicolor

<400> SEQUENCE: 78

Met Lys Tyr Val Leu Val Thr Gly Gly Val Ser Gly Leu Gly Lys
1               5                   10                  15

Gly Val Thr Ala Ser Ser Ile Gly Val Leu Leu Lys Ser Cys Gly Phe
                20                  25                  30

Arg Val Thr Ser Ile Lys Ile Asp Pro Tyr Leu Asn Thr Asp Ala Gly
            35                  40                  45

Thr Met Ser Pro Phe Glu His Gly Glu Val Phe Val Leu Asp Asp Gly
        50                  55                  60

Gly Glu Val Asp Leu Asp Leu Gly Asn Tyr Glu Arg Phe Leu Asp Ile
65                  70                  75                  80

Lys Leu Thr Arg Asp Asn Asn Ile Thr Thr Gly Lys Ile Tyr Gln Ser
                85                  90                  95

Val Ile Asp Lys Glu Arg Arg Gly Asp Tyr Leu Gly Lys Thr Val Gln
            100                 105                 110

Val Val Pro His Ile Thr Asp Glu Ile Gln Glu Trp Ile Glu Arg Val
        115                 120                 125

Ala Met Asn Pro Val Asp Gly Thr Glu Glu Ala Asp Val Cys Val
    130                 135                 140

Ile Glu Leu Gly Gly Thr Ile Gly Asp Ile Glu Ser Met Pro Phe Ile
145                 150                 155                 160

Glu Ala Leu Gly Gln Phe Ser Tyr Arg Val Gly Pro Gly Asn Phe Cys
                165                 170                 175

Leu Val His Val Ser Leu Val Pro Val Leu Asn Val Val Gly Glu Gln
            180                 185                 190

Lys Thr Lys Pro Thr Gln His Ser Val Arg Gly Leu Arg Gly Leu Gly
        195                 200                 205

Leu Met Pro Asp Ile Leu Ala Cys Arg Ser Thr His Pro Leu Glu Glu
    210                 215                 220
```

His Val Lys Val Lys Leu Ala Gln Phe Cys His Val Pro Ile Pro Asn
225                 230                 235                 240

Ile Ile Asn Leu His Asp Val Thr Asn Ile Trp His Ile Pro Leu Leu
            245                 250                 255

Leu Arg Asp Gln Lys Ala His Glu Ala Ile Leu Lys Val Leu Asp Leu
        260                 265                 270

Gln Cys Val Gly Lys Val Ala Arg Glu Pro Gln Leu Ser Glu Trp Thr
    275                 280                 285

Glu Arg Ala Ser Arg Cys Asp Arg Leu Lys Thr Pro Val Arg Ile Ala
290                 295                 300

Met Val Gly Lys Tyr Thr Gly Leu Ser Asp Ser Tyr Leu Ser Val Ile
305                 310                 315                 320

Lys Ala Leu Leu His Ala Ser Val Ala Leu Asp Arg Lys Leu Val Val
            325                 330                 335

Asp Trp Val Pro Ser Cys Asp Leu Glu Asp Ser Thr Ala Glu Glu Thr
        340                 345                 350

Pro Asp Ala Tyr Glu Lys Ala Trp Glu Ser Leu Lys Gly Ala Asp Gly
    355                 360                 365

Val Leu Val Pro Gly Gly Phe Gly Asp Arg Gly Val Gln Gly Lys Ile
370                 375                 380

Leu Ala Ala Lys Tyr Ala Arg Glu Asn Asn Ile Pro Tyr Leu Gly Ile
385                 390                 395                 400

Cys Leu Gly Met Gln Ile Ala Val Ile Glu Phe Ala Arg Ser Ile Met
            405                 410                 415

Lys Leu His Gly Ala Asn Ser Thr Glu Phe Asp Pro Thr Thr Lys Thr
        420                 425                 430

Pro Cys Val Ile Phe Met Pro Glu Gly Ser Lys Thr His Met Gly Ala
    435                 440                 445

Thr Met Arg Leu Gly Ser Arg Arg Thr Phe Phe Gln Val Thr Asn Cys
450                 455                 460

Lys Ser Ala Lys Leu Tyr Gly Asn Val Ser Tyr Ile Asp Glu Arg His
465                 470                 475                 480

Arg His Arg Tyr Glu Val Asn Pro Asp Met Val Pro Glu Phe Glu Lys
            485                 490                 495

Ala Gly Leu Ser Phe Val Gly Arg Asp Glu Ser Gly Lys Arg Met Glu
        500                 505                 510

Ile Ile Glu Leu Pro Thr His Arg Phe Phe Val Gly Val Gln Phe His
    515                 520                 525

Pro Glu Phe Lys Ser Arg Pro Gly Asn Pro Ser Pro Leu Phe Leu Gly
530                 535                 540

Leu Val Ala Ala Ser Ser Gly Gln Leu Asp Gln Arg Gly Val Ile Ser
545                 550                 555                 560

Lys Thr Ser Arg Cys Ile Ser Asn Thr Gly Gly Ala Ser Lys Leu Lys
            565                 570                 575

Ala Cys Gln Asn Gly His Leu Met Lys Pro Leu Lys Gly Leu Val Asn
        580                 585                 590

Gly His Tyr Ser Thr Thr Ser Asn Gly Ala Ile Pro Ile
    595                 600                 605

<210> SEQ ID NO 79
<211> LENGTH: 1776
<212> TYPE: DNA
<213> ORGANISM: Arabidopsis thaliana

<400> SEQUENCE: 79

```
atgaagtacg ttttggtgac aggaggagtg gtgagtggtc ttggcaaagg tgtcactgct      60
agtagcattg gacttctcct tcaagcatgt ggtcttcgtg tcacttccat taaaattgat     120
ccttatctta acactgatgc tggaacaatg tctccgtttg agcatggaga agtatttgta     180
ttggatgatg gtggagaggt ggatttggac cttggaaact atgaacgatt tttagacagt     240
acattgaccc gtgacaacaa tataactact ggaaagatat accagtcagt tattgacaag     300
gaaaggaagg gggactacct cggaagaact gtacaggttg ttcctcatgt tactgacgca     360
atccaagagt ggattgagcg tgtagctaat gttcctgtgg atggaaagga aggtcctcct     420
gatgtttgtg tcatcgaatt aggcgggact ataggtgata ttgaatctat gcccttttatt    480
gaggcccttg gtcaattctc gtataaagtt ggacctggta atttctgctt ggttcatgtc     540
agccttgtgc ctgttctcag tgttgttggt gaacagaaga cgaagccaac ccagcatagt     600
gtgcgaggcc tcaggagcct tggtttgaca ccaaatatcc tagcatgtcg cagcacgaag     660
gcacttgaag aaaatgtcaa gacaaaacta tctcaatttt gccatgtgcc ggaagtgaat     720
atagtaacgc tctatgatgt tccaaatatt tggcacgttc ctctgctttt aagggatcaa     780
aaagctcatg aagcgatcct aagagagtta atcttagta atgctataaa gcctgacttg      840
acagaatgga ctgcaaggac taaaatttat gacacactgc aagaccctgt gagaatagct     900
atggttggaa agtacactgg ccttactgat tcttaccttt ccgtgttgaa ggccctttttg    960
catgcttctg ttgcatgtca caagaagctt gtcatagagt gggttgcagc tagtgacctt    1020
gaagagataa ctgcacaaga gacgccagat gtccataagg ctgcatggga tcttttgaag    1080
ggtgctgatg gtatcctagt accaggaggg tttggtgata gaggagtgca agggaagata    1140
cttgctacaa agtacgcccg tgaaaatcaa gtccctttcc ttggcatatg cctgggaatg    1200
cagctggctg ttgttgaatt tgcccgctcc attcttggtt ttcacgatgc aaacagcaca    1260
gagtttgaac cagaaacttc aagcccttgc atcatattta tgccagaagg atccacaact    1320
catatggggg gcacaatgcg cttagggtca aggaagactt acttccaggt tgctgattgc    1380
aagtctgcca agctgtacgg taatgcaaag tttgtagatg agcgacacag gcacagatat    1440
gaggtaaatc cagatatgat atcagaaatt gagaaggctg gcctctcctt tgttgggaaa    1500
gatgagactg gcgtcgtat ggagattgtt gaactaccaa gtcatccata ctttgtgggt    1560
gctcagttcc atcctgaatt caagtccaga cctgggaaac cttctgcatt gtttctaggt    1620
cttatcgcag cagcgtctgg gtgtctagaa tcagtattgc aaacaggtgg caaggtgaac    1680
atagtttcga aaaatggagt agccaatgga tctgcaatgg ggaaagttca tcagaacggc    1740
aatgtctata gcaatggaaa cgggcttcac cactga                              1776
```

<210> SEQ ID NO 80
<211> LENGTH: 591
<212> TYPE: PRT
<213> ORGANISM: Arabidopsis thaliana

<400> SEQUENCE: 80

```
Met Lys Tyr Val Leu Val Thr Gly Gly Val Val Ser Gly Leu Gly Lys
  1               5                  10                  15

Gly Val Thr Ala Ser Ser Ile Gly Leu Leu Leu Gln Ala Cys Gly Leu
                 20                  25                  30

Arg Val Thr Ser Ile Lys Ile Asp Pro Tyr Leu Asn Thr Asp Ala Gly
             35                  40                  45
```

-continued

```
Thr Met Ser Pro Phe Glu His Gly Glu Val Phe Val Leu Asp Asp Gly
    50                  55                  60
Gly Glu Val Asp Leu Asp Leu Gly Asn Tyr Glu Arg Phe Leu Asp Ser
65                  70                  75                  80
Thr Leu Thr Arg Asp Asn Asn Ile Thr Thr Gly Lys Ile Tyr Gln Ser
                85                  90                  95
Val Ile Asp Lys Glu Arg Lys Gly Asp Tyr Leu Gly Arg Thr Val Gln
            100                 105                 110
Val Val Pro His Val Thr Asp Ala Ile Gln Glu Trp Ile Glu Arg Val
            115                 120                 125
Ala Asn Val Pro Val Asp Gly Lys Glu Gly Pro Pro Asp Val Cys Val
130                 135                 140
Ile Glu Leu Gly Gly Thr Ile Gly Asp Ile Glu Ser Met Pro Phe Ile
145                 150                 155                 160
Glu Ala Leu Gly Gln Phe Ser Tyr Lys Val Gly Pro Gly Asn Phe Cys
                165                 170                 175
Leu Val His Val Ser Leu Val Pro Val Leu Ser Val Val Gly Glu Gln
            180                 185                 190
Lys Thr Lys Pro Thr Gln His Ser Val Arg Gly Leu Arg Ser Leu Gly
            195                 200                 205
Leu Thr Pro Asn Ile Leu Ala Cys Arg Ser Thr Lys Ala Leu Glu Glu
210                 215                 220
Asn Val Lys Thr Lys Leu Ser Gln Phe Cys His Val Pro Glu Val Asn
225                 230                 235                 240
Ile Val Thr Leu Tyr Asp Val Pro Asn Ile Trp His Val Pro Leu Leu
                245                 250                 255
Leu Arg Asp Gln Lys Ala His Glu Ala Ile Leu Arg Glu Leu Asn Leu
            260                 265                 270
Ser Asn Ala Ile Lys Pro Asp Leu Thr Glu Trp Thr Ala Arg Thr Lys
            275                 280                 285
Ile Tyr Asp Thr Leu Gln Asp Pro Val Arg Ile Ala Met Val Gly Lys
            290                 295                 300
Tyr Thr Gly Leu Thr Asp Ser Tyr Leu Ser Val Leu Lys Ala Leu Leu
305                 310                 315                 320
His Ala Ser Val Ala Cys His Lys Lys Leu Val Ile Glu Trp Val Ala
                325                 330                 335
Ala Ser Asp Leu Glu Glu Ile Thr Ala Gln Glu Thr Pro Asp Val His
            340                 345                 350
Lys Ala Ala Trp Asp Leu Leu Lys Gly Ala Asp Gly Ile Leu Val Pro
            355                 360                 365
Gly Gly Phe Gly Asp Arg Gly Val Gln Gly Lys Ile Leu Ala Thr Lys
370                 375                 380
Tyr Ala Arg Glu Asn Gln Val Pro Phe Leu Gly Ile Cys Leu Gly Met
385                 390                 395                 400
Gln Leu Ala Val Val Glu Phe Ala Arg Ser Ile Leu Gly Phe His Asp
                405                 410                 415
Ala Asn Ser Thr Glu Phe Glu Pro Glu Thr Ser Ser Pro Cys Ile Ile
            420                 425                 430
Phe Met Pro Glu Gly Ser Thr His Met Gly Thr Met Arg Leu
            435                 440                 445
Gly Ser Arg Lys Thr Tyr Phe Gln Val Ala Asp Cys Lys Ser Ala Lys
450                 455                 460
Leu Tyr Gly Asn Ala Lys Phe Val Asp Glu Arg His Arg His Arg Tyr
```

| | | | |
|---|---|---|---|
| 465 | 470 | 475 | 480 |

Glu Val Asn Pro Asp Met Ile Ser Glu Ile Glu Lys Ala Gly Leu Ser
            485                  490                495

Phe Val Gly Lys Asp Glu Thr Gly Arg Arg Met Glu Ile Val Glu Leu
         500                  505                510

Pro Ser His Pro Tyr Phe Val Gly Ala Gln Phe His Pro Glu Phe Lys
         515                  520                525

Ser Arg Pro Gly Lys Pro Ser Ala Leu Phe Leu Gly Leu Ile Ala Ala
     530                  535                540

Ala Ser Gly Cys Leu Glu Ser Val Leu Gln Thr Gly Gly Lys Val Asn
545                550                555            560

Ile Val Ser Lys Asn Gly Val Ala Asn Gly Ser Ala Met Gly Lys Val
         565                  570                575

His Gln Asn Gly Asn Val Tyr Ser Asn Gly Asn Gly Leu His His
         580                  585                590

<210> SEQ ID NO 81
<211> LENGTH: 1911
<212> TYPE: DNA
<213> ORGANISM: Glycine max

<400> SEQUENCE: 81

| | | | |
|---|---|---|---|
| atgaagtacc tgttggtgac gggtggagtt gtgagtggac ttgggaaagg agtcactgca | | | 60 |
| agcagtattg gagtactcct tcaggcttgt ggctttcggg ttacttctat caagattgat | | | 120 |
| ccctatctga acactgatgc agggacaatg tctccttttg agcatgggga agtgtttgtt | | | 180 |
| ttagatgatg gcggtgaggt tgaccttgat cttggaaact atgaacgttt cttggacctc | | | 240 |
| aaattaactc gtgacaataa tatcacaact gggaaaatat atcagtctgt aattgaaaag | | | 300 |
| gagagaagag gagattatct tggcaagact gtgcaggttg ttccacacat tactgatgcc | | | 360 |
| atccaagaat ggatagagcg tgtggcacag ataccagttg atggaaaaga aggcccagct | | | 420 |
| gatgtttgtg ttattgagtt gggtggaact attggagata tcgagtctat gccttttatt | | | 480 |
| gaagcacttg gccagttttc ataccgtgtt ggccctggta acttctgttt agttcatgtc | | | 540 |
| agcttggtgc ctgttatcaa tgttgttggt gagcagaaaa caaagccaac ccaacacagt | | | 600 |
| gtccgccaac ttagagggtt agggttgacc ccaaatcttc ttgcttgtcg cagttcaaag | | | 660 |
| gaacttgatg acaacattaa ggaaaaactt tctcaatttt gtcatgttcc gtcatcaagc | | | 720 |
| atactaactc tctatgatgt tccaaatatt tggcacattc ctttgctatt aagtgaccaa | | | 780 |
| aaggcgcatg atgcaatcct gaaaacatta aacctgcgag tgttgctac agagcctaat | | | 840 |
| tttaaggagt ggattacaac aacaaagta tatgacaaat tcatgaaat ggtaagtttc | | | 900 |
| aattttctta atatatcatc taaaaaagct aatatattc atgaatctgt gagttccaat | | | 960 |
| attcaactct ctatagttag aattgcaatg gtgggaaaat atactaaccct ctcagatgca | | | 1020 |
| tatctttctg tactgaaggc acttttgcat gcttctgttg cttgcaatca tgagcttgtt | | | 1080 |
| gtggatttgg ttcccgctga acatctcgaa gatgataccct ctaaagagga tcctgatgca | | | 1140 |
| tataaagctg cttggggtct tttgaaggga gctaatggga ttctagttcc aggaggttt | | | 1200 |
| ggtgacagag gagtggaagg aaaaattctt gctgccaagt atgctcgaga aaatagcatt | | | 1260 |
| ccatatctgg gcatttgctt ggggatgcaa ataggtgtaa ttgagttttc aagatctgtt | | | 1320 |
| ctgggtcttc atgatgctaa tagcacagaa tttgatccca aaaccaaaaa cccttgtgtc | | | 1380 |
| atatttatgc cagaaggttc aaagactcat atggggggaa ctatgcgtct tggttcaagg | | | 1440 |

```
agaacttact ttcatgttgc tgactgcaaa tcagccaagt tgtatggtaa tgcaagcttt    1500
gttgatgagc gacatcggca tagatacgag gttaatcctg atatgatatc acaactcgag    1560
agtgctggtc tatcttttgt tggcaaagac gaaactggga agcgcatgga gatagttgaa    1620
tttcctggtc atcctttctt cattggtgct cagtttcatc ctgagttcaa gtccagacca    1680
gggaaacctt ctccattatt cttaggatta atatcagcag catgtgagag gacagttgtg    1740
cctgcaagca aaggttatgg caagttaaca aatgggatac actcaccaat gttgaaagca    1800
gcagcagcac ataatggaaa taatgggttc aaatcttcca atagttcctt aaatggtgta    1860
tatacaagta caactaccaa tggggtgtgt gttgatggga ggagctgtta a              1911
```

```
<210> SEQ ID NO 82
<211> LENGTH: 636
<212> TYPE: PRT
<213> ORGANISM: Glycine max

<400> SEQUENCE: 82

Met Lys Tyr Leu Leu Val Thr Gly Gly Val Val Ser Gly Leu Gly Lys
 1               5                  10                  15

Gly Val Thr Ala Ser Ser Ile Gly Val Leu Gln Ala Cys Gly Phe
                20                  25                  30

Arg Val Thr Ser Ile Lys Ile Asp Pro Tyr Leu Asn Thr Asp Ala Gly
            35                  40                  45

Thr Met Ser Pro Phe Glu His Gly Glu Val Phe Val Leu Asp Asp Gly
        50                  55                  60

Gly Glu Val Asp Leu Asp Leu Gly Asn Tyr Glu Arg Phe Leu Asp Leu
65                  70                  75                  80

Lys Leu Thr Arg Asp Asn Asn Ile Thr Thr Gly Lys Ile Tyr Gln Ser
                85                  90                  95

Val Ile Glu Lys Glu Arg Arg Gly Asp Tyr Leu Gly Lys Thr Val Gln
            100                 105                 110

Val Val Pro His Ile Thr Asp Ala Ile Gln Glu Trp Ile Glu Arg Val
        115                 120                 125

Ala Gln Ile Pro Val Asp Gly Lys Glu Gly Pro Ala Asp Val Cys Val
130                 135                 140

Ile Glu Leu Gly Gly Thr Ile Gly Asp Ile Glu Ser Met Pro Phe Ile
145                 150                 155                 160

Glu Ala Leu Gly Gln Phe Ser Tyr Arg Val Gly Pro Gly Asn Phe Cys
                165                 170                 175

Leu Val His Val Ser Leu Val Pro Val Ile Asn Val Val Gly Glu Gln
            180                 185                 190

Lys Thr Lys Pro Thr Gln His Ser Val Arg Gln Leu Arg Gly Leu Gly
        195                 200                 205

Leu Thr Pro Asn Leu Leu Ala Cys Arg Ser Ser Lys Glu Leu Asp Asp
210                 215                 220

Asn Ile Lys Glu Lys Leu Ser Gln Phe Cys His Val Pro Ser Ser Ser
225                 230                 235                 240

Ile Leu Thr Leu Tyr Asp Val Pro Asn Ile Trp His Ile Pro Leu Leu
                245                 250                 255

Leu Ser Asp Gln Lys Ala His Asp Ala Ile Leu Lys Thr Leu Asn Leu
            260                 265                 270

Arg Gly Val Ala Thr Glu Pro Asn Phe Lys Glu Trp Ile Thr Thr Thr
        275                 280                 285

Lys Val Tyr Asp Lys Phe His Glu Met Val Ser Phe Asn Phe Ser Asn
```

```
              290                 295                 300
Ile Ser Ser Lys Lys Ala Asn Ile Phe His Glu Ser Val Ser Asn
305                 310                 315                 320

Ile Gln Leu Ser Ile Val Arg Ile Ala Met Val Gly Lys Tyr Thr Asn
                325                 330                 335

Leu Ser Asp Ala Tyr Leu Ser Val Leu Lys Ala Leu Leu His Ala Ser
                340                 345                 350

Val Ala Cys Asn His Glu Leu Val Val Asp Leu Val Pro Ala Glu His
                355                 360                 365

Leu Glu Asp Asp Thr Ser Lys Glu Asp Pro Asp Ala Tyr Lys Ala Ala
                370                 375                 380

Trp Gly Leu Leu Lys Gly Ala Asn Gly Ile Leu Val Pro Gly Gly Phe
385                 390                 395                 400

Gly Asp Arg Gly Val Glu Gly Lys Ile Leu Ala Ala Lys Tyr Ala Arg
                405                 410                 415

Glu Asn Ser Ile Pro Tyr Leu Gly Ile Cys Leu Gly Met Gln Ile Gly
                420                 425                 430

Val Ile Glu Phe Ser Arg Ser Val Leu Gly Leu His Asp Ala Asn Ser
                435                 440                 445

Thr Glu Phe Asp Pro Lys Thr Lys Asn Pro Cys Val Ile Phe Met Pro
                450                 455                 460

Glu Gly Ser Lys Thr His Met Gly Gly Thr Met Arg Leu Gly Ser Arg
465                 470                 475                 480

Arg Thr Tyr Phe His Val Ala Asp Cys Lys Ser Ala Lys Leu Tyr Gly
                485                 490                 495

Asn Ala Ser Phe Val Asp Glu Arg His Arg His Arg Tyr Glu Val Asn
                500                 505                 510

Pro Asp Met Ile Ser Gln Leu Glu Ser Ala Gly Leu Ser Phe Val Gly
                515                 520                 525

Lys Asp Glu Thr Gly Lys Arg Met Glu Ile Val Glu Phe Pro Gly His
                530                 535                 540

Pro Phe Phe Ile Gly Ala Gln Phe His Pro Glu Phe Lys Ser Arg Pro
545                 550                 555                 560

Gly Lys Pro Ser Pro Leu Phe Leu Gly Leu Ile Ser Ala Ala Cys Glu
                565                 570                 575

Arg Thr Val Val Pro Ala Ser Lys Gly Tyr Gly Lys Leu Thr Asn Gly
                580                 585                 590

Ile His Ser Pro Met Leu Lys Ala Ala Ala His Asn Gly Asn Asn
                595                 600                 605

Gly Phe Lys Ser Ser Asn Ser Ser Leu Asn Gly Val Tyr Thr Ser Thr
                610                 615                 620

Thr Thr Asn Gly Val Cys Val Asp Gly Arg Ser Cys
625                 630                 635
```

<210> SEQ ID NO 83
<211> LENGTH: 1164
<212> TYPE: DNA
<213> ORGANISM: Oryza sativa

<400> SEQUENCE: 83

```
atgtcgtcgc agcaatggct tggtgacggc acggcgcgga ggtggaggga gctccatggt    60
gagagcgact gggacggcct cctggacccg ttcgaccccg acctccgccg caccgtcatc   120
cgctacggcg agatggcgca ggcgacgtac gacgccttca ccacgagaa gctctcgccg   180
```

```
cacgcgggcc tctcgaggtt cgccgcgcgc cgcttcttcg agcgggcgca gctgccgggc        240
cactccgcgg cgtaccgcgt cgccaggtgc agggagagca actggatcgg gtacgtcgcg        300
gtggccaccg acgaagggaa ggctgcgctc gggcgccgcg acatcgtcgt cgcgtggcgc        360
ggcacggtgc agtcgctgga gtggatcaag gacatggact cgtcatggt gccacccaag         420 ggcctcctcc gggacaaagc ttccgacgcc atggtgcatc gagggtggct gtccatgtac        480
acctccaggg actctgagtc cagccacaac aaggacagtg ctcgagatca ggtgttgagc        540
gaggtggcga agctggtgag catgtaccag gacgaggaac tgagcatcac ggtgacggga        600
cacagcctcg gcgccgcact cgcgacgctg aacgcgttcg acatcgtcga aacgggtac         660 aacagggcac cccgcgccgc ggcagcggcg gcgggctgcc cggtcaccgc gttcgtgttc        720
gccagcccgc gcgtcggcgg gcacggcttc aagcgccgct cgacggcgc gcgtggcctc         780 ggcctccgcc tcctccgcgt ccgcaacgcg cgcgacgtcg tccccaggta cccgccggcg        840
ccgccgtacc acggcgtggg cacagagctg gcgatcgaca cgggcgagtc gccgtacctg        900
aggaggcccg ggaacgagct ggtgtggcac aacctcgagt gctacctgca cggcgtggcc        960
ggcgcgcgcg gcggcgaggc cgggcggttc aagctcgccg tggagcgcga cgtggcgctg       1020
gcgaacaagt cctacggcgc gctgcgcgac gagcacgccg tgccggccgg tggtggatc        1080 ccgtcgaaca ggggcatggt gagaggcgcc gatggccgct ggactctgat ggaccgcgag       1140
gaagatgagg atagtgcaga gtaa                                              1164

<210> SEQ ID NO 84
<211> LENGTH: 387
<212> TYPE: PRT
<213> ORGANISM: Oryza sativa

<400> SEQUENCE: 84

Met Ser Ser Gln Gln Trp Leu Gly Asp Gly Thr Ala Arg Arg Trp Arg
1               5                   10                  15

Glu Leu His Gly Glu Ser Asp Trp Asp Gly Leu Asp Pro Phe Asp
            20                  25                  30

Leu Asp Leu Arg Arg Thr Val Ile Arg Tyr Gly Glu Met Ala Gln Ala
        35                  40                  45

Thr Tyr Asp Ala Phe Asn His Glu Lys Leu Ser Pro His Ala Gly Leu
    50                  55                  60

Ser Arg Phe Ala Ala Arg Arg Phe Phe Glu Arg Ala Gln Leu Pro Gly
65                  70                  75                  80

His Ser Ala Ala Tyr Arg Val Ala Arg Cys Arg Glu Ser Asn Trp Ile
                85                  90                  95

Gly Tyr Val Ala Val Ala Thr Asp Glu Gly Lys Ala Ala Leu Gly Arg
            100                 105                 110

Arg Asp Ile Val Val Ala Trp Arg Gly Thr Val Gln Ser Leu Glu Trp
        115                 120                 125

Ile Lys Asp Met Asp Phe Val Met Val Pro Pro Lys Gly Leu Leu Arg
    130                 135                 140

Asp Lys Ala Ser Asp Ala Met Val His Arg Gly Trp Leu Ser Met Tyr
145                 150                 155                 160

Thr Ser Arg Asp Ser Glu Ser Ser His Asn Lys Asp Ser Ala Arg Asp
                165                 170                 175

Gln Val Leu Ser Glu Val Ala Lys Leu Val Ser Met Tyr Gln Asp Glu
            180                 185                 190

Glu Leu Ser Ile Thr Val Thr Gly His Ser Leu Gly Ala Ala Leu Ala
```

```
                 195                 200                 205
Thr Leu Asn Ala Phe Asp Ile Val Glu Asn Gly Tyr Asn Arg Ala Pro
    210                 215                 220

Arg Ala Ala Ala Ala Ala Gly Cys Pro Val Thr Ala Phe Val Phe
225                 230                 235                 240

Ala Ser Pro Arg Val Gly Gly His Gly Phe Lys Arg Arg Phe Asp Gly
                245                 250                 255

Ala Arg Gly Leu Gly Leu Arg Leu Leu Arg Val Arg Asn Ala Arg Asp
            260                 265                 270

Val Val Pro Arg Tyr Pro Pro Ala Pro Pro Tyr His Gly Val Gly Thr
        275                 280                 285

Glu Leu Ala Ile Asp Thr Gly Glu Ser Pro Tyr Leu Arg Arg Pro Gly
    290                 295                 300

Asn Glu Leu Val Trp His Asn Leu Glu Cys Tyr Leu His Gly Val Ala
305                 310                 315                 320

Gly Ala Arg Gly Gly Glu Ala Gly Arg Phe Lys Leu Ala Val Glu Arg
                325                 330                 335

Asp Val Ala Leu Ala Asn Lys Ser Tyr Gly Ala Leu Arg Asp Glu His
            340                 345                 350

Ala Val Pro Ala Gly Trp Trp Ile Pro Ser Asn Arg Gly Met Val Arg
        355                 360                 365

Gly Ala Asp Gly Arg Trp Thr Leu Met Asp Arg Glu Glu Asp Glu Asp
    370                 375                 380

Ser Ala Glu
385

<210> SEQ ID NO 85
<211> LENGTH: 1263
<212> TYPE: DNA
<213> ORGANISM: Zea mays

<400> SEQUENCE: 85
atgcagctgc gcaccagaca tgtccgttcc atgacccagt cccagcacga tccatgtcat      60
gcctttgccg tttgcaatct tcgtcgtcag aatcagaagc aaaccccga gcaagctacc      120 gtcactgtgt acaccagaag aagcaccagc aaggcaactg cgagcgagct gcgttacgtg     180
cccagcaaca tgtcccagca cggcggcctc ggggacacgg cccggcggtg gcgcgagctc     240
cacggcggcg acaacagctg gacggggctg ctggacccgc tggacctcga cctgcgccgc     300
accgtgctcc gctacggcga gatggcgcag gccacctacg acgccttcaa ctgcgagcgc     360
gcgtcgccgc acgcggggct ctcccgcttc gccagggcgc gcttcttcga ccgggcgcgg     420
ctgccggcgc acgccgccgc gtaccgggtc accaggttcc tgtacgccac gtcgtcggta     480
gccgtgccgg ccgccttcat gctctggtcc gtggccgggt cgcgccggcg gtgcagggag     540
tctaactgga tcggctacgt cgcggcggcc accgacgagg ggaaagccgc gctcgggcgc     600
cgcgacatcg tcgtcgcgtg gcgcggcacc gtggaggcgc tggagtgggc cgacgcccga     660
cgacctcgag ttccccatgg tgccgacgga aggccgcctc ggggacggcg acgcctgcga     720
cgccatggtg caccgcggct ggctgtccat gtacacctcc gccgaccccg cgtccagcca     780
caaccaggac agcgcgcggg accaggcgct gggcgaggtg cggaggctgg tggacgcgta     840
caaggacgag gagctcagcg tcaccgtgac gggccacagc ctcggcgcgg cgctcgccac     900
gctcaacgcg ttcgacatcg ccgccaacgg ctacaacgtg gcggcgacgg cgacggccgc     960
ctgccccgtg accgcgttcg cgttcgccag cccgcgcgtc ggcggcgctg gcttcaggaa    1020
```

```
gcggttcgac gctgtcccgg ggctgcggct cctccgcgtc cgcaacgccc gcgacgtcgt    1080
gcccaagtac ccggccgtgt tctaccacga cgtcggcgcg agctcgcgg tcgacacggg    1140 ggagtcgccg tacctgagga gccccgggcg cgagcggacc tgccacaacc tcgaggtgta    1200
cctgcacggc gtggcgggca cgcgaggcgc gcgcggaggg ttcgagctcg ccgtggcgcg    1260
tga                                                                 1263
```

<210> SEQ ID NO 86
<211> LENGTH: 420
<212> TYPE: PRT
<213> ORGANISM: Zea mays

<400> SEQUENCE: 86

```
Met Gln Leu Arg Thr Arg His Val Arg Ser Met Thr Gln Ser Gln His
1               5                   10                  15

Asp Pro Cys His Ala Phe Ala Val Cys Asn Leu Arg Arg Gln Asn Gln
            20                  25                  30

Lys Gln Thr Pro Glu Gln Ala Thr Val Thr Val Tyr Thr Arg Arg Ser
        35                  40                  45

Thr Ser Lys Ala Thr Ala Ser Glu Leu Arg Tyr Val Pro Ser Asn Met
    50                  55                  60

Ser Gln His Gly Gly Leu Gly Asp Thr Ala Arg Arg Trp Arg Glu Leu
65                  70                  75                  80

His Gly Gly Asp Asn Ser Trp Thr Gly Leu Leu Asp Pro Leu Asp Leu
                85                  90                  95

Asp Leu Arg Arg Thr Val Leu Arg Tyr Gly Glu Met Ala Gln Ala Thr
            100                 105                 110

Tyr Asp Ala Phe Asn Cys Glu Arg Ala Ser Pro His Ala Gly Leu Ser
        115                 120                 125

Arg Phe Ala Arg Ala Arg Phe Phe Asp Arg Ala Arg Leu Pro Ala His
    130                 135                 140

Ala Ala Ala Tyr Arg Val Thr Arg Phe Leu Tyr Ala Thr Ser Ser Val
145                 150                 155                 160

Ala Val Pro Ala Ala Phe Met Leu Trp Ser Val Ala Gly Ser Arg Arg
                165                 170                 175

Arg Cys Arg Glu Ser Asn Trp Ile Gly Tyr Val Ala Ala Ala Thr Asp
            180                 185                 190

Glu Gly Lys Ala Ala Leu Gly Arg Arg Asp Ile Val Val Ala Trp Arg
        195                 200                 205

Gly Thr Val Glu Ala Leu Glu Trp Ala Asp Ala Arg Arg Pro Arg Val
    210                 215                 220

Pro His Gly Ala Asp Gly Arg Pro Arg Gly Arg Arg Leu Arg
225                 230                 235                 240

Arg His Gly Ala Pro Arg Leu Ala Val His Val His Leu Arg Arg Pro
                245                 250                 255

Arg Val Gln Pro Gln Pro Gly Gln Arg Ala Gly Pro Gly Ala Gly Arg
            260                 265                 270

Gly Ala Glu Ala Gly Gly Arg Val Gln Gly Arg Gly Ala Gln Arg His
        275                 280                 285

Arg Asp Gly Pro Gln Pro Arg Arg Gly Ala Arg His Ala Gln Arg Val
    290                 295                 300

Arg His Arg Arg Gln Arg Leu Gln Arg Gly Gly Asp Gly Asp Gly Arg
305                 310                 315                 320
```

Leu Pro Arg Asp Arg Val Arg Val Arg Gln Pro Ala Arg Arg Arg
              325                 330                 335

Trp Leu Gln Glu Ala Val Arg Arg Cys Pro Gly Ala Ala Pro Pro
              340                 345                 350

Arg Pro Gln Arg Pro Arg Arg Ala Gln Val Pro Gly Arg Val Leu
              355                 360                 365

Pro Arg Arg Arg Gly Ala Arg Gly Arg His Gly Gly Val Ala Val
      370                 375                 380

Pro Glu Glu Pro Arg Ala Arg Ala Asp Leu Pro Gln Pro Arg Gly Val
385                 390                 395                 400

Pro Ala Arg Arg Gly Gly His Ala Arg Arg Ala Arg Arg Val Arg Ala
              405                 410                 415

Arg Arg Gly Ala
          420

<210> SEQ ID NO 87
<211> LENGTH: 1227
<212> TYPE: DNA
<213> ORGANISM: Sorghum bicolor

<400> SEQUENCE: 87
atgatgtcca accacggcgg cctcggcgac acggcccggc ggtggcgcga gctccacggc     60
gtcggcggcg acaacagcgg ctgggcgggg ctgctggacc cgctggacct cgacctgcgc    120
cgcaccgtgc tccgctacgg cgagatggcg caggcgacct acgacgcctt caaccgcgag    180
cgttcgtcgc cgcacgcggg tctgtcccgc ttcgccaggg cgcgcttctt cgaccgggtg    240
cggctgccgg cgcacgccgc cgcgtaccgg gtcaccaggt tcctgtacgc cacgtcgtcg    300
gtggctttgc cggacgcctt catgctgagg tccgtgtcca ggtcgcgccg gtgcagggag    360
tccaactgga tcggctacgt cgcggtggcc accgacgaag ggaaggccgc gctgggccgc    420
cgcgacgtcg tcgtcgtgtg cgcggcacc atgcagaagc tggagtgggc cgacgacctc    480
gagttcccca tggtgtcgac caaaggcctc ctcggcgatg ccaggccgc ctgcgatgcc    540 atggtgcacc gtggctggct gtccatgtac acctccatcg accggcgtc cagccacaac    600 caggacagcg cgcggcacca ggcgctgagc gaggtgcgga ggctggtgga cgcgtacagc    660
gacgaggagc gcagcatcac cgtcgtggga cacagcctcg gcgcggcgct cgccacgctc    720
aacgcgttcg acatcgccgc caacggctac aacgtggcga cgggcgcggc ggcctgcccg    780
gtgaccgcgt tcgcgttcgc cagcccgcgc gtcggcggcg cgggcttcaa gaagcggttc    840
gacgccgtgc cggggctgcg tctcctgcgc gtccggaacg cccgcgacgt cgtgcccaag    900
tacccgatcg tgttctacca cgacgtcggc gcggagctcg cgatcgacac ggggagtcg    960 ccgtacctga ggagcccgg gcgcgagcat acctggcaca acctcgaggt gtacctgcac   1020
ggcgtggcgg gcacgcgggg cgcgcgcgga gggttcgagc tcgccgtggc gcgggacgtg   1080
gcgctggtga acaagctata cgacgtgctg tgggacgact acggggtgcc gcctgggtgg   1140
tgggtgccgc tgaacaaggg catggtggag ggcgccgacg ggcgctggag cttgatggac   1200
tgcgaggagg acgaggaaga tgagtag                                      1227

<210> SEQ ID NO 88
<211> LENGTH: 408
<212> TYPE: PRT
<213> ORGANISM: Sorghum bicolor

<400> SEQUENCE: 88

```
Met Met Ser Asn His Gly Gly Leu Gly Asp Thr Ala Arg Arg Trp Arg
1               5                   10                  15

Glu Leu His Gly Val Gly Gly Asp Asn Ser Gly Trp Ala Gly Leu Leu
            20                  25                  30

Asp Pro Leu Asp Leu Asp Leu Arg Arg Thr Val Leu Arg Tyr Gly Glu
                35                  40                  45

Met Ala Gln Ala Thr Tyr Asp Ala Phe Asn Arg Glu Arg Ser Ser Pro
50                      55                  60

His Ala Gly Leu Ser Arg Phe Ala Arg Ala Arg Phe Phe Asp Arg Val
65                  70                  75                  80

Arg Leu Pro Ala His Ala Ala Ala Tyr Arg Val Thr Arg Phe Leu Tyr
                85                  90                  95

Ala Thr Ser Ser Val Ala Leu Pro Asp Ala Phe Met Leu Arg Ser Val
            100                 105                 110

Ser Arg Ser Arg Arg Cys Arg Glu Ser Asn Trp Ile Gly Tyr Val Ala
            115                 120                 125

Val Ala Thr Asp Glu Gly Lys Ala Ala Leu Gly Arg Arg Asp Val Val
130                 135                 140

Val Val Trp Arg Gly Thr Met Gln Lys Leu Glu Trp Ala Asp Asp Leu
145                 150                 155                 160

Glu Phe Pro Met Val Ser Thr Lys Gly Leu Leu Gly Asp Gly Gln Ala
                165                 170                 175

Ala Cys Asp Ala Met Val His Arg Gly Trp Leu Ser Met Tyr Thr Ser
            180                 185                 190

Ile Asp Pro Ala Ser Ser His Asn Gln Asp Ser Ala Arg His Gln Ala
            195                 200                 205

Leu Ser Glu Val Arg Arg Leu Val Asp Ala Tyr Ser Asp Glu Glu Arg
210                 215                 220

Ser Ile Thr Val Val Gly His Ser Leu Gly Ala Ala Leu Ala Thr Leu
225                 230                 235                 240

Asn Ala Phe Asp Ile Ala Ala Asn Gly Tyr Asn Val Ala Thr Gly Ala
                245                 250                 255

Ala Ala Cys Pro Val Thr Ala Phe Ala Phe Ala Ser Pro Arg Val Gly
            260                 265                 270

Gly Gly Gly Phe Lys Lys Arg Phe Asp Ala Val Pro Gly Leu Arg Leu
            275                 280                 285

Leu Arg Val Arg Asn Ala Arg Asp Val Val Pro Lys Tyr Pro Ile Val
290                 295                 300

Phe Tyr His Asp Val Gly Ala Glu Leu Ala Ile Asp Thr Gly Glu Ser
305                 310                 315                 320

Pro Tyr Leu Arg Ser Pro Gly Arg Glu His Thr Trp His Asn Leu Glu
                325                 330                 335

Val Tyr Leu His Gly Val Ala Gly Thr Arg Gly Ala Arg Gly Gly Phe
            340                 345                 350

Glu Leu Ala Val Ala Arg Asp Val Ala Leu Val Asn Lys Leu Tyr Asp
            355                 360                 365

Val Leu Trp Asp Asp Tyr Gly Val Pro Pro Gly Trp Trp Val Pro Leu
370                 375                 380

Asn Lys Gly Met Val Glu Gly Ala Asp Gly Arg Trp Ser Leu Met Asp
385                 390                 395                 400

Cys Glu Glu Asp Glu Glu Asp Glu
                405
```

<210> SEQ ID NO 89
<211> LENGTH: 1260
<212> TYPE: DNA
<213> ORGANISM: Arabidopsis thaliana

<400> SEQUENCE: 89

```
atgaagagga agaagaaaga ggaggaggag gagaagttga tagtgactag agaattcgcg    60
aagagatggc gagatctgag cggtcaaaac cattggaaag ggatgttaca gccgttggat   120
caagatctcc gggaatatat catacattat ggtgagatgg ctcaggctgg ttacgatact   180
ttcaatatca acaccgaatc tcagttcgcc ggtgctagca tctactctag aaaagacttc   240
ttcgccaagg ttggtttaga gatagcacac ccgtacacaa agtacaaagt gacgaagttt   300
atatacgcga catccgatat ccacgtgcct gagtcattct tattgttccc aatttcacgt   360
gagggatggt caaaggaatc aaattggatg gttacgtgg cggtaacaga cgaccaaggc   420
acggcacttc ttggtcggag agatatcgtg gtttcttgga gaggctcagt gcaaccactt   480
gaatgggtcg aagacttcga gtttggttta gtcaacgcca taaaaatctt cggtgaaaga   540
aacgatcaag tacaaattca tcaaggttgg tattcaatct acatgtctca agatgaacga   600
tcacctttta ctaagaccaa tgctcgtgac caggtattgc gagaggttgg aagattgttg   660
gagaagtata aggacgaaga agttagtata actatatgtg gtcatagtct tggagctgca   720
ctcgcgacgc ttagtgccac tgatattgtg gctaatggtt ataaccgacc aaagagccgt   780
cctgacaagt cttgtcctgt tactgccttt gtctttgcta gtcctcgtgt tggggattca   840
gactttagga aactcttttc cggattggaa gatatccgag tgttacggac aaggaatcta   900
ccggacgtaa ttccgatcta tccaccgata ggttactccg aggtaggaga tgagtttcca   960
atagacacaa gaaagtcacc atacatgaaa tctcctggaa acctcgcaac ctttcactgc  1020
ttagagggtt acttgcatgg cgttgccggg actcaaggaa cgaacaaagc tgacttattc  1080
agactcgatg tggaaagagc catcggattg gtcaataaat cagtggatgg gttaaaagac  1140
gagtgtatgg tcccagggaa atggagggtt cttaaaaaca aaggtatggc ccaacaagac  1200
gatggatctt gggagttagt ggaccatgag attgatgata atgaagattt ggatttctga  1260
```

<210> SEQ ID NO 90
<211> LENGTH: 419
<212> TYPE: PRT
<213> ORGANISM: Arabidopsis thaliana

<400> SEQUENCE: 90

Met Lys Arg Lys Lys Glu Glu Glu Glu Lys Leu Ile Val Thr
1               5                   10                  15

Arg Glu Phe Ala Lys Arg Trp Arg Asp Leu Ser Gly Gln Asn His Trp
                20                  25                  30

Lys Gly Met Leu Gln Pro Leu Asp Gln Asp Leu Arg Glu Tyr Ile Ile
            35                  40                  45

His Tyr Gly Glu Met Ala Gln Ala Gly Tyr Asp Thr Phe Asn Ile Asn
        50                  55                  60

Thr Glu Ser Gln Phe Ala Gly Ala Ser Ile Tyr Ser Arg Lys Asp Phe
65                  70                  75                  80

Phe Ala Lys Val Gly Leu Glu Ile Ala His Pro Tyr Thr Lys Tyr Lys
                85                  90                  95

Val Thr Lys Phe Ile Tyr Ala Thr Ser Asp Ile His Val Pro Glu Ser
            100                 105                 110

Phe Leu Leu Phe Pro Ile Ser Arg Glu Gly Trp Ser Lys Glu Ser Asn

```
            115                 120                 125
Trp Met Gly Tyr Val Ala Val Thr Asp Asp Gln Gly Thr Ala Leu Leu
    130                 135                 140

Gly Arg Arg Asp Ile Val Val Ser Trp Arg Gly Ser Val Gln Pro Leu
145                 150                 155                 160

Glu Trp Val Glu Asp Phe Glu Phe Gly Leu Val Asn Ala Ile Lys Ile
                165                 170                 175

Phe Gly Glu Arg Asn Asp Gln Val Gln Ile His Gln Gly Trp Tyr Ser
            180                 185                 190

Ile Tyr Met Ser Gln Asp Glu Arg Ser Pro Phe Thr Lys Thr Asn Ala
        195                 200                 205

Arg Asp Gln Val Leu Arg Glu Val Gly Arg Leu Leu Glu Lys Tyr Lys
    210                 215                 220

Asp Glu Glu Val Ser Ile Thr Ile Cys Gly His Ser Leu Gly Ala Ala
225                 230                 235                 240

Leu Ala Thr Leu Ser Ala Thr Asp Ile Val Ala Asn Gly Tyr Asn Arg
                245                 250                 255

Pro Lys Ser Arg Pro Asp Lys Ser Cys Pro Val Thr Ala Phe Val Phe
            260                 265                 270

Ala Ser Pro Arg Val Gly Asp Ser Asp Phe Arg Lys Leu Phe Ser Gly
        275                 280                 285

Leu Glu Asp Ile Arg Val Leu Arg Thr Arg Asn Leu Pro Asp Val Ile
    290                 295                 300

Pro Ile Tyr Pro Pro Ile Gly Tyr Ser Glu Val Gly Asp Glu Phe Pro
305                 310                 315                 320

Ile Asp Thr Arg Lys Ser Pro Tyr Met Lys Ser Pro Gly Asn Leu Ala
                325                 330                 335

Thr Phe His Cys Leu Glu Gly Tyr Leu His Gly Val Ala Gly Thr Gln
            340                 345                 350

Gly Thr Asn Lys Ala Asp Leu Phe Arg Leu Asp Val Glu Arg Ala Ile
        355                 360                 365

Gly Leu Val Asn Lys Ser Val Asp Gly Leu Lys Asp Glu Cys Met Val
    370                 375                 380

Pro Gly Lys Trp Arg Val Leu Lys Asn Lys Gly Met Ala Gln Gln Asp
385                 390                 395                 400

Asp Gly Ser Trp Glu Leu Val Asp His Glu Ile Asp Asp Asn Glu Asp
                405                 410                 415

Leu Asp Phe

<210> SEQ ID NO 91
<211> LENGTH: 1206
<212> TYPE: DNA
<213> ORGANISM: Glycine max

<400> SEQUENCE: 91
atggaaaaga agatcatgaa tagcagcata gcgaaaaaat ggcgacaact cagtgggcaa      60
gatcattgga agggtctgat agaccctctg acattgatc ttcgccgcta catcattcac     120
tacggcgaaa tggctcaagc ggcatacgat gctttcaaca cggagaaagc atcaaagtac     180
gctggaagca gcagatacgc caaaaagagt ttcttctcca agttggtttt ggtgaatggc     240
aaccccttca cgtattccgt gacaaagttt ctgtatgcaa cttcggaaat tgacgtccct     300
gatgcgttca tcataaagtc gttttctagg gaggcttgga gcagggaatc gaattggata     360
gggtatgttg cggtggccac agatgaaggg aaagctgcgt tgggtagaag ggacattgtg     420
```

```
attgcgtgga gaggcacggt gcagacattg gagtgggtta atgatcttca gtttctgttg      480
gttcctgctc ctaaagtgtt tggtaagaac acagatccta aagtgcacca gggctggtac      540
tccatttaca cctctgagga ccctcgttct ccctttaata aaccagtgc tagaacccag       600 gtcctaagtg aggtgagaag actggtggag ctatataaga atgaagaaat aagcataaca      660
ataaccggtc acagtttagg tgctgcaatt gcaaccctta atgcagtgga cattgttaca      720
aatgggtaca caagccaag tgatccatct ctcaaggctt ctccagttac tgccattgtg       780
tttgccagcc caagagttgg tgacataaac tttcagaagg ttttttctgg ctacaaagat      840
ttgacaacca tacgcatccg aaacgagtta gatattgttc caaactaccc tcttgttggg      900
tattcggatg tgggtgagga gttgaagatc gatacccgaa aatcgatgta cttgaagagt      960
cctgggaatc catctagttg gcataatttg gaggcttatt tgcatggagt ggcaggaaca     1020
caaaggagca aaggagggtt caaattagag gttcatcgcg atattgcact tgtgaataag     1080
accttggatc tctaaaaga tgaattcctt gtgccagtgt catggaggac tgaaaagaat      1140
aagggtatgg ttcaacaaaa tgatggttcg tggaagctga tggatcatga agatgatgac     1200
ttttga                                                                1206
```

<210> SEQ ID NO 92
<211> LENGTH: 401
<212> TYPE: PRT
<213> ORGANISM: Glycine max

<400> SEQUENCE: 92

```
Met Glu Lys Lys Ile Met Asn Ser Ser Ile Ala Lys Lys Trp Arg Gln
1               5                   10                  15

Leu Ser Gly Gln Asp His Trp Lys Gly Leu Ile Asp Pro Leu Asp Ile
            20                  25                  30

Asp Leu Arg Arg Tyr Ile Ile His Tyr Gly Glu Met Ala Gln Ala Ala
        35                  40                  45

Tyr Asp Ala Phe Asn Thr Glu Lys Ala Ser Lys Tyr Ala Gly Ser Ser
    50                  55                  60

Arg Tyr Ala Lys Lys Ser Phe Phe Ser Lys Val Gly Leu Val Asn Gly
65                  70                  75                  80

Asn Pro Phe Thr Tyr Ser Val Thr Lys Phe Leu Tyr Ala Thr Ser Glu
                85                  90                  95

Ile Asp Val Pro Asp Ala Phe Ile Ile Lys Ser Phe Ser Arg Glu Ala
            100                 105                 110

Trp Ser Arg Glu Ser Asn Trp Ile Gly Tyr Val Ala Val Ala Thr Asp
        115                 120                 125

Glu Gly Lys Ala Ala Leu Gly Arg Arg Asp Ile Val Ile Ala Trp Arg
    130                 135                 140

Gly Thr Val Gln Thr Leu Glu Trp Val Asn Asp Leu Gln Phe Leu Leu
145                 150                 155                 160

Val Pro Ala Pro Lys Val Phe Gly Lys Asn Thr Asp Pro Lys Val His
                165                 170                 175

Gln Gly Trp Tyr Ser Ile Tyr Thr Ser Glu Asp Pro Arg Ser Pro Phe
            180                 185                 190

Asn Lys Thr Ser Ala Arg Thr Gln Val Leu Ser Glu Val Arg Arg Leu
        195                 200                 205

Val Glu Leu Tyr Lys Asn Glu Glu Ile Ser Ile Thr Ile Thr Gly His
    210                 215                 220
```

```
Ser Leu Gly Ala Ala Ile Ala Thr Leu Asn Ala Val Asp Ile Val Thr
225                 230                 235                 240

Asn Gly Tyr Asn Lys Pro Ser Asp Pro Ser Leu Lys Ala Ser Pro Val
            245                 250                 255

Thr Ala Ile Val Phe Ala Ser Pro Arg Val Gly Asp Ile Asn Phe Gln
        260                 265                 270

Lys Val Phe Ser Gly Tyr Lys Asp Leu Thr Thr Ile Arg Ile Arg Asn
    275                 280                 285

Glu Leu Asp Ile Val Pro Asn Tyr Pro Leu Val Gly Tyr Ser Asp Val
290                 295                 300

Gly Glu Glu Leu Lys Ile Asp Thr Arg Lys Ser Met Tyr Leu Lys Ser
305                 310                 315                 320

Pro Gly Asn Pro Ser Ser Trp His Asn Leu Glu Ala Tyr Leu His Gly
                325                 330                 335

Val Ala Gly Thr Gln Arg Ser Lys Gly Gly Phe Lys Leu Glu Val His
            340                 345                 350

Arg Asp Ile Ala Leu Val Asn Lys Thr Leu Asp Ala Leu Lys Asp Glu
        355                 360                 365

Phe Leu Val Pro Val Ser Trp Arg Thr Glu Lys Asn Lys Gly Met Val
    370                 375                 380

Gln Gln Asn Asp Gly Ser Trp Lys Leu Met Asp His Glu Asp Asp Asp
385                 390                 395                 400

Phe
```

<210> SEQ ID NO 93
<211> LENGTH: 978
<212> TYPE: DNA
<213> ORGANISM: Oryza sativa

<400> SEQUENCE: 93

```
atgccgatgc cgttatatgg ggtggtcaac tcgccgtgcc gcagccactg cagggccgcg    60
gcaacgttgt tggtctcggt gtccctgctc tgctcttgct tcgccatcgc catgccgagc   120
gtcgtcgtca cggtcgacca gtccggcaag ggcgaccacc ggaggatcca ggacgcgatc   180
gatgccgccc cggcaaacga ctcctcccgc accgtcatcc ggatcaagcc cggggtttac   240
agggagaagg tcgtggtgga caagccgtac gtgacgctga ccggcacgag cgcgacctcg   300
acggtgatcg cctggaacga gtcgtgggtc tccgacgagt cccccaccgt gtccgtgctg   360
gcctccgact cgtcgccaa gcgcctgacg tttcagaaca cgttcgggga cagcgcgccg   420
gcggtggcgt gagggtcgc cggagacagg gcggcgttct acgggtgcag gttcgtgtcg   480
ttccaggaca cgctcctcga cgagacgggg cggcactact accgcggctg ctacgtgcag   540
ggcgccaccg acttcatatt cggaaacggc cgggctctgt tgacaaatg ccacctgcac   600
tccacgtcgc ccgacggcgc cggcggggcg ttcacggcgc agcagcggtc gtcggaatcg   660
gaggagacgg ggtacagctt cgtgggtgc aagctgaccg gctcggcgc cggcaccctcc   720
atcctgggcc ggccgtgggg gccatactcc cgcgtcgtct tcgcgctcac ctacatgtcc   780
tccaccgtca ggccccaagg ctgggacgac tggggcgacc cctccaatca gcggacggcg   840
ttctatgggc agtaccagtg ctacggcgac ggatcgaaga ccgacggcag ggttgcctgg   900
tctcacgacc tgacgcaggc cgaggcggcg ccgttcatca ccaaggcttg ggttgatggg   960
cagcaatggc ttcggtag                                                978
```

<210> SEQ ID NO 94

```
<211> LENGTH: 325
<212> TYPE: PRT
<213> ORGANISM: Oryza sativa

<400> SEQUENCE: 94

Met Pro Met Pro Leu Tyr Gly Val Val Asn Ser Pro Cys Arg Ser His
1               5                   10                  15

Cys Arg Ala Ala Ala Thr Leu Leu Val Ser Val Ser Leu Leu Cys Ser
            20                  25                  30

Cys Phe Ala Ile Ala Met Pro Ser Val Val Thr Val Asp Gln Ser
        35                  40                  45

Gly Lys Gly Asp His Arg Arg Ile Gln Asp Ala Ile Asp Ala Ala Pro
    50                  55                  60

Ala Asn Asp Ser Ser Arg Thr Val Ile Arg Ile Lys Pro Gly Val Tyr
65                  70                  75                  80

Arg Glu Lys Val Val Val Asp Lys Pro Tyr Val Thr Leu Thr Gly Thr
                85                  90                  95

Ser Ala Thr Ser Thr Val Ile Ala Trp Asn Glu Ser Trp Val Ser Asp
            100                 105                 110

Glu Ser Pro Thr Val Ser Val Leu Ala Ser Asp Phe Val Ala Lys Arg
        115                 120                 125

Leu Thr Phe Gln Asn Thr Phe Gly Asp Ser Ala Pro Ala Val Ala Val
    130                 135                 140

Arg Val Ala Gly Asp Arg Ala Ala Phe Tyr Gly Cys Arg Phe Val Ser
145                 150                 155                 160

Phe Gln Asp Thr Leu Leu Asp Glu Thr Gly Arg His Tyr Tyr Arg Gly
                165                 170                 175

Cys Tyr Val Gln Gly Ala Thr Asp Phe Ile Phe Gly Asn Gly Arg Ala
            180                 185                 190

Leu Phe Asp Lys Cys His Leu His Ser Thr Ser Pro Asp Gly Ala Gly
        195                 200                 205

Gly Ala Phe Thr Ala Gln Gln Arg Ser Ser Glu Ser Glu Glu Thr Gly
    210                 215                 220

Tyr Ser Phe Val Gly Cys Lys Leu Thr Gly Leu Gly Ala Gly Thr Ser
225                 230                 235                 240

Ile Leu Gly Arg Pro Trp Gly Pro Tyr Ser Arg Val Val Phe Ala Leu
                245                 250                 255

Thr Tyr Met Ser Ser Thr Val Arg Pro Gln Gly Trp Asp Asp Trp Gly
            260                 265                 270

Asp Pro Ser Asn Gln Arg Thr Ala Phe Tyr Gly Gln Tyr Gln Cys Tyr
        275                 280                 285

Gly Asp Gly Ser Lys Thr Asp Gly Arg Val Ala Trp Ser His Asp Leu
    290                 295                 300

Thr Gln Ala Glu Ala Ala Pro Phe Ile Thr Lys Ala Trp Val Asp Gly
305                 310                 315                 320

Gln Gln Trp Leu Arg
                325

<210> SEQ ID NO 95
<211> LENGTH: 786
<212> TYPE: DNA
<213> ORGANISM: Zea mays

<400> SEQUENCE: 95
atgcatcgtg caccaagtga gaaggtgatc gtaccgcaga acaagagctt catcctgctg     60
```

-continued

```
gaaggcgagg ggtggcagca gacgtcgatc gagtgggcgg accacgccgg cggggactcg      120
acaaccgccg cctccccgac gttcgccgcg tactcggacg acttcatggc ccgagacatc      180
accttcaaga acacgtacaa cggggacggg aggatcgcgc cggcggtggc ggcgctggcg      240
gcgggagatc ggtcgtcctt ctaccggtgc ggcttcgtga gcgtccagga cacgctgagc      300
gacctcgagg ggaggcacta ctacgagggc tgctacatcg agggcgccat ggacttcatc      360
ttcggcaacg gtcagtccat cttccagggc tgcgagatat ggacggcccg gacgccggtg      420
tggcccggct tcatcacggc gcaggggcgg atgagcgagg cggactccag cgggttcgtc      480
ttcaagggat gcacggtgag gggggtgacg ccggcgtacc tgggccgcgc gtggcgccgc      540
tacgccaggg tcatcttctt ccagacggac atgtccggcg tcgtcgttag ccaggggtgg      600
gacgcgtgga gctacaaggg cacagagggc acgctgacca tggtggaaga agggtgcacg      660
gggcaggggt ccaaccggac gggccgggtg ccatggacca aggacctcag cggcgacgac      720
ctcgccaagt tcgtcgacct ctcctacgtc tctgccgacg gctggctcga cgcacagcca      780
cgctag                                                                 786
```

<210> SEQ ID NO 96
<211> LENGTH: 261
<212> TYPE: PRT
<213> ORGANISM: Zea mays

<400> SEQUENCE: 96

```
Met His Arg Ala Pro Ser Glu Lys Val Ile Val Pro Gln Asn Lys Ser
1               5                   10                  15

Phe Ile Leu Leu Glu Gly Glu Gly Trp Gln Gln Thr Ser Ile Glu Trp
            20                  25                  30

Ala Asp His Ala Gly Gly Asp Ser Thr Thr Ala Ser Pro Thr Phe
        35                  40                  45

Ala Ala Tyr Ser Asp Asp Phe Met Ala Arg Asp Ile Thr Phe Lys Asn
    50                  55                  60

Thr Tyr Asn Gly Asp Gly Arg Ile Ala Pro Ala Val Ala Ala Leu Ala
65                  70                  75                  80

Ala Gly Asp Arg Ser Ser Phe Tyr Arg Cys Gly Phe Val Ser Val Gln
                85                  90                  95

Asp Thr Leu Ser Asp Leu Glu Gly Arg His Tyr Tyr Glu Gly Cys Tyr
            100                 105                 110

Ile Glu Gly Ala Met Asp Phe Ile Phe Gly Asn Gly Gln Ser Ile Phe
        115                 120                 125

Gln Gly Cys Glu Ile Trp Thr Ala Arg Thr Pro Val Trp Pro Gly Phe
    130                 135                 140

Ile Thr Ala Gln Gly Arg Met Ser Glu Ala Asp Ser Ser Gly Phe Val
145                 150                 155                 160

Phe Lys Gly Cys Thr Val Arg Gly Val Thr Pro Ala Tyr Leu Gly Arg
                165                 170                 175

Ala Trp Arg Arg Tyr Ala Arg Val Ile Phe Phe Gln Thr Asp Met Ser
            180                 185                 190

Gly Val Val Val Ser Gln Gly Trp Asp Ala Trp Ser Tyr Lys Gly Thr
        195                 200                 205

Glu Gly Thr Leu Thr Met Val Glu Glu Gly Cys Thr Gly Gln Gly Ser
    210                 215                 220

Asn Arg Thr Gly Arg Val Pro Trp Thr Lys Asp Leu Ser Gly Asp Asp
225                 230                 235                 240
```

```
Leu Ala Lys Phe Val Asp Leu Ser Tyr Val Ser Ala Asp Gly Trp Leu
                245                 250                 255
Asp Ala Gln Pro Arg
            260
```

<210> SEQ ID NO 97
<211> LENGTH: 1017
<212> TYPE: DNA
<213> ORGANISM: Sorghum bicolor

<400> SEQUENCE: 97

```
atgacgaggc tccggctagg acctccgttg ttcaaaatgg ccctagccgt cttagccgcc      60
gtgctcgctt ccatggcgcc ccgaggtcgc tgcgacgacg cggcgaggtc cgtggtggcc     120
agaagcatct tcgtcaaccg gaagggcggc gccgacttca cgtcggtcca ggacgccgtc     180
gactctgttc cgctcggcaa cgaccagtgg atccgagttc acgtcgccgc cggcgtgtac     240
aatgagaagg tgatgatacc gcagaacaag agcttcatcc tgctggaagg cgaggggtgg     300
cagcagacgt cgatcgagtg gcggaccac gccggcgggg actcgagcac cgccgccacc     360
ccaacgttcg cggcgtactc agccgacttc atggcccgcg acatcgcctt caagaacacg     420
tacaacggtg ccggcgggac gacgacgatc gcgccggcgg tggcggcgct ggtggcgggc     480
gaccggtcgt ccttctaccg gtgcggcttc gtgagcgtgc aggacacgct gagcgacatc     540
caagggaggc actactacga gggctgccac atccagggcg ccatggactt catcttcggc     600
aacggccagt ccatcttcca ggggtgcgag atatggacgg cgcggacgcc cgtgtggcca     660
ggcttcatca cggcgcaggg gagggtgagc gaggcggaca cgagcggctt cgtcttcaag     720
ggctgcacgg tgagggcgt cacgccggcg tacctgggac gcgcgtggcg acgctacgcc     780
agggtcatct ctaccagac ggacatgtcc ggcgtcgtca gccaggggtg ggacgcgtgg     840
ggctacaagg gcacagaggg cacgctgact atggtggagg aagggtgcac ggggcagggg     900
tccaacagga cgggccgggt gccatggact aaggacctga gcgcgccga actcgccaag     960
ttcgtcgacc tctcctacgt ctctgccgac ggctggctcg acgcgcagcc acgctag     1017
```

<210> SEQ ID NO 98
<211> LENGTH: 338
<212> TYPE: PRT
<213> ORGANISM: Sorghum bicolor

<400> SEQUENCE: 98

```
Met Thr Arg Leu Arg Leu Gly Pro Pro Leu Phe Lys Met Ala Leu Ala
1               5                   10                  15
Val Leu Ala Ala Val Leu Ala Ser Met Ala Pro Arg Gly Arg Cys Asp
            20                  25                  30
Asp Ala Ala Arg Ser Val Val Ala Arg Ser Ile Phe Val Asn Arg Lys
        35                  40                  45
Gly Gly Ala Asp Phe Thr Ser Val Gln Asp Ala Val Asp Ser Val Pro
    50                  55                  60
Leu Gly Asn Asp Gln Trp Ile Arg Val His Val Ala Ala Gly Val Tyr
65                  70                  75                  80
Asn Glu Lys Val Met Ile Pro Gln Asn Lys Ser Phe Ile Leu Leu Glu
                85                  90                  95
Gly Glu Gly Trp Gln Gln Thr Ser Ile Glu Trp Ala Asp His Ala Gly
            100                 105                 110
Gly Asp Ser Ser Thr Ala Ala Thr Pro Thr Phe Ala Ala Tyr Ser Ala
        115                 120                 125
```

```
Asp Phe Met Ala Arg Asp Ile Ala Phe Lys Asn Thr Tyr Asn Gly Ala
    130                 135                 140
Gly Gly Thr Thr Thr Ile Ala Pro Ala Val Ala Leu Val Ala Gly
145                 150                 155                 160
Asp Arg Ser Ser Phe Tyr Arg Cys Gly Phe Val Ser Val Gln Asp Thr
                165                 170                 175
Leu Ser Asp Ile Gln Gly Arg His Tyr Tyr Glu Gly Cys His Ile Gln
            180                 185                 190
Gly Ala Met Asp Phe Ile Phe Gly Asn Gly Gln Ser Ile Phe Gln Gly
        195                 200                 205
Cys Glu Ile Trp Thr Ala Arg Thr Pro Val Trp Pro Gly Phe Ile Thr
    210                 215                 220
Ala Gln Gly Arg Val Ser Glu Ala Asp Thr Ser Gly Phe Val Phe Lys
225                 230                 235                 240
Gly Cys Thr Val Arg Gly Val Thr Pro Ala Tyr Leu Gly Arg Ala Trp
                245                 250                 255
Arg Arg Tyr Ala Arg Val Ile Phe Tyr Gln Thr Asp Met Ser Gly Val
            260                 265                 270
Val Ser Gln Gly Trp Asp Ala Trp Gly Tyr Lys Gly Thr Glu Gly Thr
        275                 280                 285
Leu Thr Met Val Glu Glu Gly Cys Thr Gly Gln Gly Ser Asn Arg Thr
    290                 295                 300
Gly Arg Val Pro Trp Thr Lys Asp Leu Ser Gly Ala Glu Leu Ala Lys
305                 310                 315                 320
Phe Val Asp Leu Ser Tyr Val Ser Ala Asp Gly Trp Leu Asp Ala Gln
                325                 330                 335
Pro Arg
```

<210> SEQ ID NO 99
<211> LENGTH: 993
<212> TYPE: DNA
<213> ORGANISM: Arabidopsis thaliana

<400> SEQUENCE: 99

```
atgggaactc atcgaattat ccttggtctc gccgctcttt gttgttttg tctacctcat      60
ctcattgaag ctaaaccatt cgaagtgatc gtcgatcaat cgggccatgg aaatttcacg    120
accatacaaa aagctattga ttcggtccca atcaacaata ctcattggtt cttcatcaac    180
gttaaagccg gcctttacag agagaaaata acgataccgc aaaaaaaacc tttcatagta    240
atcgtgggag ctgggaaacg gtcaacgaga gtagaatggg acgaccatgc ctcgcttgca    300
caaagcccta cctttgctac tctagctgat aacaccgtcg ttaaaaagat cactttcgcc    360
aattcctaca acttccctag caatgggaaa ataaacaaga ccctagagt tccggccgtg    420
gcagcattta tcggcggtga taagtcggct ttttactcgg taggatttgc tggaattcaa    480
gataccttgt gggactcgga tggccgacac tacttccata tgatgcacca tccaaggcgcg    540
gttgatttca tcttagggag cggccaatct atttaccaga gctgtgtgat acaagtgcta    600
ggtgggcagc taggaccggg ggtaacgggt tacataacgg ctcaaggacg gaccaacgca    660
aacgacgcga atggattcgt attcatcaac tgcctcgttc atggattcgg caaggcttac    720
ttgggcagag cctggcgccc atactctcga gtgatatttt acaactcgaa cctgacggat    780
gtggttgatc tctaggatg gtgggaatgg aactaccagg gttacgaaaa gcagctgacc    840
tatgcagaac atggatgctt cggaagtgga tcaaatacat caagacgtgc caaatgggtt    900
```

```
aagaagctga gtgcatctgc cgtccaacat ttggctgatc tcagcttcat taatcgtggt    960
ggatgggttg aagatttacc catccgtgtt tga                                 993
```

<210> SEQ ID NO 100
<211> LENGTH: 330
<212> TYPE: PRT
<213> ORGANISM: Arabidopsis thaliana

<400> SEQUENCE: 100

| | | | | | | | | | | | | | | |
|---|---|---|---|---|---|---|---|---|---|---|---|---|---|---|
| Met | Gly | Thr | His | Arg | Ile | Ile | Leu | Gly | Leu | Ala | Ala | Leu | Cys | Cys | Phe |
| 1 | | | | 5 | | | | | 10 | | | | | 15 | |
| Cys | Leu | Pro | His | Leu | Ile | Glu | Ala | Lys | Pro | Phe | Glu | Val | Ile | Val | Asp |
| | | | 20 | | | | | 25 | | | | | 30 | | |
| Gln | Ser | Gly | His | Gly | Asn | Phe | Thr | Thr | Ile | Gln | Lys | Ala | Ile | Asp | Ser |
| | | 35 | | | | | 40 | | | | | 45 | | | |
| Val | Pro | Ile | Asn | Asn | Thr | His | Trp | Phe | Phe | Ile | Asn | Val | Lys | Ala | Gly |
| 50 | | | | | 55 | | | | | 60 | | | | | |
| Leu | Tyr | Arg | Glu | Lys | Ile | Thr | Ile | Pro | Gln | Lys | Lys | Pro | Phe | Ile | Val |
| 65 | | | | | 70 | | | | | 75 | | | | | 80 |
| Ile | Val | Gly | Ala | Gly | Lys | Arg | Ser | Thr | Arg | Val | Glu | Trp | Asp | Asp | His |
| | | | | 85 | | | | | 90 | | | | | 95 | |
| Ala | Ser | Leu | Ala | Gln | Ser | Pro | Thr | Phe | Ala | Thr | Leu | Ala | Asp | Asn | Thr |
| | | | 100 | | | | | 105 | | | | | 110 | | |
| Val | Val | Lys | Lys | Ile | Thr | Phe | Ala | Asn | Ser | Tyr | Asn | Phe | Pro | Ser | Asn |
| | | 115 | | | | | 120 | | | | | 125 | | | |
| Gly | Lys | Ile | Asn | Lys | Asn | Pro | Arg | Val | Pro | Ala | Val | Ala | Ala | Phe | Ile |
| | 130 | | | | | 135 | | | | | 140 | | | | |
| Gly | Gly | Asp | Lys | Ser | Ala | Phe | Tyr | Ser | Val | Gly | Phe | Ala | Gly | Ile | Gln |
| 145 | | | | | 150 | | | | | 155 | | | | | 160 |
| Asp | Thr | Leu | Trp | Asp | Ser | Asp | Gly | Arg | His | Tyr | Phe | His | Arg | Cys | Thr |
| | | | | 165 | | | | | 170 | | | | | 175 | |
| Ile | Gln | Gly | Ala | Val | Asp | Phe | Ile | Leu | Gly | Ser | Gly | Gln | Ser | Ile | Tyr |
| | | | 180 | | | | | 185 | | | | | 190 | | |
| Gln | Ser | Cys | Val | Ile | Gln | Val | Leu | Gly | Gly | Gln | Leu | Gly | Pro | Gly | Val |
| | | 195 | | | | | 200 | | | | | 205 | | | |
| Thr | Gly | Tyr | Ile | Thr | Ala | Gln | Gly | Arg | Thr | Asn | Ala | Asn | Asp | Ala | Asn |
| | 210 | | | | | 215 | | | | | 220 | | | | |
| Gly | Phe | Val | Phe | Ile | Asn | Cys | Leu | Val | His | Gly | Phe | Gly | Lys | Ala | Tyr |
| 225 | | | | | 230 | | | | | 235 | | | | | 240 |
| Leu | Gly | Arg | Ala | Trp | Arg | Pro | Tyr | Ser | Arg | Val | Ile | Phe | Tyr | Asn | Ser |
| | | | | 245 | | | | | 250 | | | | | 255 | |
| Asn | Leu | Thr | Asp | Val | Val | Asp | Pro | Leu | Gly | Trp | Trp | Glu | Trp | Asn | Tyr |
| | | | 260 | | | | | 265 | | | | | 270 | | |
| Gln | Gly | Tyr | Glu | Lys | Gln | Leu | Thr | Tyr | Ala | Glu | His | Gly | Cys | Phe | Gly |
| | | 275 | | | | | 280 | | | | | 285 | | | |
| Ser | Gly | Ser | Asn | Thr | Ser | Arg | Arg | Ala | Lys | Trp | Val | Lys | Lys | Leu | Ser |
| | 290 | | | | | 295 | | | | | 300 | | | | |
| Ala | Ser | Ala | Val | Gln | His | Leu | Ala | Asp | Leu | Ser | Phe | Ile | Asn | Arg | Gly |
| 305 | | | | | 310 | | | | | 315 | | | | | 320 |
| Gly | Trp | Val | Glu | Asp | Leu | Pro | Ile | Arg | Val | | | | | | |
| | | | | 325 | | | | | 330 | | | | | | |

<210> SEQ ID NO 101
<211> LENGTH: 960

```
<212> TYPE: DNA
<213> ORGANISM: Glycine max

<400> SEQUENCE: 101
atgtcaatca ccgccatcat tttgttcggc atcaccacca ccaccatgat tacaacaaac      60
aaactactaa gaaaacagtc cattattctt ccaggacaat tattgtggac cgattgggga     120
atggacactt ctctacgata caatctgcca ttgattcagt cgcttcctac aacaagaatt     180
ggggaaaagg tgaagatcac ttctgacaag cctttcatcg tactaaaagg agagggacaa     240
aagaacactt tgttgagtg gcatgaccat gattcaagtg cagagagtcc tacgttcaca      300
accatggccg acaatgtcgt cgtcaagtcc attagcttta ggaatacata caataataac     360
agaaatgcta actcaatgga agctgcggta gctgcaatga tatttggcga caggtcgtac     420
ttctatgacg ttggcttctt tggtttgcaa gacactttgt gggatggaca aggaagacat     480
tacttcaagt cttgtacaat tcaaggtgct atggatttta tcttcggcac tggccaatct     540
ttatatgagg actgtaccat atccgctatt ggtgctaatc ttggtcctgg cattattggt     600
tttatcacgg cacaagggag aacaaatcca acgatgcaa atgggtttgt ttttaagcat      660
tgcaatatcg ttggaaatgg tacaacttac ttgggaagac catggagagg ttatgctaga     720
gttcttttct atgatactaa aatctctaac attatccaac cattaggttg gcagccatgg     780
gatttcgctg gcacgagga tcacataaca ttcgcagagt atggcaattc tggacctggt      840
tctgacactt ccaagcgagt aagttggtta agaaaattgg attcatcaac agttagcaag     900
ttggcaacta ctagcttcat tgacaccgaa ggttggctaa atacactgac gcagctctaa     960

<210> SEQ ID NO 102
<211> LENGTH: 319
<212> TYPE: PRT
<213> ORGANISM: Glycine max

<400> SEQUENCE: 102

Met Ser Ile Thr Ala Ile Ile Leu Phe Gly Ile Thr Thr Thr Thr Met
1               5                   10                  15

Ile Thr Thr Asn Lys Leu Leu Arg Lys Gln Ser Ile Ile Leu Pro Gly
            20                  25                  30

Gln Leu Leu Trp Thr Asp Trp Gly Met Asp Thr Ser Leu Arg Tyr Asn
        35                  40                  45

Leu Pro Leu Ile Gln Ser Leu Pro Thr Thr Arg Ile Gly Glu Lys Val
    50                  55                  60

Lys Ile Thr Ser Asp Lys Pro Phe Ile Val Leu Lys Gly Glu Gly Gln
65                  70                  75                  80

Lys Asn Thr Phe Val Glu Trp His Asp His Asp Ser Ser Ala Glu Ser
                85                  90                  95

Pro Thr Phe Thr Thr Met Ala Asp Asn Val Val Lys Ser Ile Ser
            100                 105                 110

Phe Arg Asn Thr Tyr Asn Asn Asn Arg Asn Ala Asn Ser Met Glu Ala
        115                 120                 125

Ala Val Ala Ala Met Ile Phe Gly Asp Arg Ser Tyr Phe Tyr Asp Val
    130                 135                 140

Gly Phe Phe Gly Leu Gln Asp Thr Leu Trp Asp Gly Gln Gly Arg His
145                 150                 155                 160

Tyr Phe Lys Ser Cys Thr Ile Gln Gly Ala Met Asp Phe Ile Phe Gly
                165                 170                 175

Thr Gly Gln Ser Leu Tyr Glu Asp Cys Thr Ile Ser Ala Ile Gly Ala
```

```
            180                 185                 190
Asn Leu Gly Pro Gly Ile Ile Gly Phe Ile Thr Ala Gln Gly Arg Thr
            195                 200                 205

Asn Pro Asn Asp Ala Asn Gly Phe Val Phe Lys His Cys Asn Ile Val
        210                 215                 220

Gly Asn Gly Thr Thr Tyr Leu Gly Arg Pro Trp Gly Tyr Ala Arg
225                 230                 235                 240

Val Leu Phe Tyr Asp Thr Lys Ile Ser Asn Ile Ile Gln Pro Leu Gly
                245                 250                 255

Trp Gln Pro Trp Asp Phe Ala Gly His Glu Asp His Ile Thr Phe Ala
                260                 265                 270

Glu Tyr Gly Asn Ser Gly Pro Gly Ser Asp Thr Ser Lys Arg Val Ser
            275                 280                 285

Trp Leu Lys Lys Leu Asp Ser Ser Thr Val Ser Lys Leu Ala Thr Thr
        290                 295                 300

Ser Phe Ile Asp Thr Glu Gly Trp Leu Asn Thr Leu Thr Gln Leu
305                 310                 315
```

<210> SEQ ID NO 103
<211> LENGTH: 405
<212> TYPE: DNA
<213> ORGANISM: Oryza sativa

<400> SEQUENCE: 103

```
atgttaatga atctagatag atgtgaaacg gagggagtac atagcatcat ctcgacggtc    60
tgcgagcttg agcttgagat gtggtgtttc cccatctcat gtgaatcatt tgagccttcc   120
ggatcccaac tcctgaacca tccaaggcgt atccgtctcc atcatcaggc gttgctgttg   180
tttagacaag ctgatctacc gtctctcctt tcaagttaca tagttcaagt cgtcattcat   240
tacttcgaca acagtctgc cgagttcatc aactcagctg ctggggccat caccgtctcc   300
tacatcatgc agctactgac tggactactt gggagggagt tttcagcagt aatatatgca   360
acacaaagta tatctaatat actttccatc agtggggaag agtag                  405
```

<210> SEQ ID NO 104
<211> LENGTH: 134
<212> TYPE: PRT
<213> ORGANISM: Oryza sativa

<400> SEQUENCE: 104

```
Met Leu Met Asn Leu Asp Arg Cys Glu Thr Glu Gly Val His Ser Ile
1               5                   10                  15

Ile Ser Thr Val Cys Glu Leu Glu Leu Glu Met Trp Cys Phe Pro Ile
            20                  25                  30

Ser Cys Glu Ser Phe Glu Pro Ser Gly Ser Gln Leu Leu Asn His Pro
        35                  40                  45

Arg Arg Ile Arg Leu His His Gln Ala Leu Leu Leu Phe Arg Gln Ala
    50                  55                  60

Asp Leu Pro Ser Leu Leu Ser Ser Tyr Ile Val Gln Val Val Ile His
65                  70                  75                  80

Tyr Phe Asp Lys Gln Ser Ala Glu Phe Ile Asn Ser Ala Ala Gly Ala
                85                  90                  95

Ile Thr Val Ser Tyr Ile Met Gln Leu Leu Thr Gly Leu Leu Gly Arg
            100                 105                 110

Glu Phe Ser Ala Val Ile Tyr Ala Thr Gln Ser Ile Ser Asn Ile Leu
        115                 120                 125
```

```
Ser Ile Ser Gly Glu Glu
    130

<210> SEQ ID NO 105
<211> LENGTH: 2289
<212> TYPE: DNA
<213> ORGANISM: Oryza sativa

<400> SEQUENCE: 105
atgtggaggc tgaaggtggc ccagggcggc ggcgctttgt tgcggtcgac gaacggcttc      60
gccgggcgag cggtgtggga gttcgacccc gaccacggca cgccggagga ccgagccaac     120
gtcgagaggg tgcgccgcga cttcaccgac caccgcctcc gccgcccgga gtccgccgat     180
ctcctcatgc gcatgcagtt tgcaagagaa acaatcacc  aacgccgtgg tgatcgtatt     240
ccaccggccg tcaataagct tggcgagaag gagcaggtga ctgaagaaac tgtgatggct     300
tccttgaggc gagctctcga tgagttctcc tctctgcaag cagatgatgg ccactggcct     360
ggcgacctca gtggtgctat attcatcatg cctgtcttga tattttcttt gtatgccact     420
ggatcactgg acactgtcat atcatcagaa caccggaggg agatatgtcg ctacatctat     480
aaccatcaga acgaggacgg gggatggggc atgctaatct gggatcaag  cacgatgttt     540 gccacatgct taaactatgt caccctgaga cttatcggcg aggagccaag caatgagcaa     600
ttagctagag acacgcctg  gatcatatca catggtggcg ccacccttgt tccgcaatgg     660
ggaaagatat gtctgtcgat aattggagtg tatgagtggt caggaaacaa ccccatcttc     720
cccgagttat ggcttgctcc acaattcctt ccgtttcatc caggcaaatt ctggggcccg     780
acccgcgtgg tgtacgtgcc gatggcctat ctgtacggca agaagttcgt ggggcccatc     840
acgccaacca tactggcgct cgagaggag  atatacacgg accccatacca caccattgac     900 tgggcccaag cctgcaacgc atgctccaag gaggatttgg tctgcccgcg cacgctgctg     960
cagaatgtgg tgtggacttc gctctacaag tgggtggagc cggtgctagg cagcaggccg    1020
atgaacaagc tgagggagag agctttggat agactcatgg agcatatcca ttacgaagat    1080
gaaaactcac agtacctctg cctatgtcct gtcaacaagg ctcttaacat ggtctgctgc    1140
tgggtggaag atccaaattc agattcattc aagcggcatc ttgcaaggat acctgatttc    1200
ctgtggcttt cagaagatgg catgaaggca cagatatatg atggttgcca gagctgggaa    1260
acagcattta taattcaagc gttttgtgct actgatcttg taaatgagta tggttcaact    1320
gttaggagag cccacgagtt catgaaaaat tcacagatta tgaggaatca tcctggtgac    1380
caaagttact ggcatcgcca tagatcaaag ggttcatgga ctctttcgtc agcagacaat    1440
ggatgggctg tgtctgacac tacagcagaa gcgctgaagg ctgtactgtt actggaaaag    1500
atctctagca acgtggtcgg ggatccaatt gaaatagaaa ggctgcatga tgctgttgat    1560
tgcctcctat ctttcgtgaa caaagatggt acccttccta catatgaatg taaaagaact    1620
tatacttgga tagaggttct cagtccttgt gagagttttc caaacatagt ggttgattat    1680
ccatttccag aatgcaccct ctctgtgctt caagctctgg tgctgttcaa caactacac     1740 cctagttacc gtattaaaga gatagaaaaa tgtgtcagaa acgcagcgat gtttattgag    1800
agcacacaag gcgaagatgg ttcatggcta ggcacttggg gtgtgtgttt cacctatggg    1860
gcctttcttt cagtaaaagg gttaattgct gctggaagaa catatgagaa tagttcttcc    1920
atcaggaaag catgcgactt tatattatca aagcagctcg atactggtgg gtggggagaa    1980
agttatgtct ctaatattac taaggtttac gtaaacatta aagatgatca agctcatgca    2040
```

```
gtgaatactg cctgggcaat gttagcttta atttgtgcag gacagatgga gcgggatcca   2100
gcaccactgc atcgtgctgc aaaagaatta atcaatatgc agttggaaac aggagagttc   2160
ccccaacaag aacatgttgg agccttcaat gcatgcctct tctttaatta ccccaactac   2220
cgcaacttat tccctatctg ggctcttgga gagtactgtc gtcatcttca ctccacgagg   2280
cgtgcatga                                                            2289

<210> SEQ ID NO 106
<211> LENGTH: 762
<212> TYPE: PRT
<213> ORGANISM: Oryza sativa

<400> SEQUENCE: 106

Met Trp Arg Leu Lys Val Ala Gln Gly Gly Ala Leu Leu Arg Ser
1               5                   10                  15

Thr Asn Gly Phe Ala Gly Arg Ala Val Trp Glu Phe Asp Pro Asp His
            20                  25                  30

Gly Thr Pro Glu Asp Arg Ala Asn Val Glu Arg Val Arg Arg Asp Phe
        35                  40                  45

Thr Asp His Arg Leu Arg Arg Pro Glu Ser Ala Asp Leu Leu Met Arg
    50                  55                  60

Met Gln Phe Ala Arg Glu Asn Asn His Gln Arg Arg Gly Asp Arg Ile
65                  70                  75                  80

Pro Pro Ala Val Asn Lys Leu Gly Glu Lys Glu Gln Val Thr Glu Glu
                85                  90                  95

Thr Val Met Ala Ser Leu Arg Arg Ala Leu Asp Glu Phe Ser Ser Leu
            100                 105                 110

Gln Ala Asp Asp Gly His Trp Pro Gly Asp Leu Ser Gly Ala Ile Phe
        115                 120                 125

Ile Met Pro Val Leu Ile Phe Ser Leu Tyr Ala Thr Gly Ser Leu Asp
    130                 135                 140

Thr Val Ile Ser Ser Glu His Arg Arg Glu Ile Cys Arg Tyr Ile Tyr
145                 150                 155                 160

Asn His Gln Asn Glu Asp Gly Gly Trp Gly Met Leu Ile Leu Gly Ser
                165                 170                 175

Ser Thr Met Phe Ala Thr Cys Leu Asn Tyr Val Thr Leu Arg Leu Ile
            180                 185                 190

Gly Glu Glu Pro Ser Asn Glu Gln Leu Ala Arg Gly His Ala Trp Ile
        195                 200                 205

Ile Ser His Gly Gly Ala Thr Leu Val Pro Gln Trp Gly Lys Ile Cys
    210                 215                 220

Leu Ser Ile Ile Gly Val Tyr Glu Trp Ser Gly Asn Asn Pro Ile Phe
225                 230                 235                 240

Pro Glu Leu Trp Leu Ala Pro Gln Phe Leu Pro Phe His Pro Gly Lys
                245                 250                 255

Phe Trp Gly Pro Thr Arg Val Val Tyr Val Pro Met Ala Tyr Leu Tyr
            260                 265                 270

Gly Lys Lys Phe Val Gly Pro Ile Thr Pro Thr Ile Leu Ala Leu Arg
        275                 280                 285

Glu Glu Ile Tyr Thr Asp Pro Tyr His Thr Ile Asp Trp Ala Gln Ala
    290                 295                 300

Cys Asn Ala Cys Ser Lys Glu Asp Leu Val Cys Pro Arg Thr Leu Leu
305                 310                 315                 320
```

```
Gln Asn Val Val Trp Thr Ser Leu Tyr Lys Trp Val Glu Pro Val Leu
            325                 330                 335

Gly Ser Arg Pro Met Asn Lys Leu Arg Glu Arg Ala Leu Asp Arg Leu
            340                 345                 350

Met Glu His Ile His Tyr Glu Asp Glu Asn Ser Gln Tyr Leu Cys Leu
            355                 360                 365

Cys Pro Val Asn Lys Ala Leu Asn Met Val Cys Cys Trp Val Glu Asp
            370                 375                 380

Pro Asn Ser Asp Ser Phe Lys Arg His Leu Ala Arg Ile Pro Asp Phe
385                 390                 395                 400

Leu Trp Leu Ser Glu Asp Gly Met Lys Ala Gln Ile Tyr Asp Gly Cys
            405                 410                 415

Gln Ser Trp Glu Thr Ala Phe Ile Ile Gln Ala Phe Cys Ala Thr Asp
            420                 425                 430

Leu Val Asn Glu Tyr Gly Ser Thr Val Arg Arg Ala His Glu Phe Met
            435                 440                 445

Lys Asn Ser Gln Ile Met Arg Asn His Pro Gly Asp Gln Ser Tyr Trp
            450                 455                 460

His Arg His Arg Ser Lys Gly Ser Trp Thr Leu Ser Ser Ala Asp Asn
465                 470                 475                 480

Gly Trp Ala Val Ser Asp Thr Thr Ala Glu Ala Leu Lys Ala Val Leu
            485                 490                 495

Leu Leu Glu Lys Ile Ser Ser Asn Val Val Gly Asp Pro Ile Glu Ile
            500                 505                 510

Glu Arg Leu His Asp Ala Val Asp Cys Leu Leu Ser Phe Val Asn Lys
            515                 520                 525

Asp Gly Thr Leu Ser Thr Tyr Glu Cys Lys Arg Thr Tyr Thr Trp Ile
530                 535                 540

Glu Val Leu Ser Pro Cys Glu Ser Phe Pro Asn Ile Val Val Asp Tyr
545                 550                 555                 560

Pro Phe Pro Glu Cys Thr Ser Ser Val Leu Gln Ala Leu Val Leu Phe
            565                 570                 575

Lys Gln Leu His Pro Ser Tyr Arg Ile Lys Glu Ile Glu Lys Cys Val
            580                 585                 590

Arg Asn Ala Ala Met Phe Ile Glu Ser Thr Gln Gly Glu Asp Gly Ser
            595                 600                 605

Trp Leu Gly Thr Trp Gly Val Cys Phe Thr Tyr Gly Ala Phe Leu Ser
            610                 615                 620

Val Lys Gly Leu Ile Ala Ala Gly Arg Thr Tyr Glu Asn Ser Ser Ser
625                 630                 635                 640

Ile Arg Lys Ala Cys Asp Phe Ile Leu Ser Lys Gln Leu Asp Thr Gly
            645                 650                 655

Gly Trp Gly Glu Ser Tyr Val Ser Asn Ile Thr Lys Val Tyr Val Asn
            660                 665                 670

Ile Lys Asp Asp Gln Ala His Ala Val Asn Thr Ala Trp Ala Met Leu
            675                 680                 685

Ala Leu Ile Cys Ala Gly Gln Met Glu Arg Asp Pro Ala Pro Leu His
            690                 695                 700

Arg Ala Ala Lys Glu Leu Ile Asn Met Gln Leu Glu Thr Gly Glu Phe
705                 710                 715                 720

Pro Gln Gln Glu His Val Gly Ala Phe Asn Ala Cys Leu Phe Phe Asn
            725                 730                 735

Tyr Pro Asn Tyr Arg Asn Leu Phe Pro Ile Trp Ala Leu Gly Glu Tyr
```

```
                740             745             750
Cys Arg His Leu His Ser Thr Arg Arg Ala
        755             760

<210> SEQ ID NO 107
<211> LENGTH: 2289
<212> TYPE: DNA
<213> ORGANISM: Zea mays

<400> SEQUENCE: 107
atgtggaggc tgacggtggc cgagggcggc ggcccgtggc tgcgctcgac gaacggcttc     60
gtggggcggg cggtgtggga gttcgaccct gacctcggta cgccggagga gcgcgacgag    120
gtagagaggg tacgccagga gttctccgac caccgcttcc agaggagaga gtcggccgac    180
ctcctcatgc gcatgcagtg cgcaaagcag aacagatctc aacgtcgtga tctgccacgc    240
atcaagcttg gggaggatga gcacgtcact gaagaaattg tactgagctc cttgaggtcg    300
gctctggacc agttctcttc actgcaagcc agcgatgggc actggcctgg tgatttcagc    360
gggattatgt tcatcatgcc tggtttgata tttgccttgt atgtcactgg atcactgaat    420
gttgtcatat caccagaaca tcggcatgag atttgccgct acatctacaa ccaccagaac    480
gaagatggtg gatggggcac acttatcctg ggttcgagca ccatgtttgg cacatgctca    540
aactacatca ccttgaggct ctcggtgag gagccatacg ccaacaacag tgtgttggct    600
aaagggcgtg cttggattct atcccatggt ggtgcaacct tgattcctca gtggggaaaa    660
atatggcttt cggtacttgg attgtttgat tggtcaggaa ataatccaat tttccctgaa    720
ctatggtcca ttccccagtt tcttccattt catccaggga aattctggtg ctttgcccgt    780
atggtatatc taccaatggc ttatctttat ggcaagaaat tgttggacc aattacacca    840 actatattgg cactaagaga ggaaatctat gacactcctt atggaaagat tgactggagt    900
gatgctcgta gtaaatgcgc aaaggaggac ctcatctgtc cacgcacact gttgcagaat    960
gttatttgga cttcactta taggtgtgtg aaccagtat tgagcagttg gcctatcaac   1020
aagctgagag agagctct gggaaacatc atggagcata tccattatga agatgagaac   1080
acacaatacc tatgcatatg tcctgtgaat aaggctctaa acatggtctg ctgctgggta   1140
gaagatccaa attcagatgc attcaagcgt caccttgcaa ggataccaga cttcttgtgg   1200
atttcagaag atggcatgaa ggcacaggta tatgatggct gccagagctg ggagacatca   1260
ttcataattc aagcattttg cgctacagat cttgttaatg actatggttc aactcttcag   1320
agagcctatg agtttatgaa aaattcacag gtcatgagga accatcctgg tgaccaacgt   1380
tattggcatc gccatagatc gaagggttca tggacacttt catctgcaga caatggatgg   1440
gctgtatctg acactacagg agaagcactt aaggctgtac tgttgctgtc aaagatctca   1500
aacaaaaaca accttgttgg ggatccaata gaaagagaaa ggttgcatga cgctattgat   1560
tgccttctat cttttgcgaa caagatggc acctttcta catatgagtg caaaagaact   1620
tattcttggt tagagattct aagtccttgt gagactttcc caaacattgt tgtcgattac   1680
ccttacccag aatgcacttc atcagtgctc caagctctga tattgttcaa agacttatat   1740
cctggttacc gcacagaaga gatagaagca ttagttagaa gtgcagcaac gtttattgag   1800
accaaacaac aagaagacgg ttcatggtta ggtaattggg gtatatgttt cacctacggg   1860
gccttctttt cgattaaagg tttagtcgct tctggaagaa cgtacaagaa cagcccttgc   1920
atacggaaag catgccactt catattgtcg aagcagctca gtactggtgg atggggagaa   1980
```

```
agtcatatcg ctattgaaac tcaggtgtat gtaaatctca aaggtgaccg tgctcacgct    2040
gtgaataccg cctgggcaat gctcgcttta atttatgctg acagtttga acgagatcca    2100 acgccattac atcgtgctgc aaaggaattg atcaacatgc aactggagac aggagagttt    2160
cctcagcaag agcatgtagg atgcttcaac tgcagcctct acttcaatta cccaagctac    2220
cgcaacttgt tccccatctg ggctctcggt gagtaccatc gtggccttcg tgcaaagaaa    2280
gacaattga                                                           2289
```

<210> SEQ ID NO 108
<211> LENGTH: 762
<212> TYPE: PRT
<213> ORGANISM: Zea mays

<400> SEQUENCE: 108

```
Met Trp Arg Leu Thr Val Ala Glu Gly Gly Pro Trp Leu Arg Ser
1               5                   10                  15

Thr Asn Gly Phe Val Gly Arg Ala Val Trp Glu Phe Asp Pro Asp Leu
            20                  25                  30

Gly Thr Pro Glu Glu Arg Asp Glu Val Glu Arg Val Arg Gln Glu Phe
        35                  40                  45

Ser Asp His Arg Phe Gln Arg Arg Glu Ser Ala Asp Leu Leu Met Arg
    50                  55                  60

Met Gln Cys Ala Lys Gln Asn Arg Ser Gln Arg Arg Asp Leu Pro Arg
65                  70                  75                  80

Ile Lys Leu Gly Glu Asp Glu His Val Thr Glu Glu Ile Val Leu Ser
                85                  90                  95

Ser Leu Arg Ser Ala Leu Asp Gln Phe Ser Ser Leu Gln Ala Ser Asp
            100                 105                 110

Gly His Trp Pro Gly Asp Phe Ser Gly Ile Met Phe Ile Met Pro Gly
        115                 120                 125

Leu Ile Phe Ala Leu Tyr Val Thr Gly Ser Leu Asn Val Val Ile Ser
    130                 135                 140

Pro Glu His Arg His Glu Ile Cys Arg Tyr Ile Tyr Asn His Gln Asn
145                 150                 155                 160

Glu Asp Gly Gly Trp Gly Thr Leu Ile Leu Gly Ser Ser Thr Met Phe
                165                 170                 175

Gly Thr Cys Ser Asn Tyr Ile Thr Leu Arg Leu Leu Gly Glu Glu Pro
            180                 185                 190

Tyr Ala Asn Asn Ser Val Leu Ala Lys Gly Arg Ala Trp Ile Leu Ser
        195                 200                 205

His Gly Gly Ala Thr Leu Ile Pro Gln Trp Gly Lys Ile Trp Leu Ser
    210                 215                 220

Val Leu Gly Leu Phe Asp Trp Ser Gly Asn Asn Pro Ile Phe Pro Glu
225                 230                 235                 240

Leu Trp Ser Ile Pro Gln Phe Leu Pro Phe His Pro Gly Lys Phe Trp
                245                 250                 255

Cys Phe Ala Arg Met Val Tyr Leu Pro Met Ala Tyr Leu Tyr Gly Lys
            260                 265                 270

Lys Phe Val Gly Pro Ile Thr Pro Thr Ile Leu Ala Leu Arg Glu Glu
        275                 280                 285

Ile Tyr Asp Thr Pro Tyr Gly Lys Ile Asp Trp Ser Asp Ala Arg Ser
    290                 295                 300

Lys Cys Ala Lys Glu Asp Leu Ile Cys Pro Arg Thr Leu Leu Gln Asn
305                 310                 315                 320
```

```
Val Ile Trp Thr Ser Leu Tyr Arg Cys Val Glu Pro Val Leu Ser Ser
                325                 330                 335

Trp Pro Ile Asn Lys Leu Arg Glu Arg Ala Leu Gly Asn Ile Met Glu
            340                 345                 350

His Ile His Tyr Glu Asp Glu Asn Thr Gln Tyr Leu Cys Ile Cys Pro
        355                 360                 365

Val Asn Lys Ala Leu Asn Met Val Cys Cys Trp Val Glu Asp Pro Asn
    370                 375                 380

Ser Asp Ala Phe Lys Arg His Leu Ala Arg Ile Pro Asp Phe Leu Trp
385                 390                 395                 400

Ile Ser Glu Asp Gly Met Lys Ala Gln Val Tyr Asp Gly Cys Gln Ser
                405                 410                 415

Trp Glu Thr Ser Phe Ile Ile Gln Ala Phe Cys Ala Thr Asp Leu Val
            420                 425                 430

Asn Asp Tyr Gly Ser Thr Leu Gln Arg Ala Tyr Glu Phe Met Lys Asn
        435                 440                 445

Ser Gln Val Met Arg Asn His Pro Gly Asp Gln Arg Tyr Trp His Arg
    450                 455                 460

His Arg Ser Lys Gly Ser Trp Thr Leu Ser Ser Ala Asp Asn Gly Trp
465                 470                 475                 480

Ala Val Ser Asp Thr Thr Gly Glu Ala Leu Lys Ala Val Leu Leu Leu
                485                 490                 495

Ser Lys Ile Ser Asn Lys Asn Leu Val Gly Asp Pro Ile Glu Arg
            500                 505                 510

Glu Arg Leu His Asp Ala Ile Asp Cys Leu Leu Ser Phe Ala Asn Lys
        515                 520                 525

Asp Gly Thr Phe Ser Thr Tyr Glu Cys Lys Arg Thr Tyr Ser Trp Leu
    530                 535                 540

Glu Ile Leu Ser Pro Cys Glu Thr Phe Pro Asn Ile Val Val Asp Tyr
545                 550                 555                 560

Pro Tyr Pro Glu Cys Thr Ser Ser Val Leu Gln Ala Leu Ile Leu Phe
                565                 570                 575

Lys Asp Leu Tyr Pro Gly Tyr Arg Thr Glu Glu Ile Glu Ala Leu Val
            580                 585                 590

Arg Ser Ala Ala Thr Phe Ile Glu Thr Lys Gln Gln Glu Asp Gly Ser
        595                 600                 605

Trp Leu Gly Asn Trp Gly Ile Cys Phe Thr Tyr Gly Ala Phe Phe Ser
    610                 615                 620

Ile Lys Gly Leu Val Ala Ser Gly Arg Thr Tyr Lys Asn Ser Pro Cys
625                 630                 635                 640

Ile Arg Lys Ala Cys His Phe Ile Leu Ser Lys Gln Leu Ser Thr Gly
                645                 650                 655

Gly Trp Gly Glu Ser His Ile Ala Ile Glu Thr Gln Val Tyr Val Asn
            660                 665                 670

Leu Lys Gly Asp Arg Ala His Ala Val Asn Thr Ala Trp Ala Met Leu
        675                 680                 685

Ala Leu Ile Tyr Ala Gly Gln Phe Glu Arg Asp Pro Thr Pro Leu His
    690                 695                 700

Arg Ala Ala Lys Glu Leu Ile Asn Met Gln Leu Glu Thr Gly Glu Phe
705                 710                 715                 720

Pro Gln Gln Glu His Val Gly Cys Phe Asn Cys Ser Leu Tyr Phe Asn
                725                 730                 735
```

Tyr Pro Ser Tyr Arg Asn Leu Phe Pro Ile Trp Ala Leu Gly Glu Tyr
            740                 745                 750

His Arg Gly Leu Arg Ala Lys Lys Asp Asn
        755                 760

<210> SEQ ID NO 109
<211> LENGTH: 1149
<212> TYPE: DNA
<213> ORGANISM: Sorghum bicolor

<400> SEQUENCE: 109
atgtggaggc tcaaggtcgc ggagggcgca gggccatggc taaagtcatc caacaacttc     60
cgtgggcgag ctgtttggga gttcgacccg gagctcggca cgccggagga gcgtgccgag    120
gtggagaggg tgcgccgtga gttcaccgag cgccgctttg agaaaagaga gtcctctgac    180
ctcctcctgc aaatgcagta tgcaaaacat aaacatcttc aggtggatcc tccaccggcc    240
acactcgcag aaaatgaaga agtcacagag gagatcatat tagcagcatt gaagcgagcc    300
ctcgctcaac attcaagtct gcaagcagat gatgggtgct ggccagcaga ttttagtggc    360
attttattca ttatgcctct cctgaatgaa gatggtggtt ggggtaaaca agtgttggga    420
ccaagcacca tgtttggctc atgcttaaac tatgttgcct aagacttat tggtgaagag     480 cgcaaaaatg ttgcattgac caaggacgt gagtggattt tgtcccatgg aagtgcaact     540
gcaattccgc agtggggaaa gatatggttc tcggtgatgg gtttgtatga ttggtctggc    600
aataatccaa taattccaga gttatggctt gtcccacact tcttccaat tcatccagga     660 cgattttggg tttactgccg tatggtgtat ctgcctatgg cttacctctt tgctaaaaaa    720
ttcgttggaa caattacacc aactatactg gaattaaggg acgagctcta tagtatacca    780
tacagtgaga ttgattggaa agaagctcgt gatacttgtg ccaaggtgga ccttgtatat    840
ccaaggacaa tggcacaaaa tcttgtatgg acctgcctta ataaagtcat agagccagta    900
ctgaattgtt ggccattcaa caagttaaga gatatagcat tgaaaaacat tatgaacat     960 atccactatg aagatgaaac tagtaaatac atctgtgtat gtcccataaa caaggcacta   1020
gatatgattt tgttgtgggc agaaaatcca gattcagatg cattcaagca gcatcttcca   1080
aggatatatg atttttatg gcttgcagaa gatggaatga aggcacaggt taaaaagatc   1140
aaaacatag                                                          1149

<210> SEQ ID NO 110
<211> LENGTH: 382
<212> TYPE: PRT
<213> ORGANISM: Sorghum bicolor

<400> SEQUENCE: 110

Met Trp Arg Leu Lys Val Ala Glu Gly Ala Gly Pro Trp Leu Lys Ser
1               5                   10                  15

Ser Asn Asn Phe Arg Gly Arg Ala Val Trp Glu Phe Asp Pro Glu Leu
            20                  25                  30

Gly Thr Pro Glu Glu Arg Ala Glu Val Glu Arg Val Arg Arg Glu Phe
        35                  40                  45

Thr Glu Arg Arg Phe Glu Lys Arg Glu Ser Ser Asp Leu Leu Leu Gln
    50                  55                  60

Met Gln Tyr Ala Lys His Lys His Leu Gln Val Asp Pro Pro Ala
65                  70                  75                  80

Thr Leu Ala Glu Asn Glu Glu Val Thr Glu Glu Ile Ile Leu Ala Ala
                85                  90                  95

Leu Lys Arg Ala Leu Ala Gln His Ser Ser Leu Gln Ala Asp Asp Gly
                100                 105                 110

Cys Trp Pro Ala Asp Phe Ser Gly Ile Leu Phe Ile Met Pro Leu Leu
            115                 120                 125

Asn Glu Asp Gly Gly Trp Gly Lys Gln Val Leu Gly Pro Ser Thr Met
130                 135                 140

Phe Gly Ser Cys Leu Asn Tyr Val Ala Leu Arg Leu Ile Gly Glu Glu
145                 150                 155                 160

Arg Lys Asn Val Ala Leu Thr Lys Gly Arg Glu Trp Ile Leu Ser His
                165                 170                 175

Gly Ser Ala Thr Ala Ile Pro Gln Trp Gly Lys Ile Trp Phe Ser Val
            180                 185                 190

Met Gly Leu Tyr Asp Trp Ser Gly Asn Asn Pro Ile Ile Pro Glu Leu
        195                 200                 205

Trp Leu Val Pro His Phe Leu Pro Ile His Pro Gly Arg Phe Trp Val
    210                 215                 220

Tyr Cys Arg Met Val Tyr Leu Pro Met Ala Tyr Leu Phe Ala Lys Lys
225                 230                 235                 240

Phe Val Gly Thr Ile Thr Pro Thr Ile Leu Glu Leu Arg Asp Glu Leu
                245                 250                 255

Tyr Ser Ile Pro Tyr Ser Glu Ile Asp Trp Lys Glu Ala Arg Asp Thr
            260                 265                 270

Cys Ala Lys Val Asp Leu Val Tyr Pro Arg Thr Met Ala Gln Asn Leu
        275                 280                 285

Val Trp Thr Cys Leu Asn Lys Val Ile Glu Pro Val Leu Asn Cys Trp
    290                 295                 300

Pro Phe Asn Lys Leu Arg Asp Ile Ala Leu Lys Asn Ile Met Glu His
305                 310                 315                 320

Ile His Tyr Glu Asp Glu Thr Ser Lys Tyr Ile Cys Val Cys Pro Ile
                325                 330                 335

Asn Lys Ala Leu Asp Met Ile Cys Cys Trp Ala Glu Asn Pro Asp Ser
            340                 345                 350

Asp Ala Phe Lys Gln His Leu Pro Arg Ile Tyr Asp Phe Leu Trp Leu
        355                 360                 365

Ala Glu Asp Gly Met Lys Ala Gln Val Lys Lys Ile Lys Thr
    370                 375                 380

<210> SEQ ID NO 111
<211> LENGTH: 2274
<212> TYPE: DNA
<213> ORGANISM: Glycine max

<400> SEQUENCE: 111
atgtggaagc tcaagttcgc cgaaggaggg aatccatggc ttcggacatt gaacaatcac      60
gttggaagac aggtgtggga gttcgatcct aagcttggat cgccgcaaga tctcctcgag     120
attgagaaag ctcgccagaa ttttcacgat aaccgcttta cccacaaaca cagcgctgat     180
ctacttatgc ggatgcagtt cgcaagagag aacccaacac gtgaagtctt gcccaaagtc     240
ggagttaagg atattgagga tgtgacccaa gagattgtga caaaaacatt aagaagggcc     300
gtaagtttcc attcaactct ccagtgccat gacggacact ggccgggaga ttatggaggt     360
cccatgtttc tgatgcctgg cttggtaatt actctgtcta tcactgggc gttgaataca      420 gtcttaactg aagaacatag aaaggaaata tgccgttacc tctataatca tcaaaacaag     480

| | | |
|---|---|---|
| gatggtgggt ggggtttgca tattgaaggt ccaagcacca tgtttggctc tgtcttgagt | 540 |
| tatattactc tgagattgct aggtgagggg cctaatgatg acaagggga aatggagaag | 600 |
| gcacgtgact ggattctagg gcatggtggt gctacttata taacgtcatg ggggaagatg | 660 |
| tggcttcag tacttggagt gtatgaatgg tctggaaata atccctgcc cctgagata | 720 |
| tggctccttc catacatgct tccatttcat ccaggaagga tgtggtgtca ctgccggatg | 780 |
| gtctatttgc cgatgtccta cttatatggc aagaggtttg ttggtccaat ctcaccaaca | 840 |
| gtattatctt tgagaaaaga gctttataca gtaccatacc atgatataga ttgggatcag | 900 |
| gctcgcaatt tgtgtgcaaa ggaagatttg tactatcctc acccacttgt acaggatatt | 960 |
| ctttgggcat ctctacacaa gttccttgag cctattctga tgcattggcc tggaaaaaga | 1020 |
| ttgagggaaa aggctattat ttctgcattg gagcatatac attacgaaga tgagaatact | 1080 |
| cgatatattt gcataggtcc tgtaaataag gtgttaaata tgctttgctg ttgggtggaa | 1140 |
| gatccaaatt ctgaggcctt caagttgcat cttcccagga tttatgatta tctatggatt | 1200 |
| gcagaagatg gcatgaaaat gcagggctac aatgaagtc aactatggga cactgctttt | 1260 |
| gctgtccaag caattattgc atctaacctc attgaagaat ttggtccaac tataagaaaa | 1320 |
| gctcataacct atattaagaa ttcacaggtt ttagaagatt gtccaggtga tcttaataaa | 1380 |
| tggtaccgtc acatttcaaa aggtgcttgg ccttttttcaa ctggagatca tggatggcca | 1440 |
| atttctgact gcacagctga aggactgaaa gctgttctat tactatccaa aattgcacca | 1500 |
| gaaatagttg gtgagccaat agacgtgaag cgattatatg attctgtaaa tgtcattctc | 1560 |
| tcactacaga atgaagatgg tggttttgca acatatgagc ttaaacgatc ttataattgg | 1620 |
| ttggagataa tcaatcctgc tgaaactttt ggtgacatcg ttattgatta tccttatgtg | 1680 |
| gaatgtacat cagcagcgat tcaagctttg gcatcattta ggaaattata tcctgggcat | 1740 |
| cgccgagaag aaatacaaca ttgtatcgat aaagccacta ccttcattga aaaaatacaa | 1800 |
| gcttcagatg gatcatggta tggttcttgg ggagtttgct tcacttacgg tgcttggttt | 1860 |
| ggggtaaaag gtctgattgc tgctggaagg agtttcagta attgctcaag catccgtaaa | 1920 |
| gcttgtgaat ttctgctgtc caagcagctt ccttctggtg gctggggaga gagttatctg | 1980 |
| tcctgtcaaa acaaggtgta ttcaaatctg gaaggcaaca ggtctcatgt ggtcaacact | 2040 |
| gggtgggcta tgttggctct cattgatgct ggacaggcta agagagattc gcaaccactg | 2100 |
| caccgggcag ctgcatactt gataaattcc caattggagg acggtgactt tccgcagcag | 2160 |
| gaaataatgg gagtcttcaa caagaattgc atgatcacat acgccgcata cagaaacata | 2220 |
| ttccccattt gggcgttggg agaataccaa tcccaagtat tgcaatctcg ttaa | 2274 |

<210> SEQ ID NO 112
<211> LENGTH: 757
<212> TYPE: PRT
<213> ORGANISM: Glycine max

<400> SEQUENCE: 112

Met Trp Lys Leu Lys Phe Ala Glu Gly Gly Asn Pro Trp Leu Arg Thr
1               5                   10                  15

Leu Asn Asn His Val Gly Arg Gln Val Trp Glu Phe Asp Pro Lys Leu
            20                  25                  30

Gly Ser Pro Gln Asp Leu Leu Glu Ile Glu Lys Ala Arg Gln Asn Phe
        35                  40                  45

His Asp Asn Arg Phe Thr His Lys His Ser Ala Asp Leu Leu Met Arg
    50                  55                  60

```
Met Gln Phe Ala Arg Glu Asn Pro Thr Arg Glu Val Leu Pro Lys Val
 65                  70                  75                  80

Gly Val Lys Asp Ile Glu Asp Val Thr Gln Glu Ile Val Thr Lys Thr
                 85                  90                  95

Leu Arg Arg Ala Val Ser Phe His Ser Thr Leu Gln Cys His Asp Gly
                100                 105                 110

His Trp Pro Gly Asp Tyr Gly Gly Pro Met Phe Leu Met Pro Gly Leu
            115                 120                 125

Val Ile Thr Leu Ser Ile Thr Gly Ala Leu Asn Thr Val Leu Thr Glu
130                 135                 140

Glu His Arg Lys Glu Ile Cys Arg Tyr Leu Tyr Asn His Gln Asn Lys
145                 150                 155                 160

Asp Gly Gly Trp Gly Leu His Ile Glu Gly Pro Ser Thr Met Phe Gly
                165                 170                 175

Ser Val Leu Ser Tyr Ile Thr Leu Arg Leu Leu Gly Glu Gly Pro Asn
                180                 185                 190

Asp Gly Gln Gly Glu Met Glu Lys Ala Arg Asp Trp Ile Leu Gly His
            195                 200                 205

Gly Gly Ala Thr Tyr Ile Thr Ser Trp Gly Lys Met Trp Leu Ser Val
210                 215                 220

Leu Gly Val Tyr Glu Trp Ser Gly Asn Asn Pro Leu Pro Pro Glu Ile
225                 230                 235                 240

Trp Leu Leu Pro Tyr Met Leu Pro Phe His Pro Gly Arg Met Trp Cys
                245                 250                 255

His Cys Arg Met Val Tyr Leu Pro Met Ser Tyr Leu Tyr Gly Lys Arg
                260                 265                 270

Phe Val Gly Pro Ile Ser Pro Thr Val Leu Ser Leu Arg Lys Glu Leu
                275                 280                 285

Tyr Thr Val Pro Tyr His Asp Ile Asp Trp Asp Gln Ala Arg Asn Leu
290                 295                 300

Cys Ala Lys Glu Asp Leu Tyr Tyr Pro His Pro Leu Val Gln Asp Ile
305                 310                 315                 320

Leu Trp Ala Ser Leu His Lys Phe Leu Glu Pro Ile Leu Met His Trp
                325                 330                 335

Pro Gly Lys Arg Leu Arg Glu Lys Ala Ile Ile Ser Ala Leu Glu His
                340                 345                 350

Ile His Tyr Glu Asp Glu Asn Thr Arg Tyr Ile Cys Ile Gly Pro Val
                355                 360                 365

Asn Lys Val Leu Asn Met Leu Cys Cys Trp Val Glu Asp Pro Asn Ser
                370                 375                 380

Glu Ala Phe Lys Leu His Leu Pro Arg Ile Tyr Asp Tyr Leu Trp Ile
385                 390                 395                 400

Ala Glu Asp Gly Met Lys Met Gln Gly Tyr Asn Gly Ser Gln Leu Trp
                405                 410                 415

Asp Thr Ala Phe Ala Val Gln Ala Ile Ala Ser Asn Leu Ile Glu
                420                 425                 430

Glu Phe Gly Pro Thr Ile Arg Lys Ala His Thr Tyr Ile Lys Asn Ser
                435                 440                 445

Gln Val Leu Glu Asp Cys Pro Gly Asp Leu Asn Lys Trp Tyr Arg His
            450                 455                 460

Ile Ser Lys Gly Ala Trp Pro Phe Ser Thr Gly Asp His Gly Trp Pro
465                 470                 475                 480
```

-continued

```
Ile Ser Asp Cys Thr Ala Glu Gly Leu Lys Ala Val Leu Leu Ser
            485                 490                 495

Lys Ile Ala Pro Glu Ile Val Gly Glu Pro Ile Asp Val Lys Arg Leu
            500                 505                 510

Tyr Asp Ser Val Asn Val Ile Leu Ser Leu Gln Asn Glu Asp Gly Gly
        515                 520                 525

Phe Ala Thr Tyr Glu Leu Lys Arg Ser Tyr Asn Trp Leu Glu Ile Ile
    530                 535                 540

Asn Pro Ala Glu Thr Phe Gly Asp Ile Val Ile Asp Tyr Pro Tyr Val
545                 550                 555                 560

Glu Cys Thr Ser Ala Ala Ile Gln Ala Leu Ala Ser Phe Arg Lys Leu
            565                 570                 575

Tyr Pro Gly His Arg Arg Glu Glu Ile Gln His Cys Ile Asp Lys Ala
            580                 585                 590

Thr Thr Phe Ile Glu Lys Ile Gln Ala Ser Asp Gly Ser Trp Tyr Gly
        595                 600                 605

Ser Trp Gly Val Cys Phe Thr Tyr Gly Ala Trp Phe Gly Val Lys Gly
    610                 615                 620

Leu Ile Ala Ala Gly Arg Ser Phe Ser Asn Cys Ser Ser Ile Arg Lys
625                 630                 635                 640

Ala Cys Glu Phe Leu Leu Ser Lys Gln Leu Pro Ser Gly Gly Trp Gly
            645                 650                 655

Glu Ser Tyr Leu Ser Cys Gln Asn Lys Val Tyr Ser Asn Leu Glu Gly
            660                 665                 670

Asn Arg Ser His Val Val Asn Thr Gly Trp Ala Met Leu Ala Leu Ile
            675                 680                 685

Asp Ala Gly Gln Ala Lys Arg Asp Ser Gln Pro Leu His Arg Ala Ala
    690                 695                 700

Ala Tyr Leu Ile Asn Ser Gln Leu Glu Asp Gly Asp Phe Pro Gln Gln
705                 710                 715                 720

Glu Ile Met Gly Val Phe Asn Lys Asn Cys Met Ile Thr Tyr Ala Ala
            725                 730                 735

Tyr Arg Asn Ile Phe Pro Ile Trp Ala Leu Gly Glu Tyr Gln Ser Gln
            740                 745                 750

Val Leu Gln Ser Arg
            755
```